(12) United States Patent  
Baker et al.

(10) Patent No.: US 9,243,238 B2
(45) Date of Patent: *Jan. 26, 2016

(54) SYNTHETIC ENZYMES DERIVED FROM COMPUTATIONAL DESIGN

(75) Inventors: David Baker, Seattle, WA (US); Alexandre Zanghellini, Seattle, WA (US); Lin Jiang, Seattle, WA (US); Andrew Wollacott, Cambridge, MA (US); Daniela Grabs-Röthlisberger, Seattle, WA (US); Eric Althoff, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,699

(22) Filed: Dec. 1, 2011

(65) Prior Publication Data

US 2012/0142077 A1     Jun. 7, 2012

Related U.S. Application Data

(63) Continuation of application No. 12/334,360, filed on Dec. 12, 2008, now Pat. No. 8,340,951.

(60) Provisional application No. 61/013,507, filed on Dec. 13, 2007.

(51) Int. Cl.
*C12N 9/88* (2006.01)
*G06F 19/26* (2011.01)
*G06F 19/24* (2011.01)

(52) U.S. Cl.
CPC . *C12N 9/88* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 6,368,839 | B1 | 4/2002 | Barbas, III et al. |
| 6,589,766 | B1 | 7/2003 | Barbas et al. |
| 6,677,435 | B2 | 1/2004 | Barbas, III et al. |
| 7,407,786 | B2 | 8/2008 | Giver et al. |
| 7,413,888 | B2 | 8/2008 | Fidantsef et al. |
| 2002/0183937 | A1 | 12/2002 | Mayo et al. |
| 2005/0130892 | A1 | 6/2005 | Desjarlais et al. |

(Continued)

OTHER PUBLICATIONS

Tanaka et al., Evolution of aldolase antibodies in vitro: correlation of catalytic activity and reaction-based selection, J Mol Biol. (2004) vol. 335(4), pp. 1007-1018.*

(Continued)

*Primary Examiner* — Alexander Kim
(74) *Attorney, Agent, or Firm* — Cooley LLP

(57) ABSTRACT

Disclosed herein are techniques for computationally designing enzymes. These techniques can be used to design variations of naturally occurring enzymes, as well as new enzymes having no natural counterparts. The techniques are based on first identifying functional reactive sites required to promote the desired reaction. Then, hashing algorithms are used to identify potential protein backbone structures (i.e., scaffolds) capable of supporting the required functional sites. These techniques were used to design 32 different protein sequences that exhibited aldol reaction catalytic function, 31 of which are defined in the Sequence Listing. Details of these 31 different synthetic aldolases are provided, including descriptions of how such synthetic aldolases can be differentiated from naturally occurring aldolases.

33 Claims, 39 Drawing Sheets

(56) References Cited

U.S. PATENT DOCUMENTS

2005/0260655 A1 11/2005 Liu et al.
2007/0269858 A1 11/2007 Jarrell et al.

OTHER PUBLICATIONS

Zanghellini et al., New algorithms and an in silico benchmark for computational enzyme design., Protein Science (Dec. 2006), vol. 15, pp. 2285-2794.*
Branden and Tooze, Intorduction to Protein Structure (1999), 2nd edition, Garland Science Publisher, pp. 3-12.*
Unger et al., The Genetic Algorithm approach to Protein Structure Prediction, Structure and Bonding (2004), vo. 110, pp. 153-175.*
Grunberg et al., Strategies for protein synthetic biology, Nucleic Acids Research (2010), vol. 38(8), pp. 2663-2675.*
Li et al., Current Approaches for Engineering Proteins with Diverse Biological Properties, Adv Exp Med Biol. (2007-B) vol. 620, pp. 18-33.*
Someya et al., GECCO '09 Proceedings of the 11th Annual conference on Genetic and evolutionary computation, pp. 233-240, ACM New York, NY, USA © 2009.*
Goomber et al., Enhancing thermostability of the biocatalysts beyond their natural function via protein engineering, International Journal for Biotechnology and Molecular Biology Research, (2012), vol. 3(3), pp. 24-29.*
Buske et al., In silico characterization of protein chimeras: Relating sequence and function within the same fold, Oct. 2009 Proteins: Structure, Function, and Bioinformatics, vol. 77, Issue 1, pp. 111-120.*
Qu et al., A Guide to Template Based Structure Prediction, Current Protein & Peptide Science (Jun. 2009), vol. 10, pp. 270-285.*
Jiang et al., De Novo Computational Design of Retro-Aldol Enzymes, Science, 2008, vol. 319, pp. 1387-1391.*
Bhanothu et al., Review on characteristic developments of computational protein engineering, Journal of Pharmaceutical Research and Opinion (2012), vol. 2:8, pp. 70-93.*
Xiang et al. (Interchange of Catalytic Activity within the 2-Enoyl-Coenzyme A Hydratase/Isomerase Superfamily Based on a Common Active Site Template., Biochemistry, (1999), vol. 38 (24), pp. 7638-7652.*
Leibowitz et al., Automated Multiple Structure Alignment and Detection of a Common Substructural Motif., Protein: Structure, Function, and Genetics (2001), vol. 43, pp. 235-245.*
Gerlt et al., Enzyme (re)design: lessons from natural evolution and computation., Current Opinion in Chemical Biology (2009), vol. 13, Issue 1, Feb. 2009, pp. 10-18.*
Way et al., Integrating Biological Redesign: Where Synthetic Biology Came From and Where It Needs to Go., Cell (2014), vol. 157, Issue 1, p. 151-161.*
Huang et al., RosettaRemodel: A Generalized Framework for Flexible Backbone Protein Design., PLOSone (2011), vol. 6, e24109, pp. 1-8.*
Richter et al., De Novo Enzyme Design Using Rosetta3., PLOSone (2011), vol. 6, e19230, pp. 1-12.*
Damborsky et al. Computational tools for designing and engineering biocatalysts, Current Opinion in Chmical Biology (2009), vol. 13, pp. 26-34.*
Obexer et al., Active Site Plasticity of a Computationally Designed Retro-Aldolase Enzyme., ChemCatChem (2014), vol. 6, pp. 1043-1050.*
Siegel et al. "Computational Design of an Enzyme Catalyst for a Stereoselective Biomolecular Diels-Alder Reaction" Science, 2010, vol. 329, pp. 309-313.
Tinberg et al. "Computational Design of Ligand-Binding Proteins with High Affinity and Selectivity" Nature, 2013, vol. 501, pp. 212-218.
Khare et al. "Computational Redesign of a Mononuclear Zinc Metalloenzyme for Organophososphate Hydrolysis" Nature Chemical Biology, 2012, vol. 8, pp. 294-300.
Bjelic et al. "Computational Design of Enone-Binding Proteins with Catalytic Activity for the Morita-Baylis-Hillman Reaction" ACS Chemical Biology, 2013, vol. 8, pp. 749-757.
Richter et al. "Computational Design of Catalytic Dyads and Oxyanion Holes for Ester Hydrolysis" Journal of the American Chemical Society, 2012, vol. 134, pp. 16197-16206.
Havranek et al. "Motif-Directed Flexible Backbone Design of Functional Interaction" Protein Science, 2009 vol. 18, pp. 1293-1305.
Barak, Yoram, Yuval Nov, David F. Ackerley, and A. Matin. "Enzyme improvement in the absence of structural knowledge: a novel statistical approach," The ISME Journal (2008) 2, pp. 171-179.
Barbas III, Carlos F., Andreas Heine, Guofu Zhong, Torsten Hoffmann, Svetlana Gramatikova, Robert Bjornestedt, Benjamin List, James Anderson, Enrico A. Stura, Ian A. Wilson, and Richard A. Lerner. "Immune Versus Natural Selection: Antibody Aldolases with Enzymic Rates But Broader Scope," Science vol. 278, Dec. 19, 1997, pp. 2085-2092.
Fullerton, Stephen W.B., Jennifer S. Griffiths, Alexandra B. Merkel, Manoj Cheriyan, Nathan J. Wymer, Michael J. Hutchins, Carol A. Fierke, Eric J. Toone, and James H. Naismith. "Mechanism of the Class I KDPG aldolase," Bioorganic & Medicinal Chemistry 14 (2006) pp. 3002-3010.
Gerlt, John A., and Frank M. Raushel. "Evolution of function in $(\beta/\alpha)_8$ —barrel enzymes," Current Opinion in Chemical Biology 2003, 7, pp. 252-264.
Heine, Andreas, Grace DeSantis, John G. Luz, Michael Mitchell, Chi-Huey Wong, and Ian A. Wilson. "Observation of Covalent Intermediates in an Enzyme Mechanism at Atomic Resolution," Science vol. 294, Oct. 12, 2001, pp. 369-374.
Heine, Andreas, John G. Luz, Chi-Huey Wong, and Ian A. Wilson. "Analysis of the Class I Aldolase Binding Site Architecture Based on the Crystal Structure of 2-Deoxyribose-5-phosphate Aldolase at 0.99 A Resolution," *J Mol. Biol.* (2004) 343, pp. 1019-1034.
Kuhlman, Brian, Gautam Dantas, Gregory C. Ireton, Gabriele Varani, Barry L. Stoddard, and David Baker. "Design of a Novel Globular Protein Fold with Atomic-Level Accuracy," Science vol. 302, Nov. 21, 2003, pp. 1364-1368.
Schorken, Ulrich, Stina Thorell, Melanie Schurmann, Jia Jia, Georg A. Sprenger, and Gunter Schneider. "Identification of catalytically important residues in the active site of *Escherichia coli*transaldolase," *Eur. J Biochem.* 268, (2001), pp. 2408-2415.
Tanaka, Fujie, and Carlos F. Barbas III. "Phage display selection of peptides possessing aldolase activity," Chem. Commun., 2001, pp. 769-770.
Thorell, Stina, Peter Gergely Jr., Katalin Banki, Andras Pert, and Gunter Schneider. "The three-dimensional structure of human transaldolase," FEBS Letters 475 (2000), pp. 205-208.
Bolon, Daniel N., Christopher A. Voigt, and Stephen L. Mayo. "De novo design of biocatalysts," Current Opinion in Chemical Biology 2002, 6: 125-129.
Bolon, Daniel N. and Stephen L. Mayo. "Enzyme-like proteins by computational design," PNAS, vol. 98, No. 25; 14274-14279, Dec. 4, 2001.
Cesaro-Tadic, Sandro, Dimitrios Lagos, Annemarie Honegger, James H. Rickard, Lynda J. Partridge, G. Michael Blackburn, and Andreas Pluckthun, "Turnover-based in vitro selection and evolution of biocatalysts from a fully synthetic antibody library," Nature Biotechnology, vol. 21, No. 6; 679-685, Jun. 2003.
Chica, Roberto A., Nicolas Doucet, and Joelle N. Pelletier, "Semi-rational approaches to engineering enzyme activity: combining the benefits of directed evolution and rational design," Current Opinion in Biotechnology 2005, 16:378-384.
Clarke, Neil D. and Shao-Min Yuan, "Metal Search: A Computer Program That Helps Design Tetrahedral Metal-Binding Sites," Proteins: Structure, Function, and Genetics 23:256-263 (1995).
Dahiyat, Bassil I. and Stephen L. Mayo, "De Novo Protein Design: Fully Automated Sequence Selection," Science, vol. 278, pp. 82-87. Oct. 3, 1997.
Dahiyat, Bassil I. and Stephen L. Mayo, "Protein design automation," Protein Science (1996), 5: 895-903.
Dwyer, Mary A., Loren L. Looger, and Homme W. Hellinga, "Computational Design of a Biologically Active Enzyme," Science, vol. 304, pp. 1967-1971. Jun. 25, 2004.

(56) References Cited

OTHER PUBLICATIONS

Hellinga, Homme W. and Frederic M. Richards, "Construction of New Ligand Binding Sites in Proteins of Known Structure-I. Computer-aided Modeling of Sites with Pre-defined Geometry," J. Mol. Biol. (1991) 222, 763-785.

Hilvert, Donald, "Critical Analysis of Antibody Catalysts," Annu. Rev. Biochem. 2000. 69: 751-793. 011 Hollfelder, Florian, Anthony J. Kirby, and DanS. Tawfik, "Efficient Catalysts of Proton Transfer by Synzymes," J. Am. Chern. Soc. 1997, 119, 9578-9579.

Kaplan, J. And W.F. DeGrado, "De novo designs of catalytic proteins," PNAS, vol. 101, No. 32, pp. 1156611570. Aug. 10, 2004.

Kortemme, Tanja, Lukasz A. Joachimiak, Alex N. Bullock, Aaron D. Schuler, Barry L. Stoddard, and David Baker, "Computational redesign of protein-protein interaction specificity," Nature Structural & Molecular Biology, vol. 11, No. 4, pp. 371-379. Apr. 2004.

Meiler, Jens and David Baker, "Rosettaligand: Protein-Small Molecule Docking with Full Side-Chain Flexibility," Proteins: Structure, Function, and Bioinformatics 65: 538-548 (2006).

Nanda, Vikas, Michael M. Rosenblatt, Artur Osyczka, Hidetoshi Kono, Zelleka Getahun, P. Leslie Dutton, Jeffery G. Saven, and William F. DeGrado, "De Novo Design of a Redox-Active Minimal Rubredoxin Mimic," J. Am. Chem. Soc.2005, 127, 5804-5805.

Seelig, Burckhard and Jack W. Szostak, "Selection and evolution of enzymes from a partially randomized non-catalytic scaffold," Nature, vol. 448, pp. 828-833. Aug. 16, 2007.

Tantillo, Dean J., Jiangang Chen, and Kendall N. Houk, "Theozymes and compuzymes: theoretical models for biological catalysis," Current Opinion in Chemical Biology 1998, 2: 743-750.

Varadarajan, Navin, Jongsik Gam, Mark J. Olsen, George Georgiou, and Brett L. Iverson, "Engineering of protease variants exhibiting high catalytic activity and exquisite substrate selectivity," PNAS, vol. 102, No. 19, pp. 6855-6860. May 10, 2005.

Christendat et al., Crystal Structure of dTDP-4-keto-6-deoxy-D-hexulose 3,5-Epimerase from Methanobacterium thermoautotrophicum Complexed with dTDP, J. Biological Chemistry, Aug. 11, 200, vol. 275, pp. 24609, 24611, Fig 1.

Hakulinen et al., RCSB Protein Data Bank Submission based on the article, Thermophilic b-1 ,4-xylanase from Nonomuraea flexuosa, European Journal of Biochemistry, 2003, vol. 270, pp. 1399-1412, published Jul. 8, 2003.

Hennig et al., RCSB Protein Data Bank Submission based on the article, Crystal structure of indolglycerol phosphate synthase (IGPS) with reduced 1-(o-carboxyphenylamino)-1-deoxyribulose-5-phosphate (RCDRP), J. Molecular Biology, vol. 139, pp. 757-766, published Jun. 12, 2002.

Hennig et al., RCSB Protein Data Bank Submission based on the article, Crystal structure of indolglycerol phosphate synthase (IGPS) in complex with 1-(o-carboxyphenylamino)-1-deoxyribulose-5-phosphate (CDRP), J. Molecular Biology, Vol, 319, pp. 757-766, published Sep. 18, 2002.

Hennig et al., RCSB Protein Data Bank Submission based on the article, Indole-3-glycerophosphate synthase from Sulfolobus solfataricus at 2.0 A resolution, Structure, 1995, vol. 3, pp. 1295-1306, published Jul. 11, 1996.

Hennig et al., RCSB Protein Data Bank Submission based on the article, Complex of indole-3-glycerophosphate synthase from Sulfolobus solfataricus with indole-3-glycerophosphate at 2.0 A resolution, J. Molecular Biology, vol. 319, pp. 757-766, published Mar. 23, 1999.

Knoechel et al., RCSB Protein Data Bank Submission based on the article, Crystal structure of indolglycol phosphate synthase from Thermotoga maritima, J. Biological Chemistry, 2002, vol. 277, pp. 8626-8634, published Mar. 20, 2003.

Lang et al., RCSB Protein Data Bank Submission based on the article, Cylase subunit of imidazoleglyerolphosphate synthase from Thermotoga maritima, Science, 2000, vol. 289, pp. 1546-1550, published Jul. 14, 2000.

McCarthy et al., RCSB Protein Data Bank Submission based on the article, Crystal structure of XYNB, a highly thermostable beta-1,4-xylanase from Dictyglomus thermophilum RT46B.1 at 1.8 A resolution, Acta Crystallographica, Sect D, 2000, vol. 56, pp. 1367-1375, published Nov. 15, 2000.

Zanghellini, A. et al., New algorithms and an in silico benchmark for computational enzyme design, Protein Science, 2006, pp. 2878, 2788.

Zanghellini et al. Protein Science (2006), 15:2785-2794.

Bachar et al. A computer vision based technique for 3-D sequence-independent structural comparison of proteins Protein Engineering, design and selection, 1993, 6 (3): 279-280.

Russell R. J. Mol. Bioi. (1998) 279, 1211-1227.

Thorell et al. J. Mol. Bioi. (2002) 319, 161-171.

\* cited by examiner

Table 1. Crystal structures of enzyme-transition state analog complexes

| PDB code | Resolution (Å) | Enzyme name | EC class | Molecular function |
|---|---|---|---|---|
| 1h2j | 1.15 | Bacillus agaradhaerens endoglucanase Cel5A | Hydrolase | Glycosidase |
| 1oex | 1.10 | Cryphonectria parasitica aspartic proteinase | Hydrolase | Aspartic endopeptidase |
| 1p6o | 1.14 | Yeast cytosine deaminase | Hydrolase | Deaminase |
| 3vgc | 1.67 | Bos taurus γ-chymotrypsin | Hydrolase | Serine endopeptidase |
| 6cpa | 2.00 | Bos taurus carboxypeptidase A | Hydrolase | Metallocarboxypeptidase |
| 1ney | 1.20 | Saccharomyces cerevisiae triosephosphate isomerase | Isomerase | Isomerase |
| 1dqx | 2.40 | Saccharomyces cerevisiae orotidine 5'phosphate decarboxylase | Lyase | Decarboxylase |
| 1jcl | 1.05 | Escherichia coli D-2-deoxyribose 5-phosphate aldolase | Lyase | Aldolase (class I) |
| 4fua | 2.43 | Escherichia coli 1-fuculose 1-phosphate aldolase | Lyase | Aldolase (class II; $Zn^{2+}$) |
| 1c2t | 2.10 | Escherichia coli glycinamide ribonucleotide transformylase | Transferase | Transferase |

FIG. 3

Table 5. RosettaMatch results on homologous structures

| PDB code | Catalytic residues | Homolog structure | RMSD (Å)[a] | Sequence identity | Native matches |
|---|---|---|---|---|---|
| 1oex | 2 | 1bxqA | 1.39 | 56% | 47 |
|  | 2 | 1aprE | 2.4 | 53% | 36 |
|  | 2 | 3aprE | 2.85 | 39% | 16 |
|  | 2 | 1psoE | 3.33 | 36% | 79 |
|  | 2 | 1pfzA | 3.95 | 24% | 0 |
| 3vgc | 3 | 1f7zA | 1.59 | 43% | 27 |
|  | 3 | 1xxdA | 2.61 | 40% | 2 |
|  | 3 | 1loB | 3.6 | 39% | 0 |
| 1p6o | 4 | 1wkqA | 3.56 | 22% | 106 |
|  | 4 | 1xq2A | 1.66 | 22% | 104 |
|  | 4 | 1wwrA | 3.91 | 23% | 113 |
| 6cpa | 4 | 2bo9A | 0.83 | 60% | 37 |
|  | 4 | 1kwmA | 1.25 | 46% | 56 |
|  | 4 | 1jggA | 2.97 | 30% | 0 |

[a]Backbone RMSD.

Table 3. Benchmark I results using inverse rotamer tree approach (A) and the RosettaMatch method (B)

| PDB code | Catalytic residues | Matches | | Top ranking native match | |
|---|---|---|---|---|---|
| | | Number of matches | Number of native matches[a] | After minimization | After design |
| A. Rotamer tree approach | | | | | |
| 1h2j | Glu, Glu | 435 | 22 | 1 (55)[b] | 2 |
| 1oex | Asp, Asp | 1195 | 20 | 1 (220) | 11 |
| 1p6o | His, Cys, Cys, Glu | 742 | 106 | 2 | 1 |
| 3vgc | Ser, His, Asp | 113 | 23 | 1 | 1 |
| 6cpa | His, Glu, His, Glu | 426 | 195 | 3 | 1 |
| 1ney | Lys, His, Glu | 1331 | 4 | 87 | 1 |
| 1dqx | Lys, Asp, Lys, Asp | 4044 | 49 | 34 | 2 |
| 1jcl | Lys, Asp, Lys | 1765 | 6 | 42 | 6 |
| 4fua | His, His, His | 73 | 32 | 4 | 1 |
| 1c2t | Asn, His, Asp | 172 | 108 | 5 | 1 |
| B. RosettaMatch method | | | | | |
| 1h2j | Glu, Glu | 1965 | 70 | 1 (191) | 6 |
| 1oex | Asp, Asp | 1129 | 6 | 1008 | 390 |
| 1p6o | His, Cys, Cys, Glu | 551 | 424 | 1 (243) | 1 |
| 3vgc | Ser, His, Asp | 140 | 75 | 4 | 1 |
| 6cpa | His, Glu, His, Glu | 2075 | 16 | 32 | 12 |
| 1ney | Lys, His, Glu | 1004 | 39 | 11 | 1 |
| 1dqx | Lys, Asp, Lys, Asp | 24,323 | 544 | 37 | 1 |
| 1jcl | Lys, Asp, Lys | 2630 | 0 | —[c] | —[c] |
| 4fua | His, His, His | 110 | 60 | 1 (53) | 1 |
| 1c2t | Asn, His, Asp | 497 | 201 | 1 (274) | 1 |

[a] Native matches indicates matches with native catalytic residues positions in native scaffold.
[b] Tie for the first place. In parentheses is the total number of top-ranked matches.
[c] No native match found. The crystal structure active site has a nonstandard bond angle for catalytic Lys201 that prevents finding matches with the backbone dependent rotamer library with parameters used for all other cases. Addition of a rotamer with the same nonideal bond angle in the rotamer library allows finding native matches as in the other cases. Alternatively, increase in the matching threshold allows recovery at the native site, even with the Dunbrack backbone library, but leads to a huge increase in the number of matches for the other cases.

*FIG. 5*

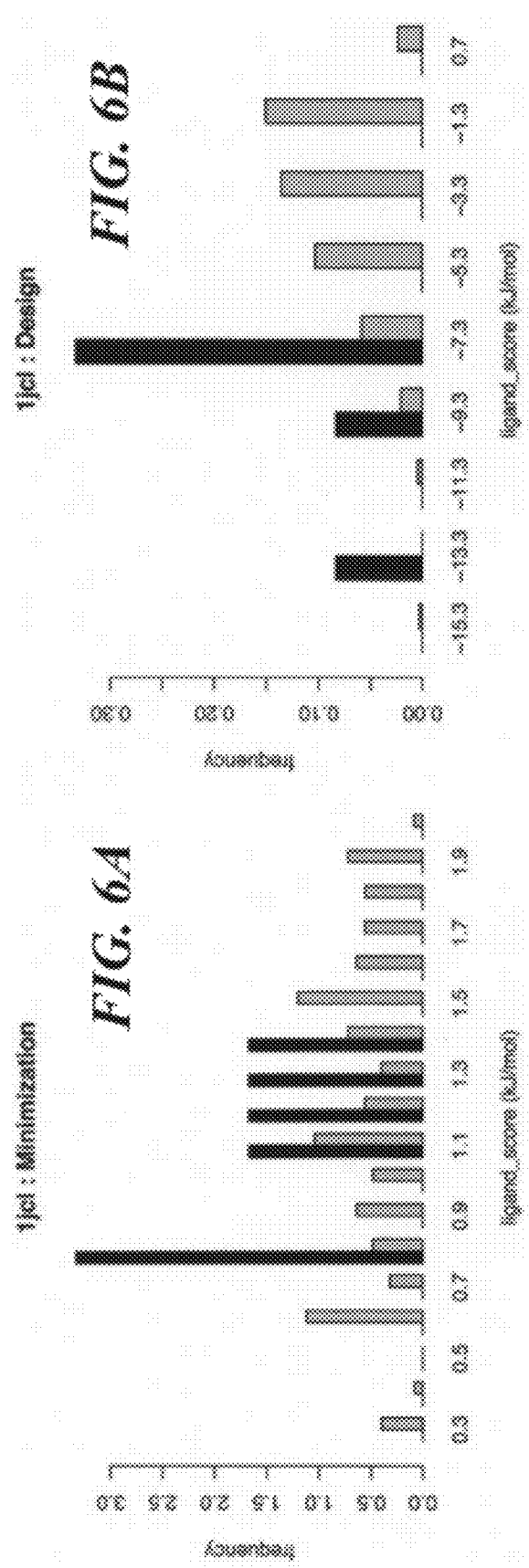

Table 4. *Benchmark II results using RosettaMatch*

| PDB code | Catalytic residues | Matches | | Top ranking native match | |
|---|---|---|---|---|---|
| | | Number of matches | Number of native matches | After minimization | After design |
| 1h2j | Glu, Glu | 20,390 | 484 | 144 | 306 |
| 1oex | Asp, Asp | 12,808 | 2 | 9354 | 4149 |
| 1p60 | His, Cys, Cys, Glu | 72,600 | 28 | 1 | 1 |
| 5vgc | Ser, His, Asp | 11,346 | 300 | 1 | 1 |
| 6cpa | His, Glu, His, Glu | 2177 | 48 | 1 | 17 |
| 1ney | Lys, His, Glu | 36,367 | 33 | 23 | 79 |
| 1jcl | Lys, Asp, Lys | 111 | 6 | 56 | 8 |
| 4fua | His, His, His | 20,730 | 1458 | 1 | 1 |
| 1c2t | Asn, His, Asp | 108 | 24 | 1 | 1 |

Benchmark search and results are based on the native scaffold only. Results for 1dgx are not reported in this table because matching for that scaffold led to an explosion of the number of files, due to the particular combinatorics of that active site (2 Lys + 2 Asp/Glu). However, native matches were found for that scaffold as for the other with full diversification.

*FIG. 8*

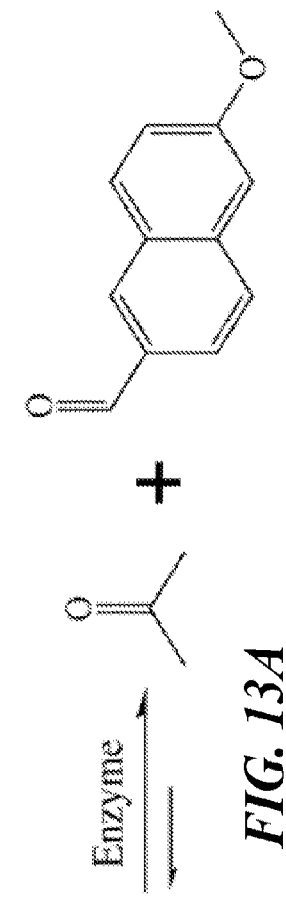
FIG. 13A
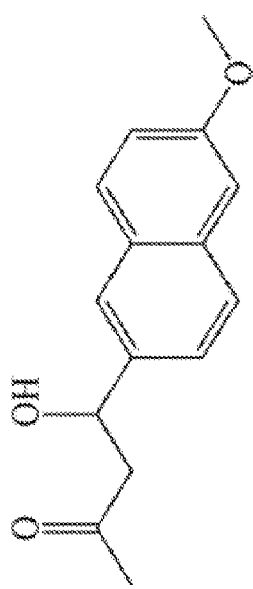
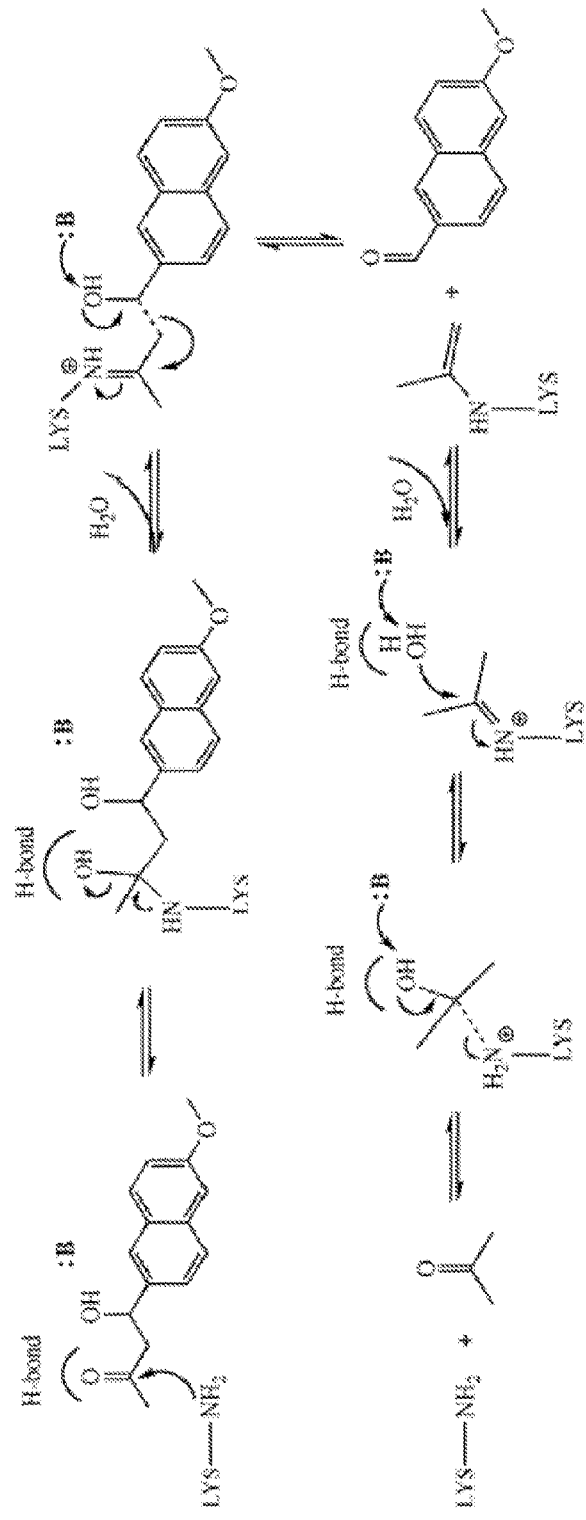
FIG. 13B

Table 5 Enaminone formation and enzyme activity for different active site motifs

| Motif | Catalytic lysine environment | Carbinolamine stabilization | Proton abstraction | # tested | # forming enaminone | # active designs | Rate enhancement |
|---|---|---|---|---|---|---|---|
| I | Polar | - | Lys/Asp dyad | 12 | 2 | 0 | |
| II | Hydrophobic | - | Tyr | 9 | 1 | 0 | |
| III | Hydrophobic | H-bond acceptor/donor | His/Asp dyad | 13 | 10 | 10 | $10^2$~$10^3$ |
| IV | Hydrophobic | Water, H-bond acceptor | Water | 38 | 20 | 22 | $10^3$~$10^4$ |

*FIG. 14*

Table 6.

Kinetic parameters of selected designs

| Design | $k_{cat}$ (×10$^{-3}$ min$^{-1}$) | $K_M$ (µM) | $k_{cat}/K_M$ (M$^{-1}$s$^{-1}$) | $k_{cat}/k_{uncat}$* |
|---|---|---|---|---|
| RA22 | $_b$3.1 ± 0.3 | $_b$480 ± 130 | $_b$0.11 ± 0.03 | $_b$8.1 × 10$^3$ |
|  | $_s$0.5 ± 0.1 | $_s$450 ± 210 | $_s$0.018 ± 0.006 | $_s$1.2 × 10$^3$ |
| RA34 | $_b$4.2 ± 1.1 | $_b$620 ± 180 | $_b$0.11 ± 0.01 | $_b$1.1 × 10$^4$ |
|  | $_s$0.6 ± 0.1 | $_s$600 ± 140 | $_s$0.016 ± 0.004 | $_s$1.5 × 10$^3$ |
| RA45 | 2.3 ± 0.2 | 430 ± 48 | 0.091 ± 0.004 | 6.0 × 10$^3$ |
| RA46 | 0.62 ± 0.5 | 290 ± 60 | 0.037 ± 0.006 | 1.6 × 10$^3$ |
| RA60 | 9.3 ± 0.9 | 510 ± 33 | 0.30 ± 0.06 | 2.4 × 10$^4$ |
| RA61 | 9.0 ± 1.0 | 210 ± 50 | 0.74 ± 0.11 | 2.3 × 10$^4$ |

* $k_{uncat}$ = 3.9 × 10$^{-7}$ min$^{-1}$ (*16*)   b = burst phase, s = steady state

*FIG. 16*

Table 7.

Rate enhancements for active designs

| Design name | PDB code | Catalytic lysine position | Number of amino acid changes | Active site type | Additional mutations | Rate (min$^{-1}$)* at 270 μM racemic substrate | Rate enhancement of lysine knockout mutation |
|---|---|---|---|---|---|---|---|
| Uncatalyzed rate | | | | | | $3.9 \times 10^{-7}$ | |
| *Jelly rolls* | | | | | | | |
| RA61 | 1m4w | 176 | 8 | IV | | $6.3 \times 10^{-3}$ | 1 |
| RA60 | 1m4w | 48 | 12 | IV | | $3.4 \times 10^{-3}$ | 1 |
| RA59 | 1m4w | 176 | 9 | IV | | $1.4 \times 10^{-3}$ | n.d. |
| RA28 | 1f5j | 180 | 6 | III | | $1.3 \times 10^{-4}$ | 1 |
| *TIM barrels* | | | | | | | |
| RA17 | 1thf | 126 | 14 | III | | $2.1 \times 10^{-5}$ | 1 |
| RA58 | 1thf | 169 | 10 | IV | | $9.0 \times 10^{-5}$ | 1 |
| RA31 | 1i4n | 179 | 14 | III | | $8.1 \times 10^{-5}$ | 1 |
| RA32 | 1i4n | 177 | 13 | III | | $5.1 \times 10^{-5}$ | 110 |
| RA33 | 1i4n | 177 | 15 | III | | $4.0 \times 10^{-5}$ | 120 |
| RA22 | 1lbf | 159 | 13 | III | | $1.3 \times 10^{-3}$, $2.2 \times 10^{-4}$ | 1 |
| | | | | | S210A | $6.5 \times 10^{-5}$ | n.d. |
| RA34 | 1lbf | 159 | 13 | IV | | $1.5 \times 10^{-4}$, $1.9 \times 10^{-4}$ | n.d. |
| | | | | | Y51V | $3.2 \times 10^{-4}$ | n.d. |
| RA35 | 1lbf | 159 | 14 | IV | | $5.1 \times 10^{-4}$ | n.d. |
| RA36 | 1lbf | 159 | 17 | IV | | $1.6 \times 10^{-4}$ | n.d. |
| RA47 | 1lbf | 159 | 15 | IV | | $7.2 \times 10^{-4}$ | n.d. |
| RA39 | 1lbf | 178 | 14 | IV | | $7.7 \times 10^{-5}$ | 1 |
| RA41 | 1lbf | 178 | 17 | IV | | $2.1 \times 10^{-5}$ | n.d. |
| RA63 | 1igs | 131 | 11 | IV | | $6.2 \times 10^{-4}$ | n.d. |
| RA6 | 1lbl | 178 | 15 | III | | $9.0 \times 10^{-4}$ | 1 |
| | | | | | T159V | $5.6 \times 10^{-5}$ | n.d. |
| RA42 | 1lbl | 178 | 15 | IV | | $5.5 \times 10^{-5}$ | n.d. |
| RA44 | 1lbl | 178 | 17 | IV | | $9.5 \times 10^{-5}$ | n.d. |
| RA45 | 1lbl | 180 | 13 | IV | | $9.3 \times 10^{-4}$ | 1 |
| | | | | | E233T | $4.3 \times 10^{-4}$ | n.d. |
| RA46 | 1lbl | 180 | 14 | IV | | $3.3 \times 10^{-4}$ | 1 |
| RA48 | 1lbl | 131 | 16 | IV | | $7.0 \times 10^{-4}$ | 1 |
| RA55 | 1lbl | 159 | 12 | IV | | $5.8 \times 10^{-4}$ | n.d. |
| RA56 | 1lbl | 159 | 16 | IV | | $7.2 \times 10^{-5}$ | n.d. |
| RA57 | 1lbl | 159 | 13 | III | | $1.5 \times 10^{-3}$ | n.d. |
| RA49 | 1lbl | 178 | 17 | III | | $1.9 \times 10^{-4}$ | n.d. |
| RA26 | 1a53 | 131 | 10 | III | | $3.2 \times 10^{-5}$ | 1 |
| RA40 | 1a53 | 178 | 17 | IV | | $3.5 \times 10^{-5}$ | n.d. |
| RA43 | 1a53 | 178 | 16 | IV | | $3.8 \times 10^{-5}$ | n.d. |
| RA53 | 1a53 | 159 | 16 | IV | | $9.0 \times 10^{-5}$ | n.d. |
| RA68 | 1a53 | 53 | 10 | IV | | $5.4 \times 10^{-4}$ | 1 |

Table 8. Catalytic residues and parameters of catalysts and their knock-out mutants

| design | PDB code | base | Hbond donor | π-stack | $k_{cat}$ ($s^{-1}$) | $K_M$ (mM) | $k_{cat}/K_M$ ($s^{-1}M^{-1}$) | $k_{cat}/k_{uncat}$ |
|---|---|---|---|---|---|---|---|---|
| KE07 | 1thf | E101 | K222 | W50 | 0.018±0.001 | 1.4±0.1 | 12.2±0.1 | $1.6×10^4$ |
| KE07 | 1thf | E101A | K222 | W50 | 0.0009±0.0004 | 0.29±0.14 | 3.5±1.0 | $7.8×10^2$ |
| KE07 | 1thf | E100 | K222A | W50 | 0.030±0.004 | 1.3±0.2 | 22.7±2.7 | $2.6×10^4$ |
| KE10 | 1a53 | E178 | none | W210 | NA | NA | 51.6±4.0 | NA |
| KE10 | 1a53 | E178Q | none | W210 | NA | NA | 0.17±0.17 | NA |
| KE15 | 1thf | D48 | none | Y126 | 0.022±0.003 | 0.63±0.09 | 35.1±4.8 | $1.9×10^3$ |
| KE15 | 1thf | D48A | none | Y126 | NA | NA | 0.05±0.07 | NA |
| KE16 | 1thf | D48 | K201 | Y126 | 0.006±0.001 | 4.2±0.1 | 13.4±1.4 | $5.2×10^2$ |
| KE16 | 1thf | D48A | K201 | Y126 | n.d. | n.d. | n.d. | n.d. |
| KE59 | 1a53 | E231 | none | W110 | 0.29±0.11 | 1.8±0.6 | 163±21 | $2.5×10^3$ |
| KE59 | 1a53 | E231Q | none | W110 | NA | NA | 0.003±0.002 | NA |
| KE59 | 1a53 | E231 | G131S | W110 | NA | NA | 17.9±0.7 | NA |
| KE61 | 1h61 | E100 | none | W184 | NA | NA | 7.9±0.6 | NA |
| KE61 | 1h61 | E100A | none | W184 | NA | NA | 0.7±0.1 | NA |
| KE70 | 1jcl | H16-D44 | S137 | Y47 | 0.16±0.05 | 2.1±0.8 | 78.3±13.7 | $1.4×10^3$ |
| KE70 | 1jcl | H16A-D44 | S137 | Y47 | NA | NA | 0.02±0.03 | NA |
| KE70 | 1jcl | H16-D44N | S137 | Y47 | 0.06±0.03 | 2.3±1.5 | 29.8±4.6 | $5.2×10^2$ |
| KE71 | 1a53 | H89-D85 | Y210 | W184 | NA | NA | 5.9±0.2 | NA |
| KE71 | 1a53 | H89A-D85 | Y210 | W184 | NA | NA | 0.4±0.2 | NA |
| KE71 | 1a53 | H89-D85N | Y210 | W184 | NA | NA | 1.0±0.2 | NA |

Table 9. Catalytic parameters of the designed KE07 and its evolved variants

| variant | mutations | $k_{cat}$, $s^{-1}$ | $K_M$, mM | $k_{cat}/K_M$, $M^{-1}s^{-1}$ | $k_{cat}/k_{uncat}$[a] |
|---|---|---|---|---|---|
| KE07 WT | - | 0.018±0.001 | 1.4±0.1 | 12.2±0.1 | $1.55 \times 10^4$ |
| R2 11/10D | K19E Q123R K146T G202R N224D | 0.021±0.001 | 0.31±0.02 | 66±2 | $8.38 \times 10^4$ |
| R3 I3/10A | I7Q F86L K146T G202R N224D F229S | 0.206±0.003 | 0.48±0.03 | 425±16 | $1.78 \times 10^5$ |
| R3 I3/10A E101A | | | | ≤3.9 | |
| R4 1E/11H | I7D K146E G202R N224D | 0.699±0.001 | 2.40±0.07 | 291±9 | $6.02 \times 10^5$ |
| R4 1E/11H E101A | | | | ≤2.4 | |
| R5 10/3B | I7D V12M G202R N224D | 0.49±0.01 | 0.59±0.03 | 836±18 | $4.22 \times 10^5$ |
| R6 3/7F | I7D K19E K146T G202R N224D | 0.60±0.07 | 0.69±0.09 | 872±25 | $5.17 \times 10^5$ |
| R7 2/5B | I7D F77L G202R N224D | 1.20±0.08 | 0.86±0.08 | 1388±44 | $1.03 \times 10^6$ |
| R7 10/11G | I7D V12M F77L I102F K146T G202R N224D F229S | 1.37±0.14 | 0.54±0.12 | 2590±302 | $1.18 \times 10^6$ |

[a] $k_{uncat}$ ($1.16 \times 10^{-6}$ $s^{-1}$) was determined in HEPES buffer at pH 7.25, and extrapolated to zero buffer concentration.

*FIG. 22*

ALPHA-BETA BARREL/TIM BARREL

JELLY ROLL

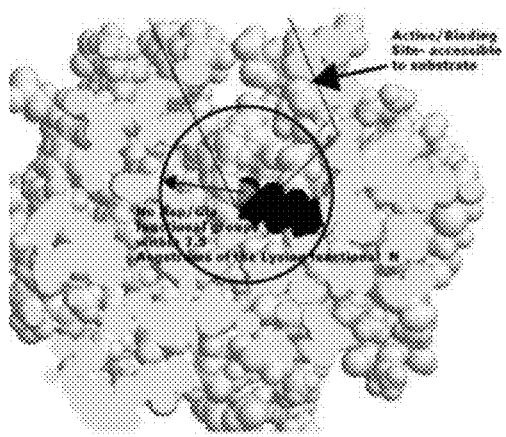 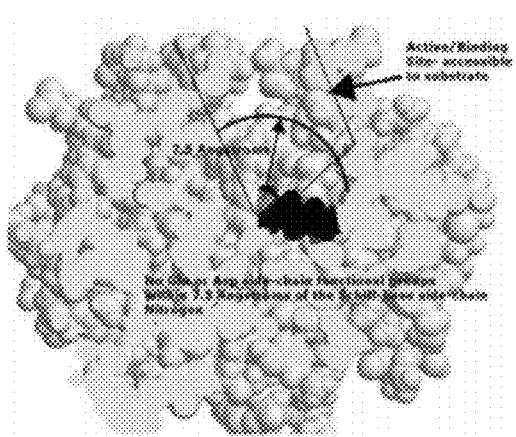
*FIG. 29C*  *FIG. 29D*

FIG. 30A

| | | 7 | 47 | 49 | 79 | 81 | 83 | 87 | 106 | 108 | 110 | 129 | 131 | 155 | 157 | 177 | 179 | 183 | 209 | 210 | 229 |
|---|---|---|---|---|---|---|---|---|---|---|---|---|---|---|---|---|---|---|---|---|---|
| 1i4n | | I | E | K | S | L | E | F | L | K | F | L | I | L | L | G | N | L | E | S | L |
| RA31 | 14 | A | Q | S | L | D | A | - | - | H | I | V | - | - | - | - | - | - | - | W | - |
| RA32 | 13 | - | Q | S | T | D | - | - | V | H | - | V | - | V | - | A | A | F | - | S |
| RA33 | 15 | - | Q | S | T | D | A | A | V | H | - | - | - | V | V | A | A | L | - | S |

FIG. 30B

| | | 9 | 51 | 53 | 56 | 58 | 81 | 83 | 99 | 110 | 112 | 131 | 135 | 159 | 161 | 178 | 180 | 182 | 184 | 187 | 210 | 211 | 231 | 233 |
|---|---|---|---|---|---|---|---|---|---|---|---|---|---|---|---|---|---|---|---|---|---|---|---|---|
| 1lbf | | L | E | K | S | S | S | L | F | K | F | L | K | E | N | G | N | R | L | L | E | S | L | G |
| RA22 | 13 | - | G | D | - | - | - | T | - | A | - | A | - | - | - | - | V | A | W | - | S | F | S | H |
| RA34 | 13 | - | Y | M | - | W | - | T | A | A | - | A | - | - | - | - | Y | - | W | - | S | Y | S | - |
| RA35 | 14 | - | G | I | - | - | A | A | T | G | - | A | - | - | - | - | I | - | W | - | S | Y | S | Y |
| RA36 | 17 | - | G | V | G | - | - | A | A | W | - | A | - | - | - | - | V | A | W | G | S | S | A | Y |
| RA39 | 14 | - | G | S | - | T | - | T | - | T | - | T | - | - | T | - | L | - | W | - | S | F | S | Y |
| RA41 | 17 | A | V | S | - | - | T | Y | W | A | L | V | P | V | V | K | K | - | W | - | S | - | I | - |
| RA47 | 15 | - | G | M | - | W | A | T | A | A | - | A | - | - | - | - | V | - | W | - | S | V | S | V |

|  | 9 | 11 | 48 | 78 | 101 | 103 | 126 | 128 | 130 | 169 | 171 | 176 | 201 | 222 | 224 |
|---|---|---|---|---|---|---|---|---|---|---|---|---|---|---|---|
| 1thf | C | D | V | T | S | N | V | A | D | L | T | D | S | L | A |
| RA17 | 14 | V | L | A | I | - | L | - | - | F | A | V | L | D | H | A | D |
| RA58 | 10 | S | Y | T | - | - | H | - | S | W | (x) | V | W | H | - | - |

FIG. 30F

|  | 46 | 48 | 72 | 74 | 87 | 89 | 119 | 121 | 133 | 135 | 137 | 176 | 178 |
|---|---|---|---|---|---|---|---|---|---|---|---|---|---|
| 1m4w | N | V | N | Y | E | Y | T | R | F | Q | W | E | Y |
| RA59 | 9 | T | - | Y | - | S | - | G | Y | - | I | V | (x) | S |
| RA60 | 12 | W | (x) | T | W | S | S | Y | W | - | Y | S | - | V | V |
| RA61 | 8 | H | M | I | - | - | L | - | - | - | - | I | - | W |

FIG. 30G

|  | 16 | 43 | 45 | 81 | 90 | 180 |
|---|---|---|---|---|---|---|
| 1f5j | E | N | L | Y | E | E |
| RA28 | 6 | A | F | A | F | T | (x) |

FIG. 30H

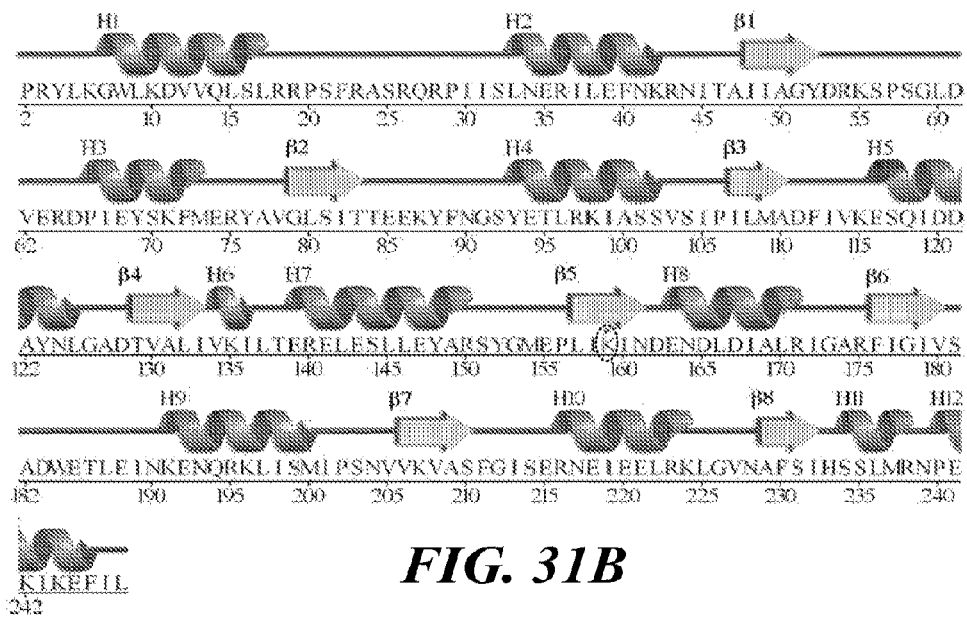
FIG. 31A
FIG. 31B
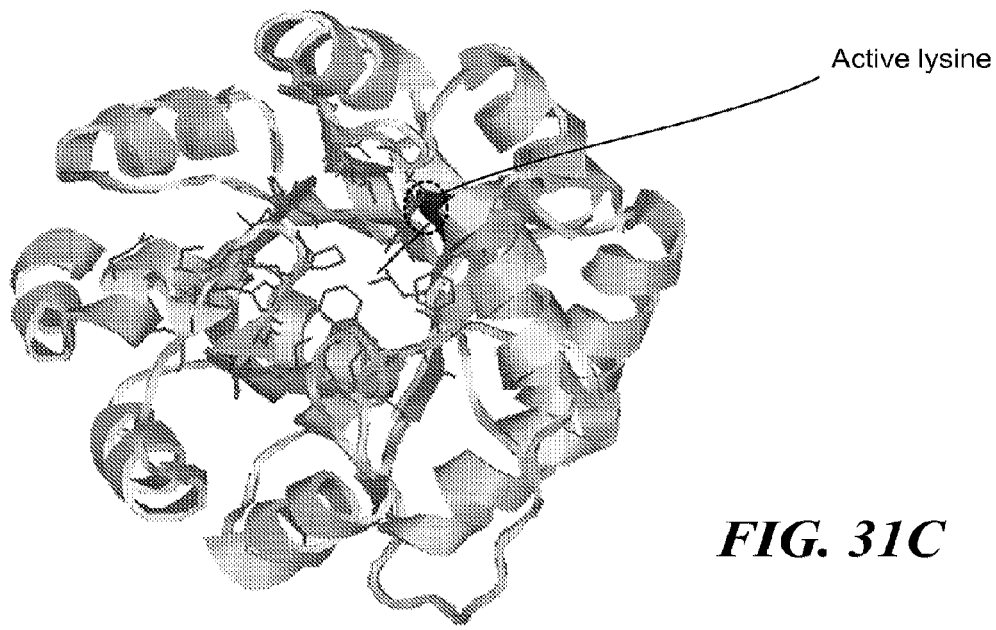
FIG. 31C

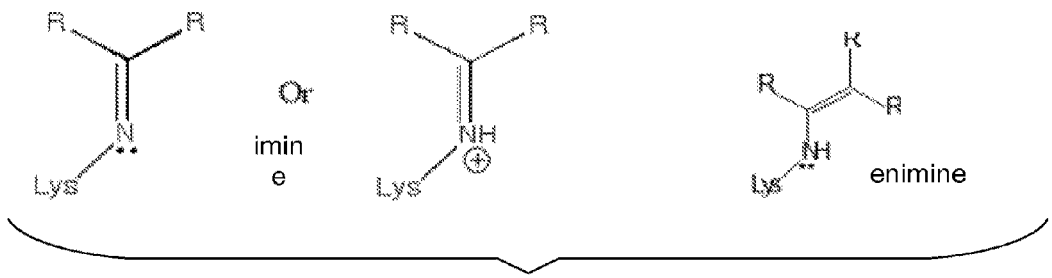
FIG. 32 (PRIOR ART)
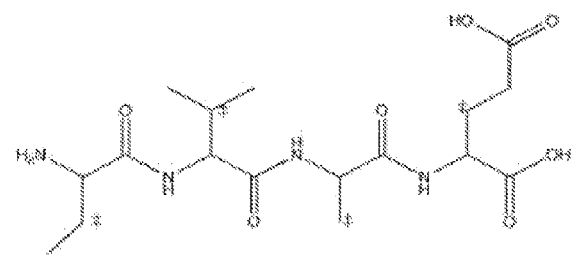
All positions denoted by a double dagger are C-Beta (amino acid beta carbons)
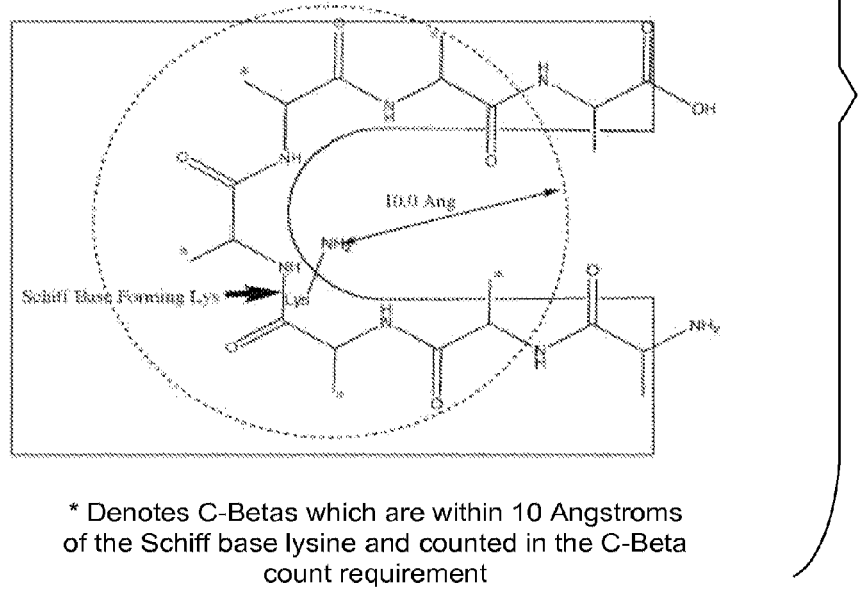
\* Denotes C-Betas which are within 10 Angstroms of the Schiff base lysine and counted in the C-Beta count requirement
FIG. 33

SEQUENCE LISTING

```
<160> NUMBER OF SEQ ID NOS: 31

<210> SEQ ID NO 1
<211> LENGTH: 251
<212> TYPE: PRT
<213> ORGANISM: Artificial Sequence
```

```
<220> FEATURE:
<223> OTHER INFORMATION: SYNTHETIC ALDOLASE - referred to in
      specification as RA31

<400> SEQUENCE: 1

Arg Arg Leu Trp Glu Ala Val Glu Ala Lys Lys Asp Ile Leu Glu
1               5                   10                  15

Ile Asp Gly Glu Asn Leu Ile Val Gln Arg Arg Asn His Arg Phe Leu
                20                  25                  30

Glu Val Leu Ser Gly Lys Glu Arg Val Lys Ile Ile Ala Gln Phe Ser
            35                  40                  45

Lys Ala Ser Pro Ser Ala Gly Asp Ile Asn Ala Asp Ala Ser Leu Glu
50                  55                  60

Asp Phe Ile Arg Met Tyr Asp Glu Leu Ala Asp Ala Ile Leu Ile Asp
65                  70                  75                  80

Thr Ala Lys His Tyr Phe Lys Gly Asp Pro Ala Phe Val Arg Ala Ala
                85                  90                  95

Arg Asn Leu Thr Cys Arg Pro Ile Leu Ala His Asp Ile Tyr Ile Asp
            100                 105                 110

Thr Val Gln Val Lys Leu Ala Ser Ser Val Gly Ala Asp Ala Ile Val
        115                 120                 125

Ile Leu Ala Arg Ile Leu Thr Ala Glu Gln Ile Lys Glu Ile Tyr Glu
130                 135                 140

Ala Ala Glu Glu Leu Gly Met Asp Ser Leu Val Leu His Ser Arg
145                 150                 155                 160

Glu Asp Leu Glu Lys Val Phe Ser Val Ile Arg Pro Lys Ile Ile Gly
                165                 170                 175

Ile Lys Thr Arg Asp Leu Asp Thr Phe Glu Ile Lys Lys Asn Val Leu
            180                 185                 190

Trp Glu Leu Leu Pro Leu Val Pro Asp Asp Thr Val Val Ala Leu
        195                 200                 205

Trp Gly Ile Lys Asp Pro Arg Glu Leu Lys Asp Leu Arg Gly Lys Val
210                 215                 220

Asn Ala Val Leu Val Gly Thr Ser Ile Met Lys Ala Glu Asn Pro Arg
225                 230                 235                 240

Arg Phe Leu Glu Glu Met Arg Ala Trp Ser Glu
                245                 250

<210> SEQ ID NO 2
<211> LENGTH: 251
<212> TYPE: PRT
<213> ORGANISM: Artificial Sequence
<220> FEATURE:
<223> OTHER INFORMATION: SYNTHETIC ALDOLASE - referred to in
      specifcation as RA32

<400> SEQUENCE: 2

Arg Arg Leu Trp Glu Ile Val Glu Ala Lys Lys Asp Ile Leu Glu
1               5                   10                  15

Ile Asp Gly Glu Asn Leu Ile Val Gln Arg Arg Asn His Arg Phe Leu
                20                  25                  30

Glu Val Leu Ser Gly Lys Glu Arg Val Lys Ile Ile Ala Gln Phe Ser
            35                  40                  45

Lys Ala Ser Pro Ser Ala Gly Asp Ile Asn Ala Asp Ala Ser Leu Glu
50                  55                  60

Asp Phe Ile Arg Met Tyr Asp Glu Leu Ala Asp Ala Ile Thr Ile Asp
65                  70                  75                  80
```

```
Thr Glu Lys His Tyr Phe Lys Gly Asp Pro Ala Phe Val Arg Ala Ala
                85                  90                  95

Arg Asn Leu Thr Cys Arg Pro Ile Val Ala His Asp Phe Tyr Ile Asp
            100                 105                 110

Thr Val Gln Val Lys Leu Ala Ser Ser Val Gly Ala Asp Ala Ile Val
        115                 120                 125

Ile Ile Ala Arg Ile Leu Thr Ala Glu Gln Ile Lys Glu Ile Tyr Glu
130                 135                 140

Ala Ala Glu Glu Leu Gly Met Asp Ser Leu Val Val His Ser Arg
145                 150                 155                 160

Glu Asp Leu Glu Lys Val Phe Ser Val Ile Arg Pro Lys Ile Ile Lys
                165                 170                 175

Ile Ala Thr Arg Asp Ala Asp Thr Phe Glu Ile Lys Lys Asn Val Leu
            180                 185                 190

Trp Glu Leu Leu Pro Leu Val Pro Asp Asp Thr Val Val Ala Phe
        195                 200                 205

Ser Gly Ile Lys Asp Pro Arg Glu Leu Lys Asp Leu Arg Gly Lys Val
210                 215                 220

Asn Ala Val Ser Val Gly Thr Ser Ile Met Lys Ala Glu Asn Pro Arg
225                 230                 235                 240

Arg Phe Leu Glu Glu Met Arg Ala Trp Ser Glu
                245                 250

<210> SEQ ID NO 3
<211> LENGTH: 251
<212> TYPE: PRT
<213> ORGANISM: Artificial Sequence
<220> FEATURE:
<223> OTHER INFORMATION: SYNTHETIC ALDOLASE - referred to in
      specification as RA33

<400> SEQUENCE: 3

Arg Arg Leu Trp Glu Ile Val Glu Ala Lys Lys Asp Ile Leu Glu
1               5                   10                  15

Ile Asp Gly Glu Asn Leu Ile Val Gln Arg Arg Asn His Arg Phe Leu
            20                  25                  30

Glu Val Leu Ser Gly Lys Glu Arg Val Lys Ile Ile Ala Gln Phe Ser
        35                  40                  45

Lys Ala Ser Pro Ser Ala Gly Asp Ile Asn Ala Asp Ala Ser Leu Glu
    50                  55                  60

Asp Phe Ile Arg Met Tyr Asp Glu Leu Ala Asp Ala Ile Thr Ile Asp
65                  70                  75                  80

Thr Ala Lys His Tyr Ala Lys Gly Asp Pro Ala Phe Val Arg Ala Ala
                85                  90                  95

Arg Asn Leu Thr Cys Arg Pro Ile Val Ala His Asp Phe Tyr Ile Asp
            100                 105                 110

Thr Val Gln Val Lys Leu Ala Ser Ser Val Gly Ala Asp Ala Ile Leu
        115                 120                 125

Ile Ile Ala Arg Ile Leu Thr Ala Glu Gln Ile Lys Glu Ile Tyr Glu
130                 135                 140

Ala Ala Glu Glu Leu Gly Met Asp Ser Val Val Val His Ser Arg
145                 150                 155                 160

Glu Asp Leu Glu Lys Val Phe Ser Val Ile Arg Pro Lys Ile Ile Lys
                165                 170                 175

Ile Ala Thr Arg Asp Ala Asp Thr Phe Glu Ile Lys Lys Asn Val Leu
```

```
                    180                 185                 190

Trp Glu Leu Leu Pro Leu Val Pro Asp Asp Thr Val Val Ala Leu
            195                 200                 205

Ser Gly Ile Lys Asp Pro Arg Glu Leu Lys Asp Leu Arg Gly Lys Val
            210                 215                 220

Asn Ala Val Ser Val Gly Thr Ser Ile Met Lys Ala Glu Asn Pro Arg
225                 230                 235                 240

Arg Phe Leu Glu Glu Met Arg Ala Trp Ser Glu
                245                 250

<210> SEQ ID NO 4
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA22

<400> SEQUENCE: 4

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Asp Arg Lys Ser Pro Ser Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Thr Thr Glu Glu Lys Tyr Phe Asn Gly Ser Tyr Glu Thr Leu Arg
                85                  90                  95

Lys Ile Ala Ser Ser Val Ser Ile Pro Ile Leu Met Ala Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
    130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Val Ser Ala Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ala Phe Gly Ile Ser Glu Arg Asn Glu Ile Glu Glu Leu Arg Lys Leu
    210                 215                 220

Gly Val Asn Ala Phe Ser Ile His Ser Ser Leu Met Arg Asn Pro Glu
225                 230                 235                 240

Lys Ile Lys Glu Phe Ile Leu
                245

<210> SEQ ID NO 5
<211> LENGTH: 247
<212> TYPE: PRT
<213> ORGANISM: Artificial Sequence
<220> FEATURE:
```

<223> OTHER INFORMATION: SYNTHETIC ALDOLASE - referred to in
      specification as RA34

<400> SEQUENCE: 5

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Leu Tyr Met Arg Lys Ser Pro Trp Gly Leu Asp Val Glu Arg Asp
50                  55                  60

Pro Ile Glu Tyr Ser Lys Phe Met Glu Arg Tyr Ala Val Gly Leu Ser
65                  70                  75                  80

Ile Thr Thr Glu Glu Lys Tyr Ala Asn Gly Ser Tyr Glu Thr Leu Arg
                85                  90                  95

Lys Ile Ala Ser Ser Val Ser Ile Pro Ile Leu Met Ala Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Val Ser Arg Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Tyr Gly Ile Ser Glu Arg Asn Glu Ile Glu Glu Leu Arg Lys Leu
210                 215                 220

Gly Val Asn Ala Phe Ser Ile Gly Ser Ser Leu Met Arg Asn Pro Glu
225                 230                 235                 240

Lys Ile Lys Glu Phe Ile Leu
                245

<210> SEQ ID NO 6
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA35

<400> SEQUENCE: 6

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Ile Arg Lys Ser Pro Ser Gly Leu Asp Val Glu Arg Asp
50                  55                  60

Pro Ile Glu Tyr Ser Lys Phe Met Glu Arg Tyr Ala Val Gly Leu Ala
65                  70                  75                  80

```
Ile Thr Thr Glu Glu Lys Tyr Gly Asn Gly Ser Tyr Glu Thr Leu Arg
                85                  90                  95

Lys Ile Ala Ser Ser Val Ser Ile Pro Ile Leu Met Ala Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Ile Ser Arg Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Tyr Gly Ile Ser Glu Arg Asn Glu Ile Glu Leu Arg Lys Leu
210                 215                 220

Gly Val Asn Ala Phe Ser Ile Tyr Ser Ser Leu Met Arg Asn Pro Glu
225                 230                 235                 240

Lys Ile Lys Glu Phe Ile Leu
                245

<210> SEQ ID NO 7
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA36

<400> SEQUENCE: 7

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Val Arg Lys Gly Pro Trp Gly Leu Asp Val Glu Arg Asp
    50                  55                  60

Pro Ile Glu Tyr Ser Lys Phe Met Glu Arg Tyr Ala Val Gly Leu Ala
65                  70                  75                  80

Ile Ala Thr Glu Glu Lys Tyr Trp Asn Gly Ser Tyr Glu Thr Leu Arg
                85                  90                  95

Lys Ile Ala Ser Ser Val Ser Ile Pro Ile Leu Met Thr Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Val Ser Ala Asp Trp Glu Thr Leu Glu Ile Asn Lys Glu Asn
            180                 185                 190
```

```
Gln Arg Lys Leu Ile Ser Met Ile Pro Ser Asn Val Val Lys Val Ala
        195                 200                 205

Ser Phe Gly Ile Ser Glu Arg Asn Glu Ile Glu Glu Leu Arg Lys Leu
    210                 215                 220

Gly Val Asn Ala Phe Ala Ile Tyr Ser Ser Leu Met Arg Asn Pro Glu
225                 230                 235                 240

Lys Ile Lys Glu Phe Ile Leu
                245

<210> SEQ ID NO 8
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA39

<400> SEQUENCE: 8

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Ser Arg Lys Ser Pro Thr Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Leu Thr Glu Glu Lys Tyr Phe Asn Gly Ser Tyr Glu Thr Leu Arg
                85                  90                  95

Lys Ile Ala Ser Ser Val Ser Ile Pro Ile Leu Met Thr Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
    130                 135                 140

Leu Glu Tyr Ala Arg Ser Tyr Gly Met Glu Pro Leu Ile Val Ile Thr
145                 150                 155                 160

Asp Glu Asn Asp Leu Asp Ile Ala Leu Arg Ile Gly Ala Arg Phe Ile
                165                 170                 175

Lys Ile Leu Ser Arg Asp Trp Glu Thr Gly Glu Ile Asn Lys Glu Asn
            180                 185                 190

Gln Arg Lys Leu Ile Ser Met Ile Pro Ser Asn Val Val Lys Val Ala
        195                 200                 205

Ser Ser Gly Ile Ser Glu Arg Asn Glu Ile Glu Glu Leu Arg Lys Leu
    210                 215                 220

Gly Val Asn Ala Phe Ser Ile Tyr Ser Ser Leu Met Arg Asn Pro Glu
225                 230                 235                 240

Lys Ile Lys Glu Phe Ile Leu
                245

<210> SEQ ID NO 9
<211> LENGTH: 247
<212> TYPE: PRT
<213> ORGANISM: Artificial Sequence
<220> FEATURE:
<223> OTHER INFORMATION: SYNTHETIC ALDOLASE - referred to in
``` specification as RA41

<400> SEQUENCE: 9

Pro Arg Tyr Leu Lys Gly Trp Ala Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Val Tyr Ser Arg Lys Ser Pro Ser Gly Leu Asp Val Glu Arg Asp
    50                  55                  60

Pro Ile Glu Tyr Ser Lys Phe Met Glu Arg Tyr Ala Val Gly Leu Thr
65                  70                  75                  80

Ile Tyr Thr Glu Glu Lys Tyr Trp Asn Gly Ser Tyr Glu Thr Leu Arg
                85                  90                  95

Lys Ile Ala Ser Ser Val Ser Ile Pro Ile Leu Met Ala Asp Leu Ile
            100                 105                 110

Val Lys Glu Ser Gln Ile Asp Asp Ala Tyr Asn Leu Gly Ala Asp Thr
        115                 120                 125

Val Val Leu Ile Val Pro Ile Leu Thr Glu Arg Glu Leu Glu Ser Leu
    130                 135                 140

Leu Glu Tyr Ala Arg Ser Tyr Gly Met Glu Pro Leu Ile Val Ile Val
145                 150                 155                 160

Asp Glu Asn Asp Leu Asp Ile Ala Leu Arg Ile Gly Ala Arg Phe Ile
                165                 170                 175

Lys Ile Lys Ser Arg Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Ser Gly Ile Ser Glu Arg Asn Glu Ile Glu Glu Leu Arg Lys Leu
    210                 215                 220

Gly Val Asn Ala Phe Ile Ile Gly Ser Ser Leu Met Arg Asn Pro Glu
225                 230                 235                 240

Lys Ile Lys Glu Phe Ile Leu
                245

<210> SEQ ID NO 10
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA47

<400> SEQUENCE: 10

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Met Arg Lys Ser Pro Trp Gly Leu Asp Val Glu Arg Asp
    50                  55                  60

Pro Ile Glu Tyr Ser Lys Phe Met Glu Arg Tyr Ala Val Gly Leu Ala
65                  70                  75                  80

Ile Thr Thr Glu Glu Lys Tyr Ala Asn Gly Ser Tyr Glu Thr Leu Arg

```
                85                  90                  95
Lys Ile Ala Ser Ser Val Ser Ile Pro Ile Leu Met Ala Asp Phe Ile
                100                 105                 110
Val Lys Glu Ser Gln Ile Asp Asp Ala Tyr Asn Leu Gly Ala Asp Thr
                115                 120                 125
Val Ala Leu Ile Val Lys Ile Leu Thr Glu Arg Glu Leu Glu Ser Leu
            130                 135                 140
Leu Glu Tyr Ala Arg Ser Tyr Gly Met Glu Pro Leu Ile Lys Ile Asn
145                 150                 155                 160
Asp Glu Asn Asp Leu Asp Ile Ala Leu Arg Ile Gly Ala Arg Phe Ile
                165                 170                 175
Gly Ile Val Ser Arg Asp Trp Glu Thr Leu Glu Ile Asn Lys Glu Asn
                180                 185                 190
Gln Arg Lys Leu Ile Ser Met Ile Pro Ser Asn Val Val Lys Val Ala
                195                 200                 205
Ser Tyr Gly Ile Ser Glu Arg Asn Glu Ile Glu Glu Leu Arg Lys Leu
            210                 215                 220
Gly Val Asn Ala Phe Ser Ile Tyr Ser Ser Leu Met Arg Asn Pro Glu
225                 230                 235                 240
Lys Ile Lys Glu Phe Ile Leu
                245

<210> SEQ ID NO 11
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA6

<400> SEQUENCE: 11

Pro Arg Tyr Leu Lys Gly Trp Leu Lys Asp Val Val Gln Leu Ser Leu
1               5                   10                  15
Arg Arg Pro Ser Phe Arg Ala Ser Arg Gln Arg Pro Ile Ile Ser Leu
                20                  25                  30
Asn Glu Arg Ile Leu Glu Phe Asn Lys Arg Asn Ile Thr Ala Ile Ile
            35                  40                  45
Ala Met Tyr Ser Arg Lys Ser Pro Trp Gly Leu Asp Val Glu Arg Asp
        50                  55                  60
Pro Ile Glu Tyr Ser Lys Phe Met Glu Arg Tyr Ala Val Gly Leu Val
65                  70                  75                  80
Ile Leu Thr Glu Glu Lys Tyr Ala Asn Gly Ser Tyr Glu Thr Leu Arg
                85                  90                  95
Lys Ile Ala Ser Ser Val Ser Ile Pro Ile Leu Met Val Asp Trp Ile
                100                 105                 110
Val Lys Glu Ser Gln Ile Asp Asp Ala Tyr Asn Leu Gly Ala Asp Thr
                115                 120                 125
Val Val Leu Val Val Lys Ile Leu Thr Glu Arg Glu Leu Glu Ser Leu
            130                 135                 140
Leu Glu Tyr Ala Arg Ser Tyr Gly Met Glu Pro Leu Ile Val Ile Asn
145                 150                 155                 160
Asp Glu Asn Asp Leu Asp Ile Ala Leu Arg Ile Gly Ala Arg Phe Ile
                165                 170                 175
Lys Ile Ser Ser Glu Asp Leu Glu Thr Leu Glu Ile Asn Lys Glu Asn
                180                 185                 190
```

```
Gln Arg Lys Leu Ile Ser Met Ile Pro Ser Asn Val Val Lys Val Ala
            195                 200                 205

Ala His Gly Ile Ser Glu Arg Asn Glu Ile Glu Glu Leu Arg Lys Leu
210                 215                 220

Gly Val Asn Ala Phe Leu Ile Gly Ser Ser Leu Met Arg Asn Pro Glu
225                 230                 235                 240

Lys Ile Lys Glu Phe Ile Leu
            245

<210> SEQ ID NO 12
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA42

<400> SEQUENCE: 12

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Leu Tyr Ser Arg Lys Ser Pro Trp Gly Leu Asp Val Glu Arg Asp
50                  55                  60

Pro Ile Glu Tyr Ser Lys Phe Met Glu Arg Tyr Ala Val Gly Leu Val
65                  70                  75                  80

Ile Ala Thr Glu Glu Lys Tyr Thr Asn Gly Ser Tyr Glu Thr Leu Arg
                85                  90                  95

Lys Ile Ala Ser Ser Val Ser Ile Pro Ile Leu Met Trp Asp Phe Ile
            100                 105                 110

Val Lys Glu Ser Gln Ile Asp Asp Ala Tyr Asn Leu Gly Ala Asp Thr
        115                 120                 125

Val Leu Leu Ile Val Lys Ile Leu Thr Glu Arg Glu Leu Glu Ser Leu
130                 135                 140

Leu Glu Tyr Ala Arg Ser Tyr Gly Met Glu Pro Leu Ile Val Ile Asn
145                 150                 155                 160

Asp Glu Asn Asp Leu Asp Ile Ala Leu Arg Ile Gly Ala Arg Phe Ile
                165                 170                 175

Lys Ile Ser Ser Met Asp Tyr Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Ser Gly Ile Ser Glu Arg Asn Glu Ile Glu Glu Leu Arg Lys Leu
    210                 215                 220

Gly Val Asn Ala Phe Val Ile Tyr Ser Ser Leu Met Arg Asn Pro Glu
225                 230                 235                 240

Lys Ile Lys Glu Phe Ile Leu
            245

<210> SEQ ID NO 13
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA45
```

<400> SEQUENCE: 13

```
Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Leu Tyr Ser Arg Lys Ser Pro Trp Gly Leu Asp Val Glu Arg Asp
    50                  55                  60

Pro Ile Glu Tyr Ser Lys Phe Met Glu Arg Tyr Ala Val Gly Leu Val
65                  70                  75                  80

Ile Ala Thr Glu Glu Lys Tyr Thr Asn Gly Ser Tyr Glu Thr Leu Arg
                85                  90                  95

Lys Ile Ala Ser Ser Val Ser Ile Pro Ile Leu Met Trp Asp Phe Ile
            100                 105                 110

Val Lys Glu Ser Gln Ile Asp Asp Ala Tyr Asn Leu Gly Ala Asp Thr
        115                 120                 125

Val Leu Leu Ile Val Lys Ile Leu Thr Glu Arg Glu Leu Glu Ser Leu
    130                 135                 140

Leu Glu Tyr Ala Arg Ser Tyr Gly Met Glu Pro Leu Ile Val Ile Asn
145                 150                 155                 160

Asp Glu Asn Asp Leu Asp Ile Ala Leu Arg Ile Gly Ala Arg Phe Ile
                165                 170                 175

Lys Ile Ser Ser Met Asp Tyr Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Ser Gly Ile Ser Glu Arg Asn Glu Ile Glu Glu Leu Arg Lys Leu
    210                 215                 220

Gly Val Asn Ala Phe Val Ile Tyr Ser Ser Leu Met Arg Asn Pro Glu
225                 230                 235                 240

Lys Ile Lys Glu Phe Ile Leu
                245
```

<210> SEQ ID NO 14
<211> LENGTH: 247
<212> TYPE: PRT
<213> ORGANISM: Artificial Sequence
<220> FEATURE:
<223> OTHER INFORMATION: SYNTHETIC ALDOLASE - referred to in specification as RA46

<400> SEQUENCE: 14

```
Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Val Tyr Ser Arg Lys Ser Pro Ser Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Tyr Thr Glu Glu Lys Tyr Trp Asn Gly Ser Tyr Glu Thr Leu Arg
                85                  90                  95
```

```
Lys Ile Ala Ser Ser Val Ser Ile Pro Ile Leu Met Val Asp Leu Ile
                100                 105                 110

Val Lys Glu Ser Gln Ile Asp Asp Ala Tyr Asn Leu Gly Ala Asp Thr
            115                 120                 125

Val Val Leu Ile Val Ser Ile Leu Thr Glu Arg Glu Leu Glu Ser Leu
130                 135                 140

Leu Glu Tyr Ala Arg Ser Tyr Gly Met Glu Pro Val Ile Val Ile Asn
145                 150                 155                 160

Asp Glu Asn Asp Leu Asp Ile Ala Leu Arg Ile Gly Ala Arg Phe Ile
                165                 170                 175

Leu Ile Lys Ser Arg Asp Leu Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Trp Gly Ile Ser Glu Arg Asn Glu Ile Glu Glu Leu Arg Lys Leu
    210                 215                 220

Gly Val Asn Ala Phe Leu Ile Gly Ser Ser Leu Met Arg Asn Pro Glu
225                 230                 235                 240

Lys Ile Lys Glu Phe Ile Leu
                245

<210> SEQ ID NO 15
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA48

<400> SEQUENCE: 15

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Met Tyr Ser Arg Lys Ser Pro Leu Gly Leu Asp Val Glu Arg Asp
    50                  55                  60

Pro Ile Glu Tyr Ser Lys Phe Met Glu Arg Tyr Ala Val Gly Leu Ala
65                  70                  75                  80

Ile Phe Thr Glu Glu Lys Tyr Trp Asn Gly Ser Tyr Glu Thr Leu Arg
                85                  90                  95

Lys Ile Ala Ser Ser Val Ser Ile Pro Ile Leu Met Leu Asp Phe Ile
                100                 105                 110

Val Lys Glu Ser Gln Ile Asp Asp Ala Tyr Asn Leu Gly Ala Asp Thr
            115                 120                 125

Val Lys Leu Ser Val Leu Ile Leu Thr Glu Arg Glu Leu Glu Ser Leu
130                 135                 140

Leu Glu Tyr Ala Arg Ser Tyr Gly Met Glu Pro Leu Ile Ser Ile Tyr
145                 150                 155                 160

Asp Glu Asn Asp Leu Asp Ile Ala Leu Arg Ile Gly Ala Arg Phe Ile
                165                 170                 175

Leu Ile Val Ser Arg Asp Pro Glu Thr Leu Glu Ile Asn Lys Glu Asn
            180                 185                 190

Gln Arg Lys Leu Ile Ser Met Ile Pro Ser Asn Val Val Lys Val Ala
```

```
                195                 200                 205
Leu Ser Gly Ile Ser Glu Arg Asn Glu Ile Glu Glu Leu Arg Lys Leu
    210                 215                 220
Gly Val Asn Ala Phe Leu Ile Gly Ser Ser Leu Met Arg Asn Pro Glu
225                 230                 235                 240
Lys Ile Lys Glu Phe Ile Leu
                245
```

<210> SEQ ID NO 16
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA49

<400> SEQUENCE: 16

```
Pro Arg Tyr Leu Lys Gly Trp Leu Lys Asp Val Val Gln Leu Ser Leu
1               5                   10                  15
Arg Arg Pro Ser Phe Arg Ala Ser Arg Gln Arg Pro Ile Ile Ser Leu
                20                  25                  30
Asn Glu Arg Ile Leu Glu Phe Asn Lys Arg Asn Ile Thr Ala Ile Ile
            35                  40                  45
Ala Met Tyr Ser Arg Lys Ser Pro Trp Gly Leu Asp Val Glu Arg Asp
        50                  55                  60
Pro Ile Glu Tyr Ser Lys Phe Met Glu Arg Tyr Ala Val Gly Leu Val
65                  70                  75                  80
Ile Leu Thr Gly Glu Lys Tyr Ala Asn Gly Ser Tyr Glu Thr Leu Arg
                85                  90                  95
Lys Ile Ala Ser Ser Val Ser Ile Pro Ile Leu Met Val Asp Trp Ile
            100                 105                 110
Val Lys Glu Ser Gln Ile Asp Asp Ala Tyr Asn Leu Gly Ala Asp Thr
        115                 120                 125
Val Val Leu His Val Lys Ile Leu Thr Glu Arg Glu Leu Glu Ser Leu
130                 135                 140
Leu Glu Tyr Ala Arg Ser Tyr Gly Met Glu Pro Leu Ile Thr Ile Asn
145                 150                 155                 160
Asp Glu Asn Asp Leu Asp Ile Ala Leu Arg Ile Gly Ala Arg Phe Ile
                165                 170                 175
Lys Ile Ser Ser Arg Asp His Glu Thr Leu Glu Ile Asn Lys Glu Asn
            180                 185                 190
Gln Arg Lys Leu Ile Ser Met Ile Pro Ser Asn Val Val Lys Val Ala
        195                 200                 205
Ala Leu Gly Ile Ser Glu Arg Asn Glu Ile Glu Glu Leu Arg Lys Leu
    210                 215                 220
Gly Val Asn Ala Phe Ile Ile Gly Ser Ser Leu Met Arg Asn Pro Glu
225                 230                 235                 240
Lys Ile Lys Glu Phe Ile Leu
                245
```

<210> SEQ ID NO 17
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA55

<400> SEQUENCE: 17

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Tyr Tyr Thr Arg Lys Ser Pro Trp Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Leu Thr Glu Glu Lys Tyr Phe Asn Gly Ser Tyr Glu Thr Leu Arg
                85                  90                  95

Lys Ile Ala Ser Ser Val Ser Ile Pro Ile Leu Met Thr Asp Phe Ile
            100                 105                 110

Val Lys Glu Ser Gln Ile Asp Asp Ala Tyr Asn Leu Gly Ala Asp Thr
        115                 120                 125

Val Ala Leu Ile Val Lys Ile Leu Thr Glu Arg Glu Leu Glu Ser Leu
    130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Val Ser Arg Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Ser Gly Ile Ser Glu Arg Asn Glu Ile Glu Leu Arg Lys Leu
    210                 215                 220

Gly Val Asn Ala Phe Ser Ile Val Ile Ser Leu Met Arg Asn Pro Glu
225                 230                 235                 240

Lys Ile Lys Glu Phe Ile Leu
                245

<210> SEQ ID NO 18
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA56

<400> SEQUENCE: 18

Pro Arg Tyr Leu Lys Gly Arg Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Ile Arg Lys His Pro Ser Gly Leu Asp Val Glu Arg Asp
    50                  55                  60

Pro Ile Glu Tyr Ser Lys Phe Met Glu Arg Tyr Ala Val Gly Leu Ala
65                  70                  75                  80

Ile Tyr Thr Glu Glu Lys Tyr Thr Asn Gly Ser Tyr Glu Thr Leu Arg
                85                  90                  95

```
Lys Ile Ala Ser Ser Val Ser Ile Pro Ile Leu Met Ile Asp Phe Ile
            100                 105                 110

Val Lys Glu Ser Gln Ile Asp Asp Ala Tyr Asn Leu Gly Ala Asp Thr
            115                 120                 125

Val Val Leu Ile Val Lys Ile Leu Thr Glu Arg Glu Leu Glu Ser Leu
        130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile His Ser Arg Asp Trp Glu Thr Phe Glu Ile Asn Lys Glu Asn
            180                 185                 190

Gln Arg Lys Leu Ile Ser Met Ile Pro Ser Asn Val Val Lys Val Ala
        195                 200                 205

Thr Ser Gly Ile Ser Glu Arg Asn Glu Ile Glu Glu Leu Arg Lys Leu
    210                 215                 220

Gly Val Asn Ala Phe Ser Ile Tyr Ser Ser Leu Met Arg Asn Pro Glu
225                 230                 235                 240

Lys Ile Lys Glu Phe Ile Leu
                245

<210> SEQ ID NO 19
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA57

<400> SEQUENCE: 19

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Gly Tyr Met Arg Lys Ser Pro Ser Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Trp Thr Glu Glu Lys Tyr Ser Asn Gly Ser Tyr Glu Thr Leu Arg
                85                  90                  95

Lys Ile Ala Ser Ser Val Ser Ile Pro Ile Leu Met Leu Asp Phe Ile
            100                 105                 110

Val Lys Glu Ser Gln Ile Asp Asp Ala Tyr Asn Leu Gly Ala Asp Thr
            115                 120                 125

Val Val Leu Ile Val Lys Ile Leu Thr Glu Arg Glu Leu Glu Ser Leu
        130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Gly Ile Val Ser Arg Asp Trp Glu Thr Leu Glu Ile Asn Lys Glu Asn
            180                 185                 190

Gln Arg Lys Leu Ile Ser Met Ile Pro Ser Asn Val Val Lys Val Ala
        195                 200                 205
```

```
Ser His Gly Ile Ser Glu Arg Asn Glu Ile Glu Glu Leu Arg Lys Leu
    210                 215                 220

Gly Val Asn Ala Phe Thr Ile Tyr Ser Ser Leu Met Arg Asn Pro Glu
225                 230                 235                 240

Lys Ile Lys Glu Phe Ile Leu
                245

<210> SEQ ID NO 20
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA63

<400> SEQUENCE: 20

Pro Arg Tyr Leu Lys Gly Trp Leu Lys Asp Val Val Gln Leu Ser Leu
1               5                   10                  15

Arg Arg Pro Ser Phe Arg Ala Ser Arg Gln Pro Ile Ile Ser Leu
            20                  25                  30

Asn Glu Arg Ile Leu Glu Phe Asn Lys Arg Asn Ile Thr Ala Ile Ile
            35                  40                  45

Ala Leu Tyr Met Arg Lys Ser Pro Trp Gly Leu Asp Val Glu Arg Asp
50                  55                  60

Pro Ile Glu Tyr Ser Lys Phe Met Glu Arg Tyr Ala Val Gly Leu Ser
65                  70                  75                  80

Ile Leu Thr Glu Glu Lys Tyr Phe Asn Gly Ser Tyr Glu Thr Leu Arg
                85                  90                  95

Lys Ile Ala Ser Ser Val Ser Ile Pro Ile Leu Met His Asp Phe Ile
                100                 105                 110

Val Lys Glu Ser Gln Ile Asp Asp Ala Tyr Asn Leu Gly Ala Asp Thr
            115                 120                 125

Val Lys Leu Ser Val Tyr Ile Leu Thr Glu Arg Glu Leu Glu Ser Leu
            130                 135                 140

Leu Glu Tyr Ala Arg Ser Tyr Gly Met Glu Pro Leu Ile Ser Ile Asn
145                 150                 155                 160

Asp Glu Asn Asp Leu Asp Ile Ala Leu Arg Ile Gly Ala Arg Phe Ile
                165                 170                 175

Gly Ile Val Ser Arg Asp Pro Glu Thr Leu Glu Ile Asn Lys Glu Asn
                180                 185                 190

Gln Arg Lys Leu Ile Ser Met Ile Pro Ser Asn Val Val Lys Val Ala
            195                 200                 205

Ile Ser Gly Ile Ser Glu Arg Asn Glu Ile Glu Glu Leu Arg Lys Leu
    210                 215                 220

Gly Val Asn Ala Phe Leu Ile Gly Ser Ser Leu Met Arg Asn Pro Glu
225                 230                 235                 240

Lys Ile Lys Glu Phe Ile Leu
                245

<210> SEQ ID NO 21
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA26

<400> SEQUENCE: 21
```

```
Pro Arg Tyr Leu Lys Gly Trp Leu Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Glu Tyr Ser Arg Lys Ser Pro Trp Gly Leu Asp Val Glu Arg Asp
50                  55                  60

Pro Ile Glu Tyr Ser Lys Phe Met Glu Arg Tyr Ala Val Gly Leu Leu
65                  70                  75                  80

Ile Leu Thr Glu Glu Lys Tyr Phe Asn Gly Ser Tyr Glu Thr Leu Arg
                85                  90                  95

Lys Ile Ala Ser Ser Val Ser Ile Pro Ile Leu Met His Asp Phe Ile
            100                 105                 110

Val Lys Glu Ser Gln Ile Asp Asp Ala Tyr Asn Leu Gly Ala Asp Thr
        115                 120                 125

Val Lys Leu Ile Val Lys Ile Leu Thr Glu Arg Glu Leu Glu Ser Leu
130                 135                 140

Leu Glu Tyr Ala Arg Ser Tyr Gly Met Glu Pro Leu Ile Ala Ile His
145                 150                 155                 160

Asp Glu Asn Asp Leu Asp Ile Ala Leu Arg Ile Gly Ala Arg Phe Ile
                165                 170                 175

Gly Ile Ser Ser Arg Asp Pro Glu Thr Leu Glu Ile Asn Lys Glu Asn
            180                 185                 190

Gln Arg Lys Leu Ile Ser Met Ile Pro Ser Asn Val Lys Val Ala
        195                 200                 205

Leu Ser Gly Ile Ser Glu Arg Asn Glu Ile Glu Leu Arg Lys Leu
210                 215                 220

Gly Val Asn Ala Phe Leu Ile Gly Ser Ser Leu Met Arg Asn Pro Glu
225                 230                 235                 240

Lys Ile Lys Glu Phe Ile Leu
                245

<210> SEQ ID NO 22
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA40

<400> SEQUENCE: 22

Pro Arg Tyr Leu Lys Gly Trp Val Lys Asp Val Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Val Tyr Met Arg Lys Ser Pro Ser Gly Leu Asp Val Glu Arg Asp
50                  55                  60

Pro Ile Glu Tyr Ser Lys Phe Met Glu Arg Tyr Ala Val Gly Leu Thr
65                  70                  75                  80

Ile Tyr Thr Glu Glu Lys Tyr Phe Asn Gly Ser Tyr Glu Thr Leu Arg
                85                  90                  95

Lys Ile Ala Ser Ser Val Ser Ile Pro Ile Leu Met Val Asp Phe Ile
```

```
                    100                 105                 110
Val Lys Glu Ser Gln Ile Asp Asp Ala Tyr Asn Leu Gly Ala Asp Thr
            115                 120                 125
Val Val Leu Phe Val Pro Ile Leu Thr Glu Arg Glu Leu Glu Ser Leu
        130                 135                 140
Leu Glu Tyr Ala Arg Ser Tyr Gly Met Glu Pro Leu Ile Val Ile Asn
145                 150                 155                 160
Asp Glu Asn Asp Leu Asp Ile Ala Leu Arg Ile Gly Ala Arg Phe Ile
                165                 170                 175
Lys Ile Leu Ser Ser Asp Val Glu Thr Leu Glu Ile Asn Lys Glu Asn
            180                 185                 190
Gln Arg Lys Leu Ile Ser Met Ile Pro Ser Asn Val Val Lys Val Ala
        195                 200                 205
Ser His Gly Ile Ser Glu Arg Asn Glu Ile Glu Leu Arg Lys Leu
            210                 215                 220
Gly Val Asn Ala Phe Ser Ile Gly Ser Ser Leu Met Arg Asn Pro Glu
225                 230                 235                 240
Lys Ile Lys Glu Phe Ile Leu
                245

<210> SEQ ID NO 23
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA43

<400> SEQUENCE: 23

Pro Arg Tyr Leu Lys Gly Trp Leu Lys Asp Val Val Gln Leu Ser Leu
1               5                   10                  15
Arg Arg Pro Ser Phe Arg Ala Ser Arg Gln Arg Pro Ile Ile Ser Leu
            20                  25                  30
Asn Glu Arg Ile Leu Glu Phe Asn Lys Arg Asn Ile Thr Ala Ile Ile
        35                  40                  45
Ala Val Tyr Ser Arg Lys Ser Pro Ser Gly Leu Asp Val Glu Arg Asp
    50                  55                  60
Pro Ile Glu Tyr Ser Lys Phe Met Glu Arg Tyr Ala Val Gly Leu Leu
65                  70                  75                  80
Ile Trp Thr Gly Glu Lys Tyr Gly Asn Gly Ser Tyr Glu Thr Leu Arg
                85                  90                  95
Lys Ile Ala Ser Ser Val Ser Ile Pro Ile Leu Met Val Asp Trp Ile
            100                 105                 110
Val Lys Glu Ser Gln Ile Asp Asp Ala Tyr Asn Leu Gly Ala Asp Thr
        115                 120                 125
Val Leu Leu Val Val Lys Ile Leu Thr Glu Arg Glu Leu Glu Ser Leu
    130                 135                 140
Leu Glu Tyr Ala Arg Ser Tyr Gly Met Glu Pro Leu Ile Ser Ile Tyr
145                 150                 155                 160
Asp Glu Asn Asp Leu Asp Ile Ala Leu Arg Ile Gly Ala Arg Phe Ile
                165                 170                 175
Lys Ile Ala Ser Arg Asp Pro Glu Thr Leu Glu Ile Asn Lys Glu Asn
            180                 185                 190
Gln Arg Lys Leu Ile Ser Met Ile Pro Ser Asn Val Val Lys Val Ala
        195                 200                 205
```

```
Ser Ser Gly Ile Ser Glu Arg Asn Glu Ile Glu Glu Leu Arg Lys Leu
    210                 215                 220

Gly Val Asn Ala Phe Val Ile Gly Ser Ser Leu Met Arg Asn Pro Glu
225                 230                 235                 240

Lys Ile Lys Glu Phe Ile Leu
                245

<210> SEQ ID NO 24
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA53

<400> SEQUENCE: 24

Pro Arg Tyr Leu Lys Gly Trp Leu Lys Asp Val Gln Leu Ser Leu
1               5                   10                  15

Arg Arg Pro Ser Phe Arg Ala Ser Arg Gln Arg Pro Ile Ile Ser Leu
            20                  25                  30

Asn Glu Arg Ile Leu Glu Phe Asn Lys Arg Asn Ile Thr Ala Ile Ile
        35                  40                  45

Ala Val Tyr Ser Arg Lys His Pro Ser Gly Leu Asp Val Glu Arg Asp
    50                  55                  60

Pro Ile Glu Tyr Ser Lys Phe Met Glu Arg Tyr Ala Val Gly Leu Ser
65                  70                  75                  80

Ile Tyr Thr Glu Glu Lys Tyr Thr Asn Gly Ser Tyr Glu Thr Leu Arg
                85                  90                  95

Lys Ile Ala Ser Ser Val Ser Ile Pro Ile Leu Met Val Asp Val Ile
            100                 105                 110

Val Lys Glu Ser Gln Ile Asp Asp Ala Tyr Asn Leu Gly Ala Asp Thr
        115                 120                 125

Val Val Leu Ile Val Lys Ile Leu Thr Glu Arg Glu Leu Glu Ser Leu
    130                 135                 140

Leu Glu Tyr Ala Arg Ser Tyr Gly Met Glu Pro Leu Ile Lys Ile Asn
145                 150                 155                 160

Asp Glu Asn Asp Leu Asp Ile Ala Leu Arg Ile Gly Ala Arg Phe Ile
                165                 170                 175

Val Ile Ser Ser Tyr Asp Trp Gly Thr Leu Glu Ile Asn Lys Glu Asn
            180                 185                 190

Gln Arg Lys Leu Ile Ser Met Ile Pro Ser Asn Val Val Lys Val Ala
        195                 200                 205

Ser Gly Gly Ile Ser Glu Arg Asn Glu Ile Glu Glu Leu Arg Lys Leu
    210                 215                 220

Gly Val Asn Ala Phe Ser Ile Gly Ser Ser Leu Met Arg Asn Pro Glu
225                 230                 235                 240

Lys Ile Lys Glu Phe Ile Leu
                245

<210> SEQ ID NO 25
<211> LENGTH: 247
<212> TYPE: PRT
<213> ORGANISM: Artificial Sequence
<220> FEATURE:
<223> OTHER INFORMATION: SYNTHETIC ALDOLASE - referred to in
      specification as RA68

<400> SEQUENCE: 25
```

```
Pro Arg Tyr Leu Lys Gly Trp Leu Lys Asp Val Val Gln Leu Ser Leu
1               5                   10                  15
Arg Arg Pro Ser Phe Arg Ala Ser Arg Gln Pro Ile Ile Ser Leu
            20                  25                  30
Asn Glu Arg Ile Leu Glu Phe Asn Lys Arg Asn Ile Thr Ala Ile Ile
        35                  40                  45
Ala Lys Tyr Lys Arg Lys Ser Pro Thr Gly Leu Asp Val Glu Arg Asp
    50                  55                  60
Pro Ile Glu Tyr Ser Lys Phe Met Glu Arg Tyr Ala Val Gly Leu Ser
65                  70                  75                  80
Ile Ser Thr Glu Glu Lys Tyr His Asn Gly Ser Tyr Glu Thr Leu Arg
                85                  90                  95
Lys Ile Ala Ser Ser Val Ser Ile Pro Ile Leu Met Met Asp Phe Ile
            100                 105                 110
Val Lys Glu Ser Gln Ile Asp Asp Ala Tyr Asn Leu Gly Ala Asp Thr
        115                 120                 125
Val Leu Leu Ile Val Lys Ile Leu Thr Glu Arg Glu Leu Glu Ser Leu
    130                 135                 140
Leu Glu Tyr Ala Arg Ser Tyr Gly Met Glu Pro Leu Ile Leu Ile Asn
145                 150                 155                 160
Asp Glu Asn Asp Leu Asp Ile Ala Leu Arg Ile Gly Ala Arg Phe Ile
                165                 170                 175
Gly Ile Asn Ser Arg Asp Tyr Glu Thr Gly Glu Thr Asn Lys Glu Asn
            180                 185                 190
Gln Arg Lys Leu Ile Ser Met Ile Pro Ser Asn Val Val Lys Val Ala
        195                 200                 205
Ile Tyr Gly Ile Ser Glu Arg Asn Glu Ile Glu Glu Leu Arg Lys Leu
    210                 215                 220
Gly Val Asn Ala Phe Leu Ile Ser Ser Ser Leu Met Arg Asn Pro Glu
225                 230                 235                 240
Lys Ile Lys Glu Phe Ile Leu
                245

<210> SEQ ID NO 26
<211> LENGTH: 253
<212> TYPE: PRT
<213> ORGANISM: Artificial Sequence
<220> FEATURE:
<223> OTHER INFORMATION: SYNTHETIC ALDOLASE - referred to in
      specification as RA17

<400> SEQUENCE: 26

Met Leu Ala Lys Arg Ile Ile Ala Val Leu Leu Val Lys Asp Gly Arg
1               5                   10                  15
Val Val Lys Gly Ser Asn Phe Glu Asn Leu Arg Asp Ser Gly Asp Pro
            20                  25                  30
Val Glu Leu Gly Lys Phe Tyr Ser Glu Ile Gly Ile Asp Glu Leu Ala
        35                  40                  45
Phe Leu Asp Ile Thr Ala Ser Val Glu Lys Arg Lys Thr Met Leu Glu
    50                  55                  60
Leu Val Glu Lys Val Ala Glu Gln Ile Asp Ile Pro Phe Ile Val Gly
65                  70                  75                  80
Gly Gly Ile His Asp Phe Glu Thr Ala Ser Glu Leu Ile Leu Arg Gly
                85                  90                  95
Ala Asp Lys Val Ala Ile Leu Thr Ala Ala Val Glu Asn Pro Ser Leu
            100                 105                 110
```

Ile Thr Gln Ile Ala Gln Thr Phe Gly Ser Gln Ala Val Lys Val Ala
            115                 120                 125

Ile Phe Ala Lys Arg Val Asp Gly Glu Phe Met Val Phe Thr Tyr Ser
130                 135                 140

Gly Lys Lys Asn Thr Gly Ile Leu Leu Arg Asp Trp Val Val Glu Val
145                 150                 155                 160

Glu Lys Arg Gly Ala Gly Glu Ile Ala Leu Val Ser Ile Asp Arg Leu
                165                 170                 175

Gly Thr Lys Ser Gly Tyr Asp Thr Glu Met Ile Arg Phe Val Arg Pro
            180                 185                 190

Leu Thr Thr Leu Pro Ile Ile Ala His Gly Gly Ala Gly Lys Met Glu
            195                 200                 205

His Phe Leu Glu Ala Phe Leu Ala Gly Ala Asp Ala Ala Ala Ala Asp
        210                 215                 220

Ser Val Phe His Phe Arg Glu Ile Asp Val Arg Glu Leu Lys Glu Tyr
225                 230                 235                 240

Leu Lys Lys His Gly Val Asn Val Arg Leu Glu Gly Leu
                245                 250

<210> SEQ ID NO 27
<211> LENGTH: 253
<212> TYPE: PRT
<213> ORGANISM: Artificial Sequence
<220> FEATURE:
<223> OTHER INFORMATION: SYNTHETIC ALDOLASE - referred to in
      specification as RA58

<400> SEQUENCE: 27

Met Leu Ala Lys Arg Ile Ile Ala Ser Leu Tyr Val Lys Asp Gly Arg
1               5                   10                  15

Val Val Lys Gly Ser Asn Phe Glu Asn Leu Arg Asp Ser Gly Asp Pro
            20                  25                  30

Val Glu Leu Gly Lys Phe Tyr Ser Glu Ile Gly Ile Asp Glu Leu Thr
        35                  40                  45

Phe Leu Asp Ile Thr Ala Ser Val Glu Lys Arg Lys Thr Met Leu Glu
50                  55                  60

Leu Val Glu Lys Val Ala Glu Gln Ile Asp Ile Pro Phe Thr Val Gly
65                  70                  75                  80

Gly Gly Ile His Asp Phe Glu Thr Ala Ser Glu Leu Ile Leu Arg Gly
                85                  90                  95

Ala Asp Lys Val Ser Ile His Thr Ala Ala Val Glu Asn Pro Ser Leu
            100                 105                 110

Ile Thr Gln Ile Ala Gln Thr Phe Gly Ser Gln Ala Val Val Val Ser
        115                 120                 125

Ile Trp Ala Lys Arg Val Asp Gly Glu Phe Met Val Phe Thr Tyr Ser
130                 135                 140

Gly Lys Lys Asn Thr Gly Ile Leu Leu Arg Asp Trp Val Val Glu Val
145                 150                 155                 160

Glu Lys Arg Gly Ala Gly Glu Ile Lys Leu Val Ser Ile Asp Arg Trp
                165                 170                 175

Gly Thr Lys Ser Gly Tyr Asp Thr Glu Met Ile Arg Phe Val Arg Pro
            180                 185                 190

Leu Thr Thr Leu Pro Ile Ile Ala His Gly Gly Ala Gly Lys Met Glu
            195                 200                 205

His Phe Leu Glu Ala Phe Leu Ala Gly Ala Asp Ala Ala Leu Ala Ala

Ser Val Phe His Phe Arg Glu Ile Asp Val Arg Glu Leu Lys Glu Tyr
225                 230                 235                 240

Leu Lys Lys His Gly Val Asn Val Arg Leu Glu Gly Leu
            245                 250

<210> SEQ ID NO 28
<211> LENGTH: 197
<212> TYPE: PRT
<213> ORGANISM: Artificial Sequence
<220> FEATURE:
<223> OTHER INFORMATION: SYNTHETIC ALDOLASE - referred to in
      specification as RA59

<400> SEQUENCE: 28

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Thr Phe Val
        35                  40                  45

Ala Gly Lys Gly Trp Ser Thr Gly Gly Arg Arg Thr Val Thr Tyr Asn
50                  55                  60

Ala Ser Phe Asn Pro Ser Gly Tyr Ala Tyr Leu Thr Leu Tyr Gly Trp
65                  70                  75                  80

Thr Arg Asn Pro Leu Val Ser Tyr Tyr Ile Val Glu Ser Trp Gly Thr
            85                  90                  95

Tyr Arg Pro Thr Gly Thr Tyr Lys Gly Thr Val Thr Thr Asp Gly Gly
            100                 105                 110

Thr Tyr Asp Ile Tyr Glu Gly Trp Tyr Tyr Asn Ala Pro Ser Ile Glu
        115                 120                 125

Gly Thr Arg Thr Phe Gln Ile Phe Val Ser Val Arg Gln Gln Lys Arg
130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Lys
                165                 170                 175

Gly Ser Gln Ser Ser Gly Ser Ser Thr Val Ser Ile Ser Glu Gly Gly
            180                 185                 190

Asn Pro Gly Asn Pro
        195

<210> SEQ ID NO 29
<211> LENGTH: 197
<212> TYPE: PRT
<213> ORGANISM: Artificial Sequence
<220> FEATURE:
<223> OTHER INFORMATION: SYNTHETIC ALDOLASE - referred to in
      specification as RA60

<400> SEQUENCE: 29

Asp Thr Thr Ile Thr Gln Asn Gln Thr Gly Tyr Asp Asn Gly Tyr Phe
1               5                   10                  15

Tyr Ser Phe Trp Thr Asp Ala Pro Gly Thr Val Ser Met Thr Leu His
            20                  25                  30

Ser Gly Gly Ser Tyr Ser Thr Ser Trp Arg Asn Thr Gly Trp Phe Lys
        35                  40                  45

Ala Gly Lys Gly Trp Ser Thr Gly Gly Arg Arg Thr Val Thr Tyr Asn

```
                50                  55                  60

Ala Ser Phe Asn Pro Ser Gly Thr Ala Trp Leu Thr Leu Tyr Gly Trp
 65                  70                  75                  80

Thr Arg Asn Pro Leu Val Ser Tyr Ser Ile Val Glu Ser Trp Gly Thr
                 85                  90                  95

Tyr Arg Pro Thr Gly Thr Tyr Lys Gly Thr Val Thr Asp Gly Gly
                100                 105                 110

Thr Tyr Asp Ile Tyr Glu Tyr Trp Trp Tyr Asn Ala Pro Ser Ile Glu
                115                 120                 125

Gly Thr Arg Thr Tyr Gln Ser Phe Trp Ser Val Arg Gln Gln Lys Arg
            130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Val
                165                 170                 175

Gly Val Gln Ser Ser Gly Ser Ser Thr Val Ser Ile Ser Glu Gly Gly
                180                 185                 190

Asn Pro Gly Asn Pro
            195

<210> SEQ ID NO 30
<211> LENGTH: 197
<212> TYPE: PRT
<213> ORGANISM: Artificial Sequence
<220> FEATURE:
<223> OTHER INFORMATION: SYNTHETIC ALDOLASE - referred to in
      specification as RA61

<400> SEQUENCE: 30

Asp Thr Thr Ile Thr Gln Asn Gln Thr Gly Tyr Asp Asn Gly Tyr Phe
 1               5                  10                  15

Tyr Ser Phe Trp Thr Asp Ala Pro Gly Thr Val Ser Met Thr Leu His
                 20                  25                  30

Ser Gly Gly Ser Tyr Ser Thr Ser Trp Arg Asn Thr Gly His Phe Lys
             35                  40                  45

Ala Gly Lys Gly Trp Ser Thr Gly Gly Arg Arg Thr Val Thr Tyr Asn
         50                  55                  60

Ala Ser Phe Asn Pro Ser Gly Ile Ala Tyr Leu Thr Leu Tyr Gly Trp
 65                  70                  75                  80

Thr Arg Asn Pro Leu Val Ser Tyr Leu Ile Val Glu Ser Trp Gly Thr
                 85                  90                  95

Tyr Arg Pro Thr Gly Thr Tyr Lys Gly Thr Val Thr Asp Gly Gly
                100                 105                 110

Thr Tyr Asp Ile Tyr Glu Thr Trp Arg Tyr Asn Ala Pro Ser Ile Glu
                115                 120                 125

Gly Thr Arg Thr Phe Gln Ile Phe Trp Ser Val Arg Gln Gln Lys Arg
            130                 135                 140

Thr Ser Gly Thr Ile Thr Ile Gly Asn His Phe Asp Ala Trp Ala Arg
145                 150                 155                 160

Ala Gly Met Asn Leu Gly Ser His Asp Tyr Gln Ile Met Ala Thr Lys
                165                 170                 175

Gly Trp Gln Ser Ser Gly Ser Ser Thr Val Ser Ile Ser Glu Gly Gly
                180                 185                 190

Asn Pro Gly Asn Pro
            195
```

-continued

```
<210> SEQ ID NO 31
<211> LENGTH: 199
<212> TYPE: PRT
<213> ORGANISM: Artificial Sequence
<220> FEATURE:
<223> OTHER INFORMATION: SYNTHETIC ALDOLASE - referred to in
      specification as RA2832

<400> SEQUENCE: 31

Ala Leu Thr Ser Asn Ala Ser Gly Thr Phe Asp Gly Tyr Tyr Ala
1               5                   10                  15

Leu Trp Lys Asp Thr Gly Asn Thr Thr Met Thr Val Tyr Thr Gln Gly
            20                  25                  30

Arg Phe Ser Cys Gln Trp Ser Asn Ile Asn Phe Ala Ala Phe Arg Thr
            35                  40                  45

Gly Lys Lys Tyr Asn Gln Asn Trp Gln Ser Leu Gly Thr Ile Arg Ile
            50                  55                  60

Thr Tyr Ser Ala Thr Tyr Asn Pro Asn Gly Asn Ser Tyr Leu Cys Ile
65                  70                  75                  80

Phe Gly Trp Ser Thr Asn Pro Leu Val Thr Phe Tyr Ile Val Glu Ser
                85                  90                  95

Trp Gly Asn Trp Arg Pro Pro Gly Ala Thr Ser Leu Gly Gln Val Thr
                100                 105                 110

Ile Asp Gly Gly Thr Tyr Asp Ile Tyr Arg Thr Thr Arg Val Asn Gln
            115                 120                 125

Pro Ser Ile Val Gly Thr Ala Thr Phe Asp Gln Tyr Trp Ser Val Arg
            130                 135                 140

Thr Ser Lys Arg Thr Ser Gly Thr Val Thr Val Thr Asp His Phe Arg
145                 150                 155                 160

Ala Trp Ala Asn Arg Gly Leu Asn Leu Gly Thr Ile Asp Gln Ile Thr
                165                 170                 175

Leu Cys Val Lys Gly Tyr Gln Ser Ser Gly Ser Ala Asn Ile Thr Gln
            180                 185                 190

Asn Thr Phe Ser Gln Ser Ser
            195
```

SYNTHETIC ENZYMES DERIVED FROM COMPUTATIONAL DESIGN

RELATED APPLICATIONS

This application is a continuation of application Ser. No. 12/334,360, filed Dec. 12, 2008, which claims the benefit of Provisional Application No. 61/013,507, filed on Dec. 13, 2007, the disclosures of which are hereby incorporated by reference in their entireties.

GOVERNMENT RIGHTS

This invention was made with government support under grant HR0011-05-1-0044 awarded by the Defense Advanced Research Projects Agency and grant 5F32GM075696 awarded by the National Institutes of Health. The government has certain rights in the invention.

BACKGROUND

Enzymes are among the most efficient, specific, and selective catalysts known. The ability to design efficient enzymes for a broad class of different reactions would transform chemistry, pharmaceuticals, and material sciences.

A major challenge is to create enzymes for chemical transformations not efficiently catalyzed by naturally occurring enzymes, or not catalyzed at all by naturally occurring enzymes. Empirical testing of potential enzyme candidates is time and labor intensive. It would thus be desirable to provide computational tools enabling the efficient design of an enzyme for a particular chemical reaction.

SUMMARY

This application specifically incorporates by reference the disclosures and drawings of each patent application and issued patent identified above as a related application.

Disclosed herein are techniques for computationally designing enzymes and a plurality of enzymes that have thus been successfully designed. These techniques can be used to design variations of naturally occurring enzymes, as well as new enzymes having no natural counterparts.

The techniques are based on first identifying functional reactive sites required to promote the desired reaction. Then, hashing algorithms are used to identify potential protein backbone structures (i.e., scaffolds) capable of supporting the required functional sites. Another algorithm is then employed to computationally develop a plurality of different protein sequences that accommodate the identified scaffolds. Computational ranking is performed, to identify a relatively small number of potential enzyme designs, which can be empirically tested for the desired enzymatic efficiency. Potential candidates can then be further tested using in vitro evolution to identify more efficient variants.

The computational techniques disclosed herein include two unique hashing algorithms that enable active site searches in large numbers of scaffolds. Given a description of a catalytic site encompassing a transition state structure surrounded by protein functional groups in geometrical positions optimal for catalysis, and a set of protein scaffolds, the methods first search for sites in the scaffolds where the active site can be recapitulated.

In the first hashing method, an "inverse rotamer tree" approach is used with a modified version of an existing geometric hashing algorithm (Bachar et al. 1993) to find positions in a set of scaffolds that can support the catalytic site. In the second hashing method, based on an iterative side chain placement and hashing in six-dimensional space, candidate catalytic sites in scaffolds are detected in linear time. Both methods are followed by the design of the pocket using the standard Rosetta design methodology (Rosetta referring to a software package originally developed to study folding of protein structures, to enable the three-dimensional shapes of proteins to be explored computationally). Modules for the original Rosetta program have been developed to enable the design of a protein and the docking of small molecules onto protein structures, as well as rigid-body perturbation of the transition state model (docking).

Significantly, the techniques disclosed herein provide general methods for searching for new active sites in a library of protein scaffolds, and designing the residues surrounding these potential active sites to further stabilize the transition state.

Also disclosed herein are several specific synthetic enzymes that were developed using the computational techniques discussed above. These synthetic enzymes include synthetic aldolases, which can be used to catalyze aldol reaction. These synthetic aldolases are novel and non-obvious because of differences between them and any corresponding naturally occurring aldolase, as discussed below.

All of the synthetic aldolases disclosed herein are based on a scaffold that is not an aldolase.

Some of the synthetic aldolases disclosed herein have active lysines on beta-strand 6, but at a position inward of the terminus of beta-strand 6. All naturally occurring aldolases having an active lysine on beta-strand 6 have the lysine disposed at the terminus of the beta-strand. Such synthetic aldolases include those whose active lysine is either two, four, or six positions inward of the end of beta-strand 6.

Some of the synthetic aldolases disclosed herein have active lysines on either beta-strands 1 or 5, and all naturally occurring aldolases that include an active lysine have the active lysine either on beta-strand 4 or at the end of beta-strand 6.

Some of the synthetic aldolases disclosed herein have active lysines on beta-strand 4 (as does transaldolase), but those that do are based on significantly smaller scaffolds than transaldolase (247 amino acids versus 337 amino acids).

Some of the synthetic aldolases disclosed herein have active lysines and exhibit a fold other than a TIM fold. All naturally occurring aldolases including an active lysine include a TIM fold.

All of the synthetic aldolases disclosed herein have active lysines disposed in a pocket, whose sequences have been designed such that no aspartic acid or glutamic acid side chains are disposed close enough to inhibit the catalytic activity of the epsilon nitrogen of the active lysine. The environment around the lysine in the pocket is instead composed of hydrophobic or non-polar residues such as phenylalanine, alanine, valine, serine, threonine, isoleucine, tyrosine, proline, glycine, methionine, and tryptophan. Thus, one aspect of the concepts disclosed herein encompasses synthetic aldolases designed to exhibit that feature.

The attached Sequence Listing provides details on 31 specific protein sequences defining synthetic aldolases.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 3 is a table of crystal structures of naturally occurring enzymes used for a first benchmark test used to evaluate two different hashing methods (the rotamer tree, and the RosettaMatch methods) that can be used to implement the step of block 14 of FIG. 1;

FIG. 4 is a table of optimal values for geometric parameters used for a second benchmark test used to evaluate a hashing method (RosettaMatch) that can be used to implement the step of block 14 of FIG. 1;

FIG. 5 is a table of exemplary results of the first benchmark test used to evaluate the two different hashing methods;

FIG. 6 shows the energy distribution of native and non-native designed sites. (6A) The distribution of virtual energy and LJ repulsive energy between the TS model and the protein scaffold after minimizing the catalytic residues. (6B) The distribution of the computed catalytic efficacy (TS binding energy) after designing the binding pocket. The native matches (in the active scaffold in the native positions) are in black, the matches in alternate sites and/or scaffolds are in gray.

FIG. 7 shows superposition of native and predicted active sites for fuculose-1-phosphate aldolase (4fua) (7A) and DERA aldolase (1jcl) (7B). Orange, native TS model position and catalytic side chains; green, designated TS model position and catalytic side chains. The TS model is represented with thick sticks; the catalytic side chains, with thin sticks.

Figure 10:
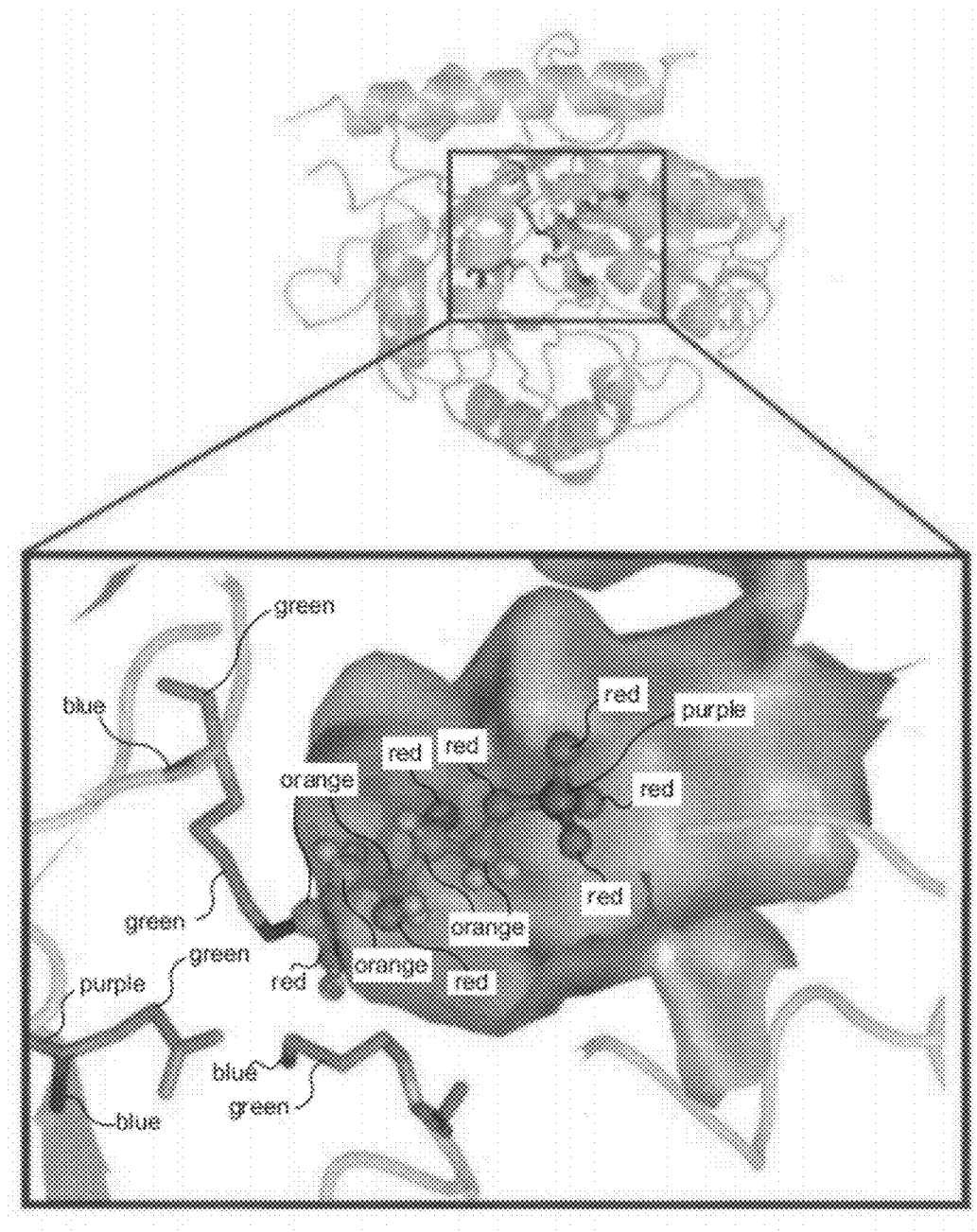

FIGS. 8 and 9 are tables of exemplary results of the second benchmark test used to evaluate one of the hashing methods (RosettaMatch);

FIG. 10 illustrates grafting an aldolase active site onto a decarboxylase scaffold. The top panel is an overall view of the designed protein; the bottom panel is a closer view of the active site. The protein backbone is shown in cartoon mode and colored according to its secondary structure. The TS model is shown in ball-and-stick mode, and the TS analog carbon atoms are colored in orange. The designed catalytic residues (Lys, Asp, Lys) are shown as sticks, and their carbon atoms are colored in green.

Figure 11:
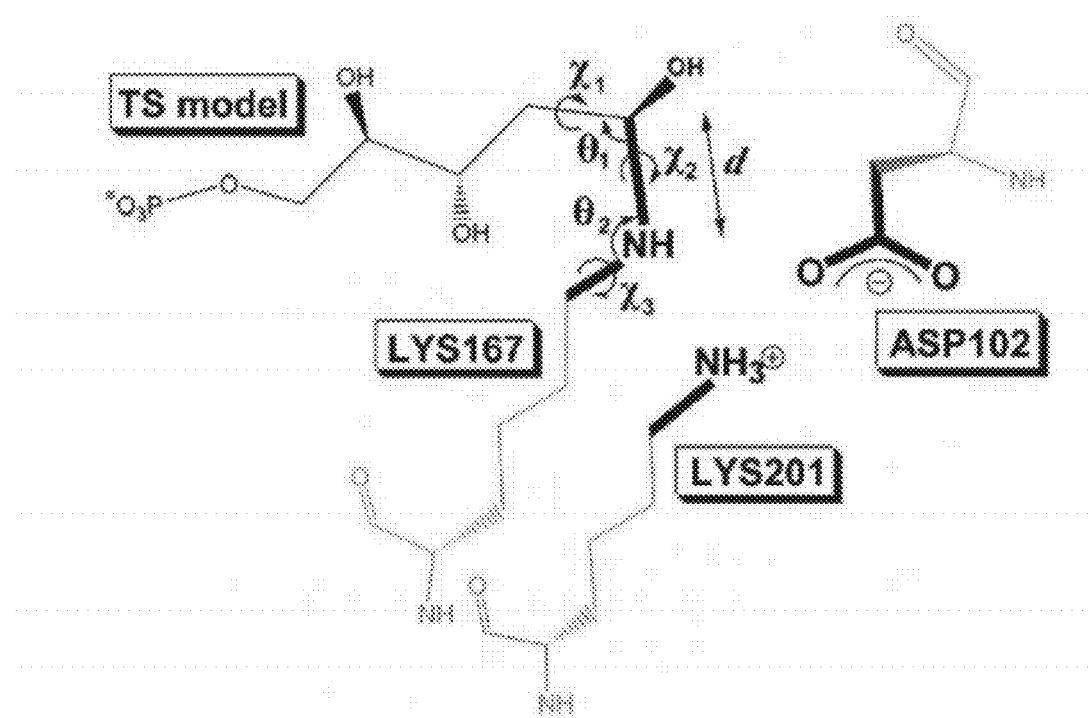

FIG. 11 illustrates geometric parameters used in active site description for deoxyribose-phosphate aldolase (DERA). Six geometrical parameters (d indicates distance; $\theta 1$ and $\theta 2$ indicate bond angles; $\chi 1$, $\chi 2$, and $\chi 3$ indicate torsional angles) are specified to describe spatial positions of the functional groups relative to the TS.

Figure 12:
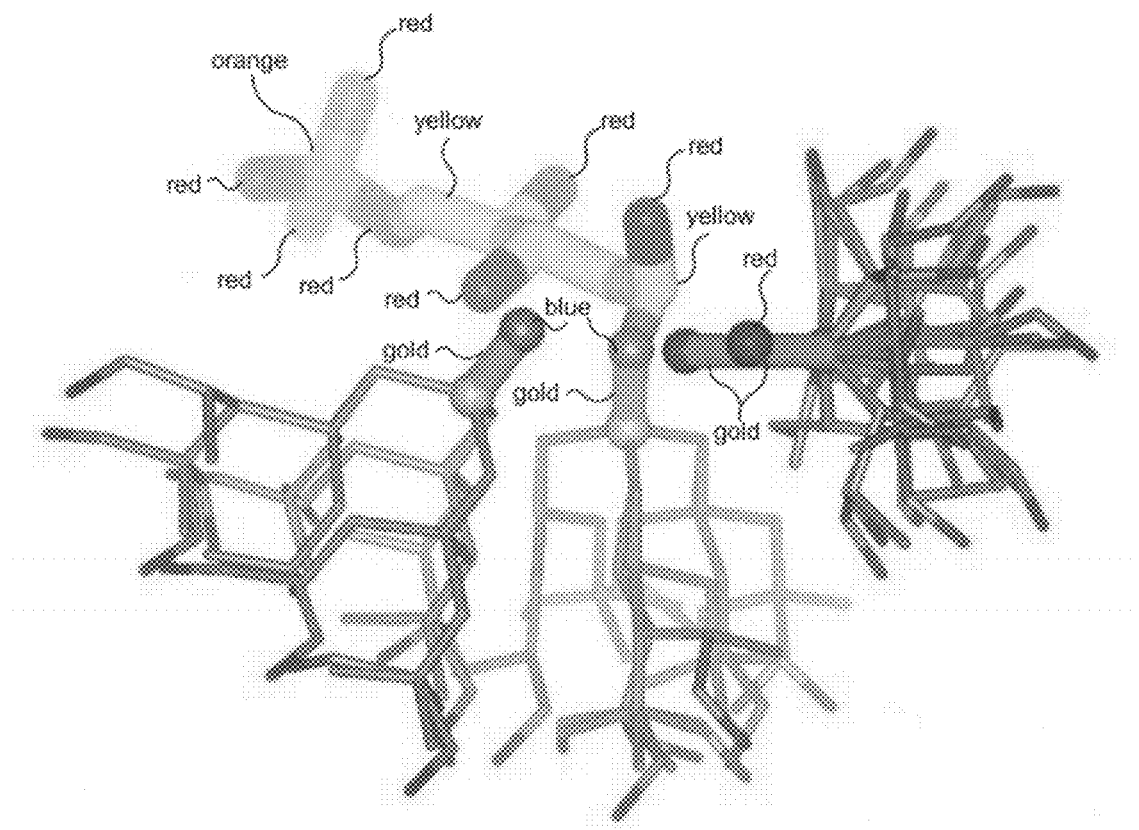

FIG. 12 shows an inverse rotamer tree for deoxyribose-phosphate aldolase (DERA) active site. The transition state is colored in yellow, and the key functional groups of the catalytic residues are in gold. The remainder of the side chains in the rotamer trees are shown using thinner lines in CPK coloring.

Figure 13C:
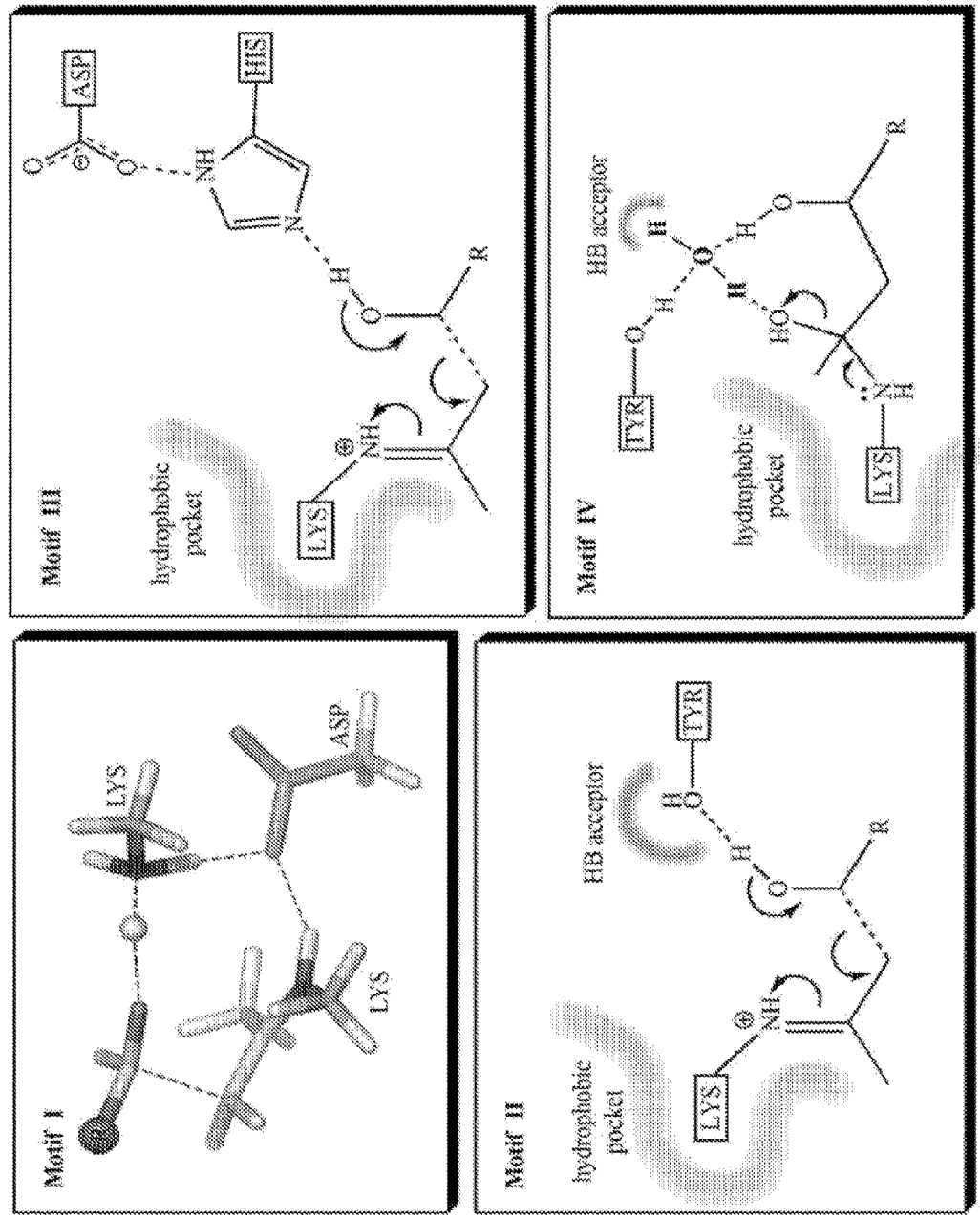
Figure 15A:
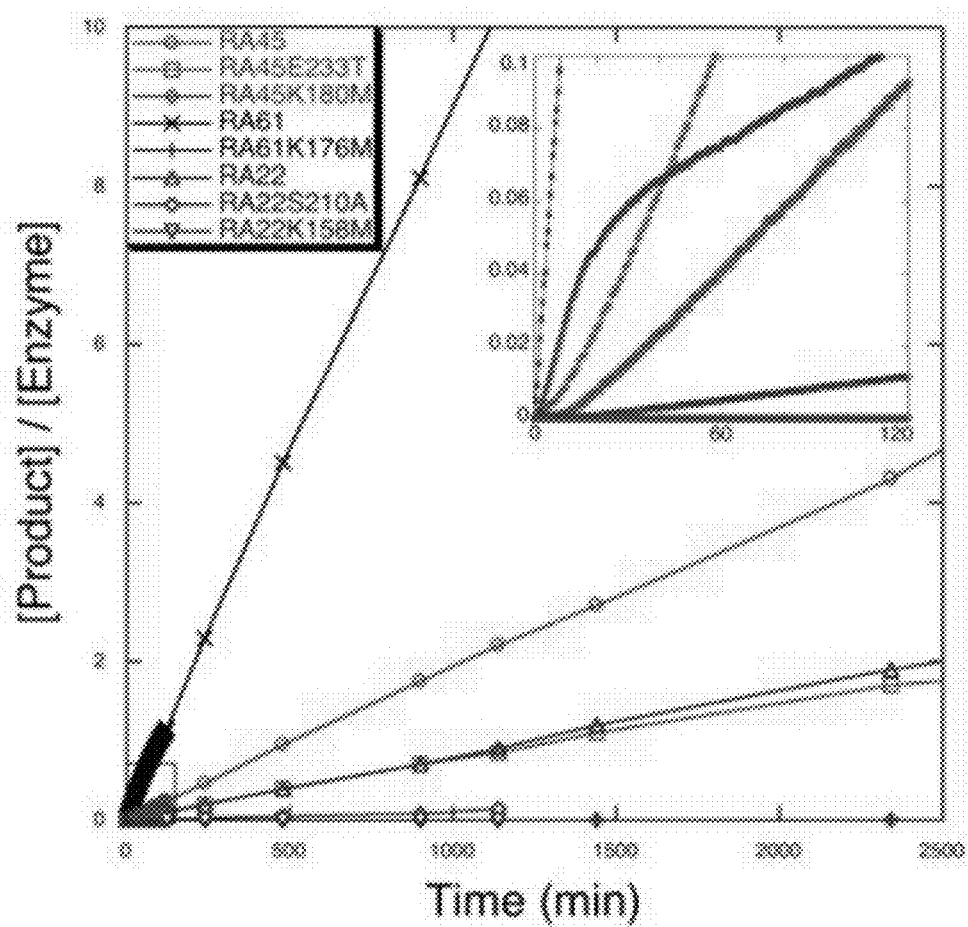
Figure 15B:
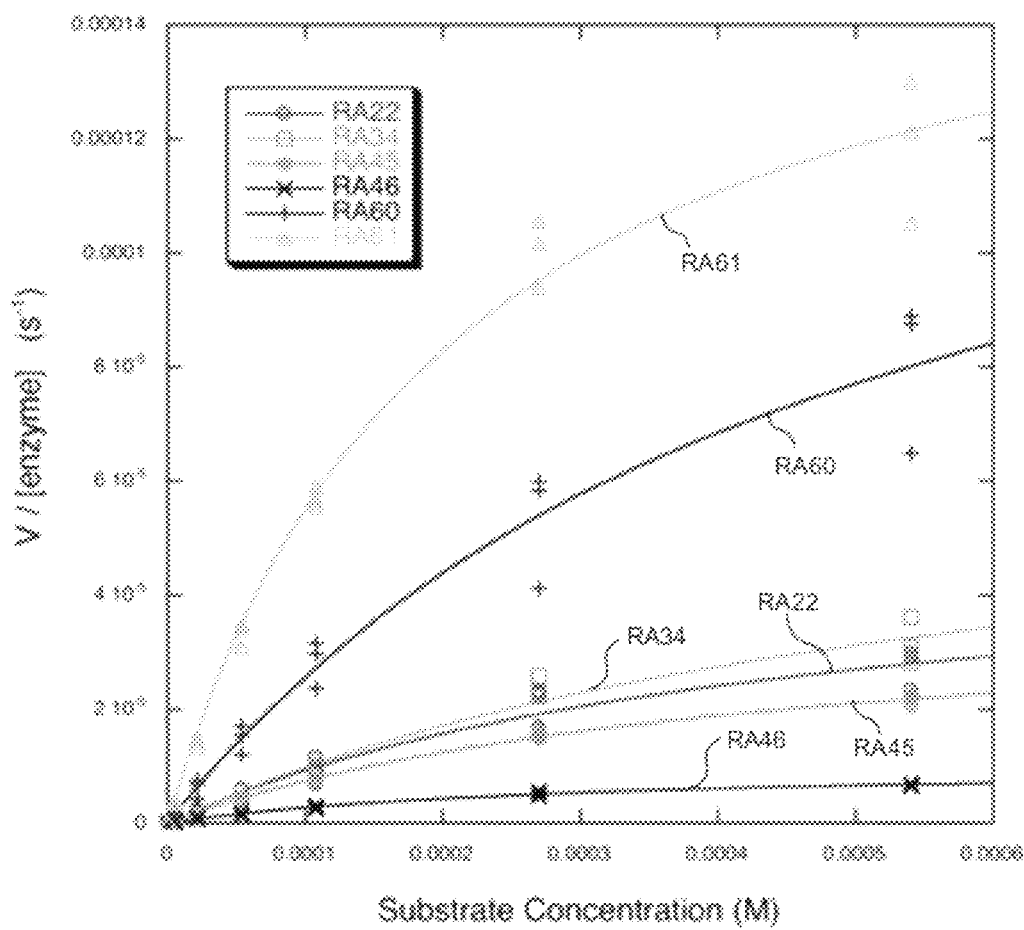
Figure 18A:
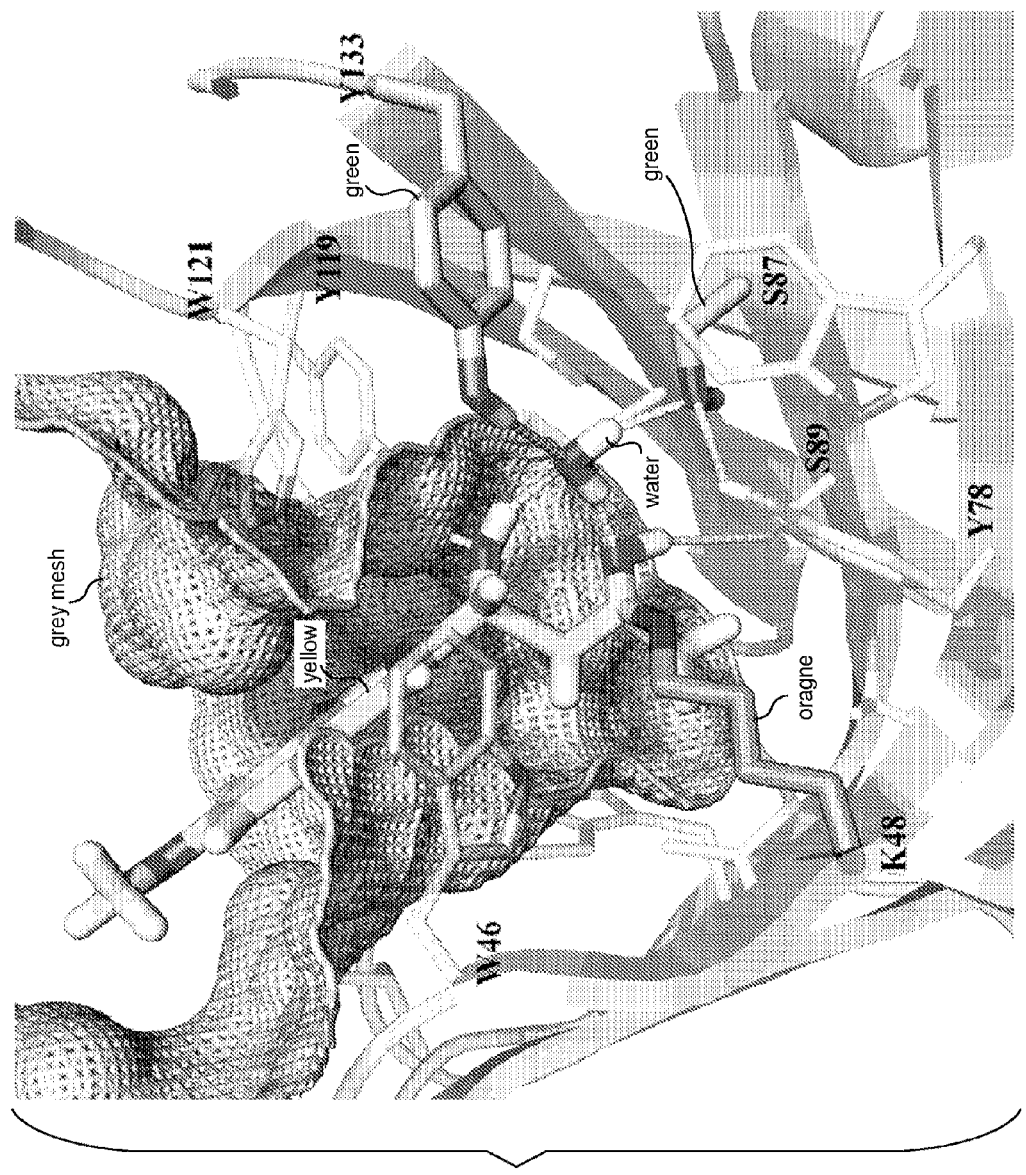
Figure 18B:
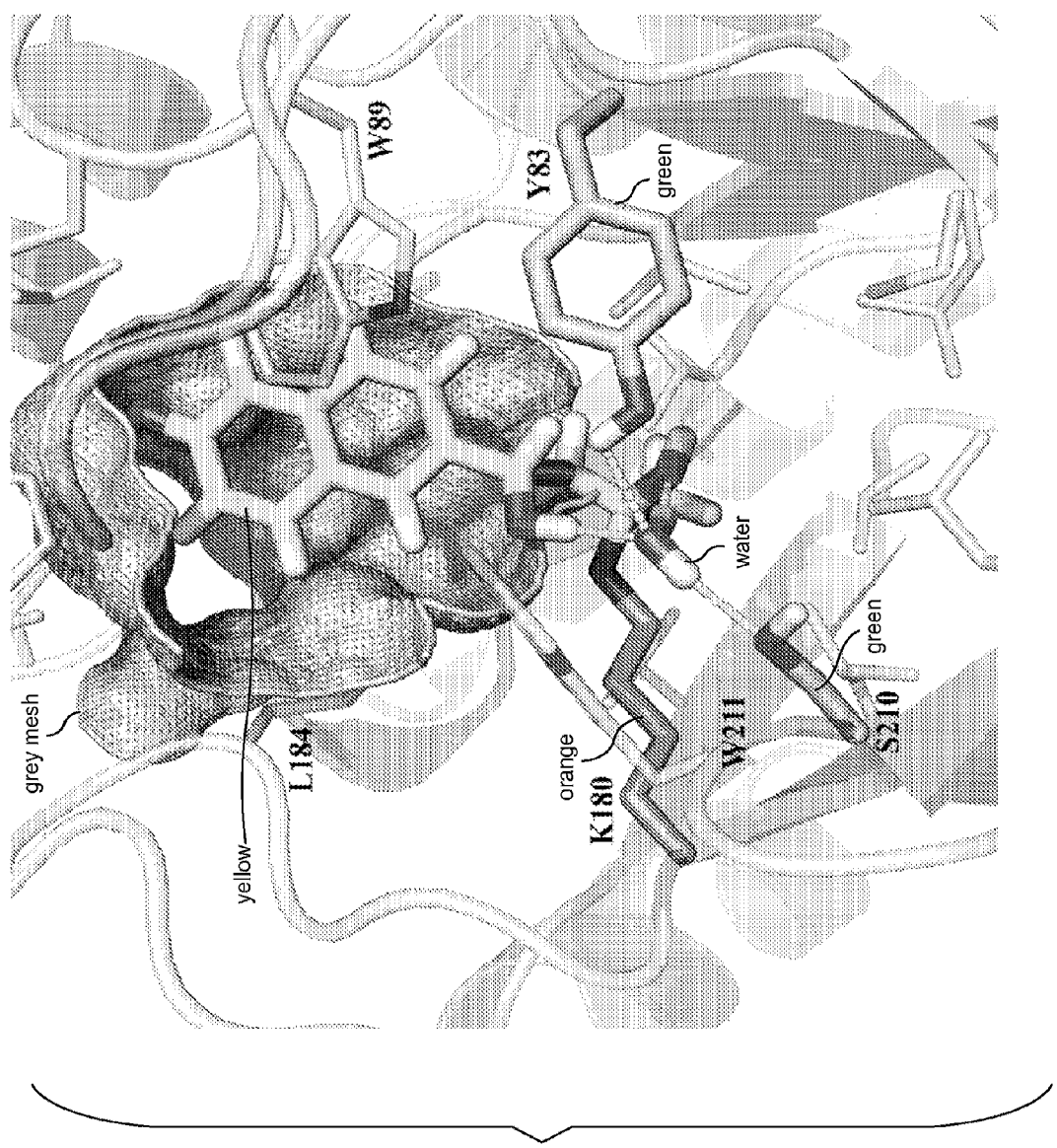
Figure 18C:
Figure 18D:
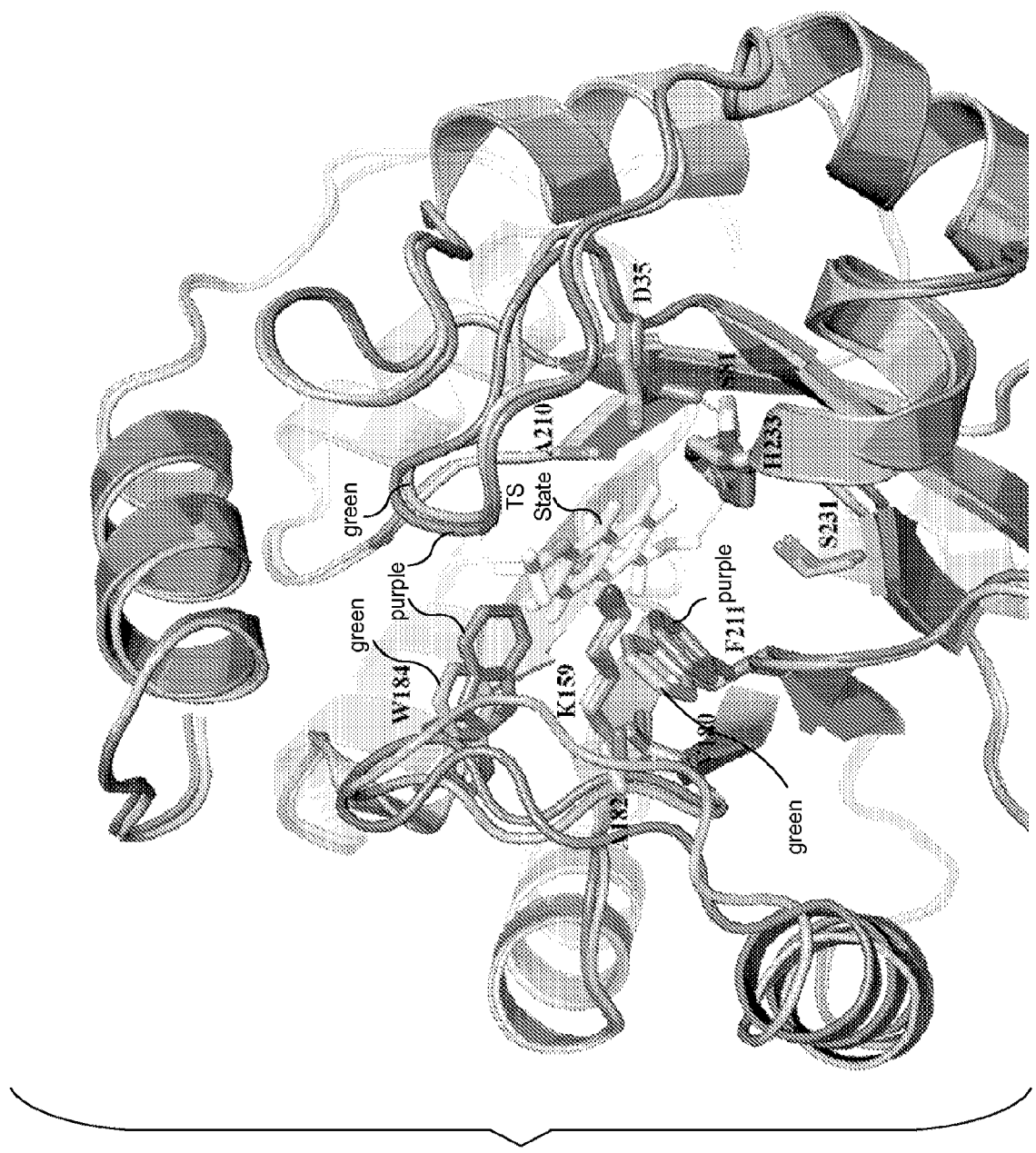
Figure 18E:
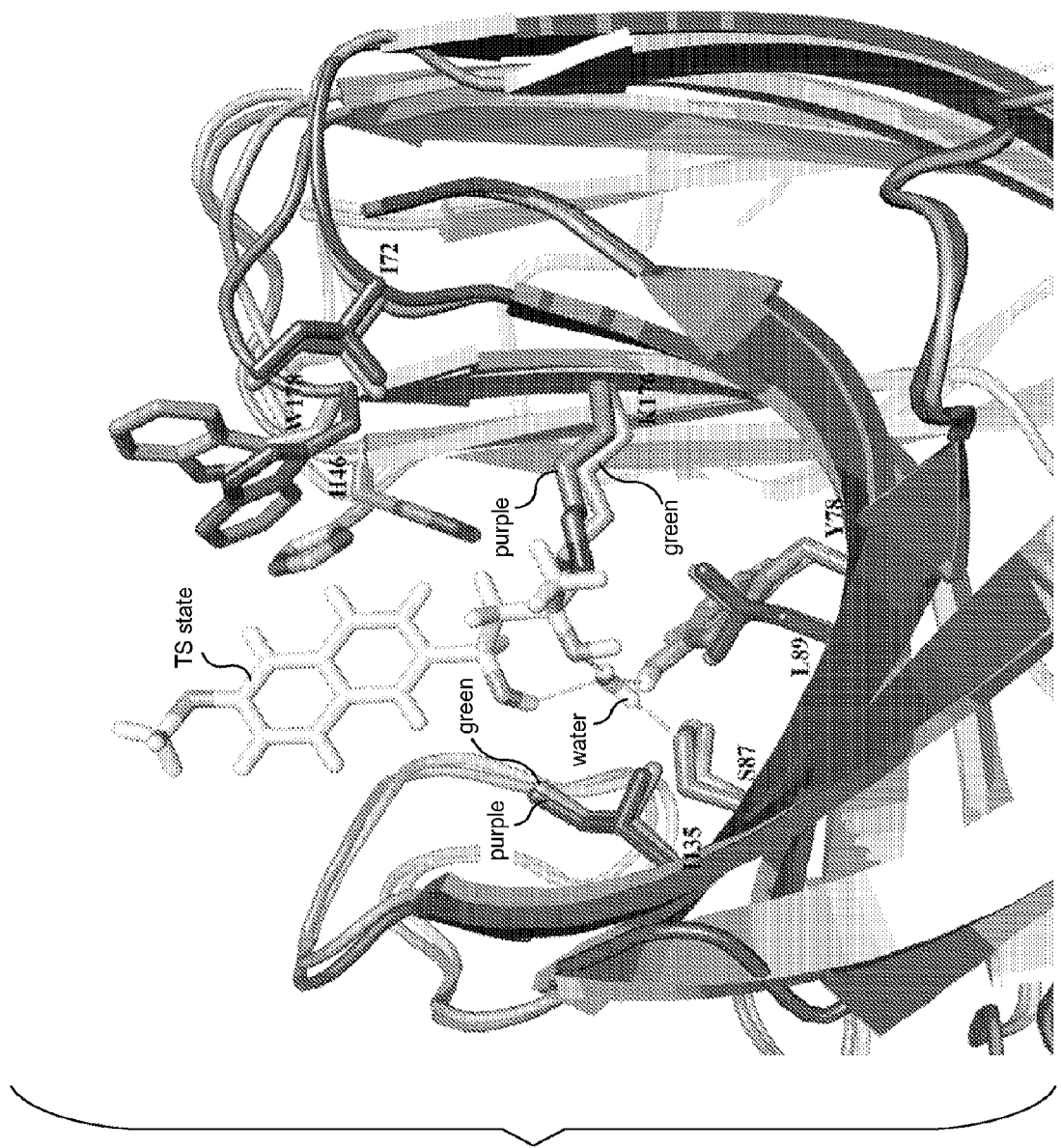
Figure 19:
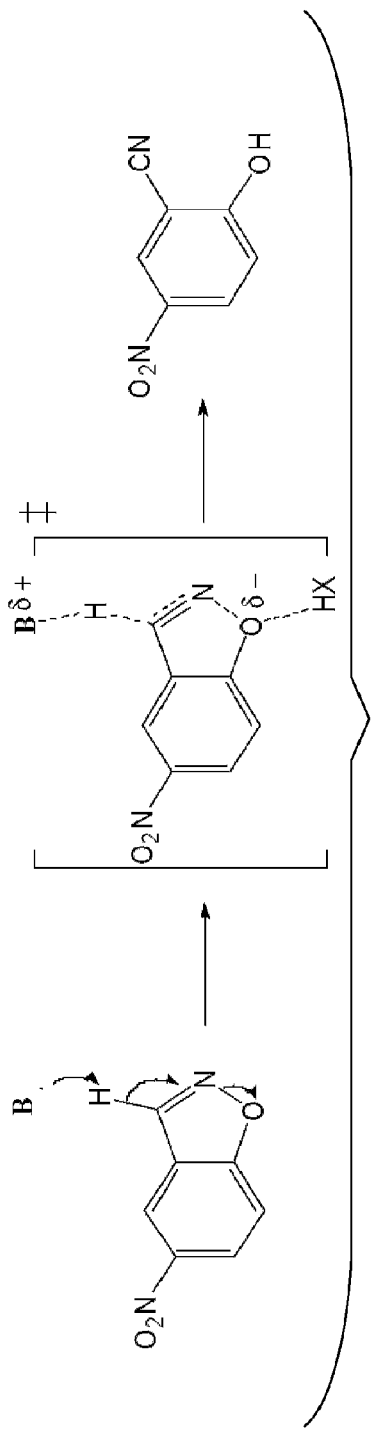
Figure 20:
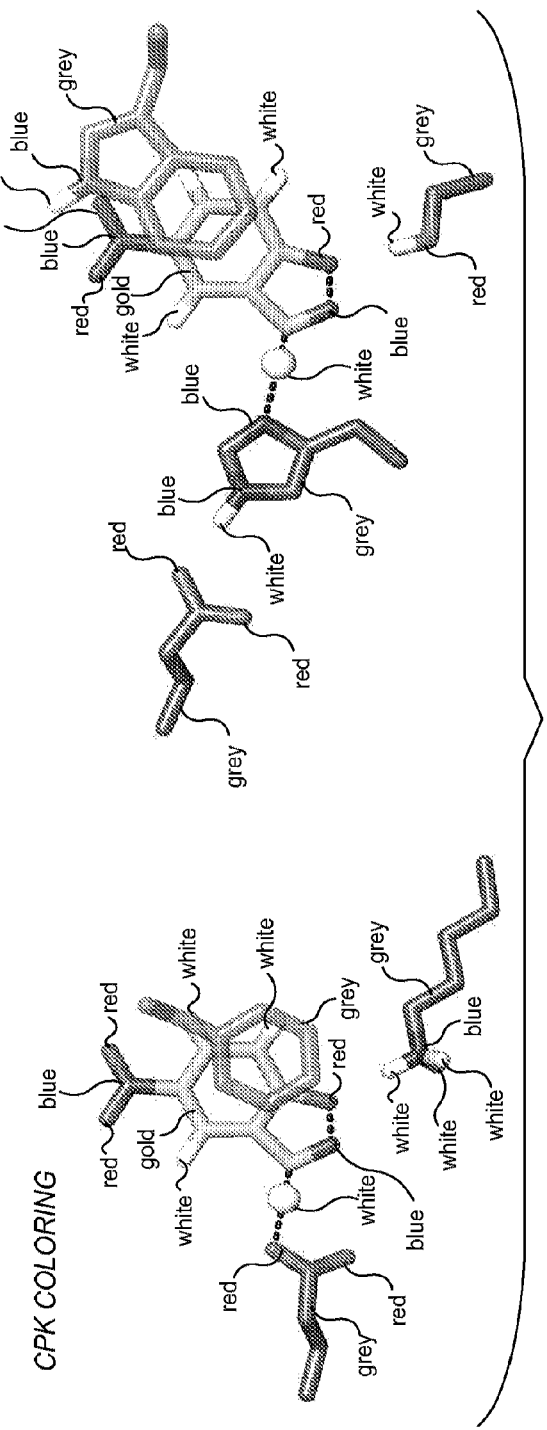
Figure 23A:
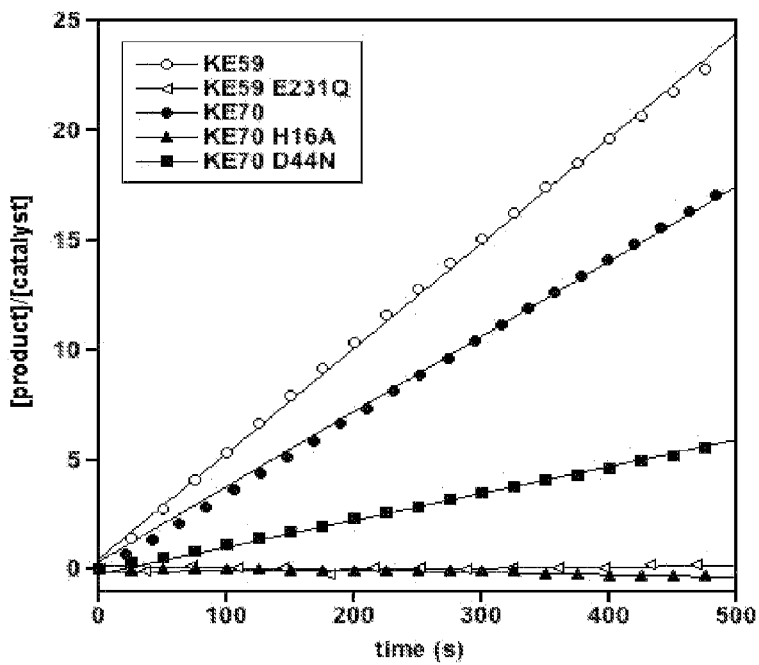
Figure 23B:
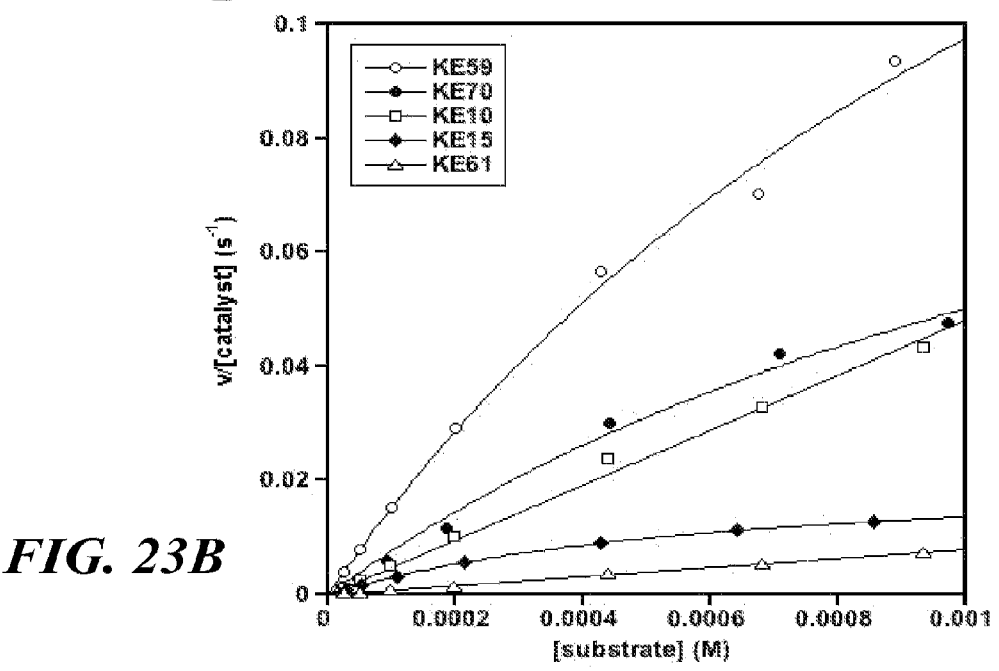
Figure 24A:
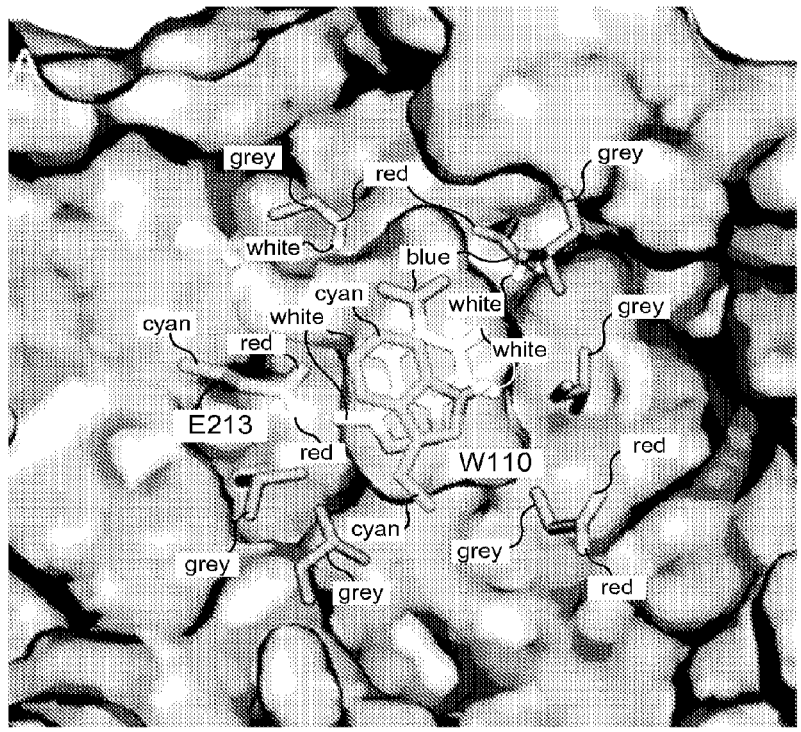
Figure 24B:
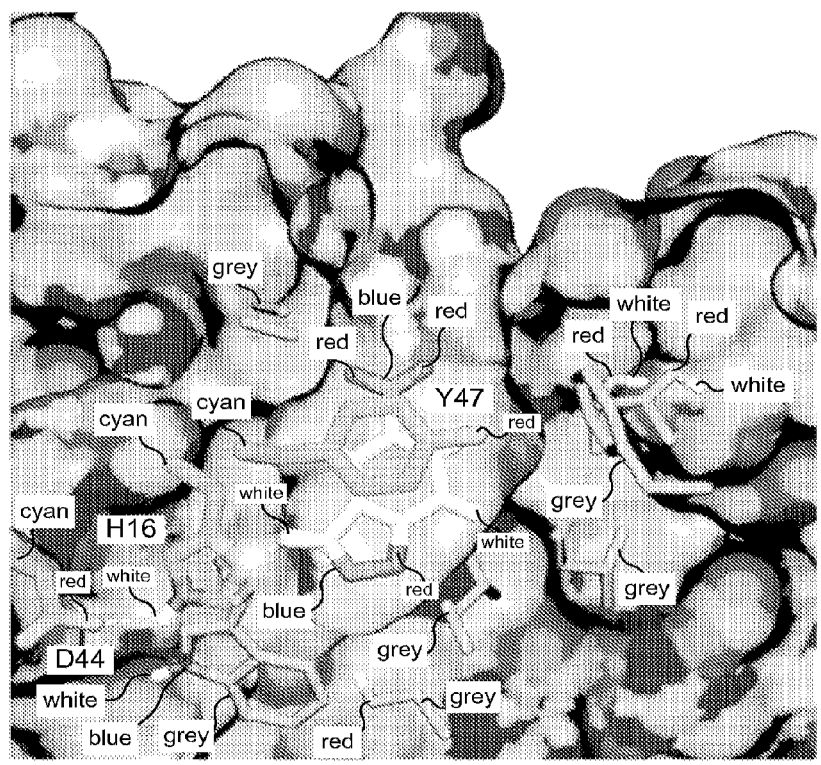
Figure 25:
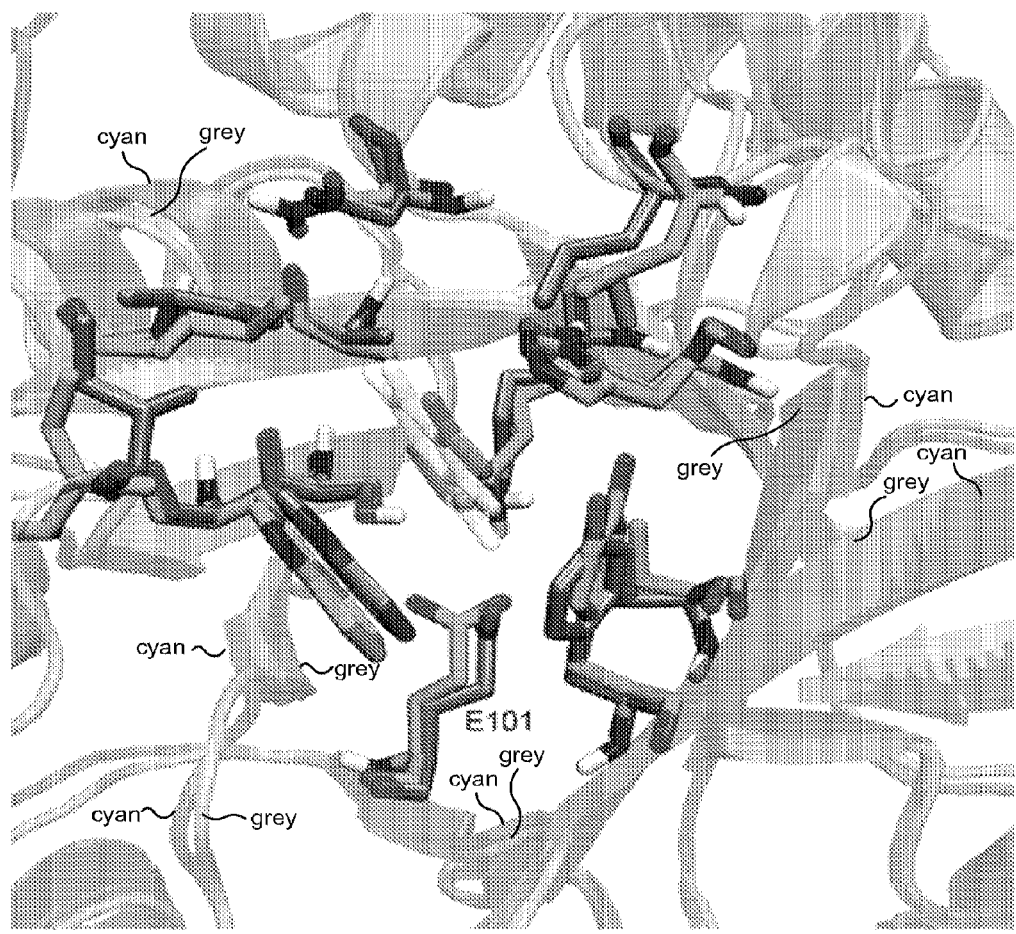
Figure 26:
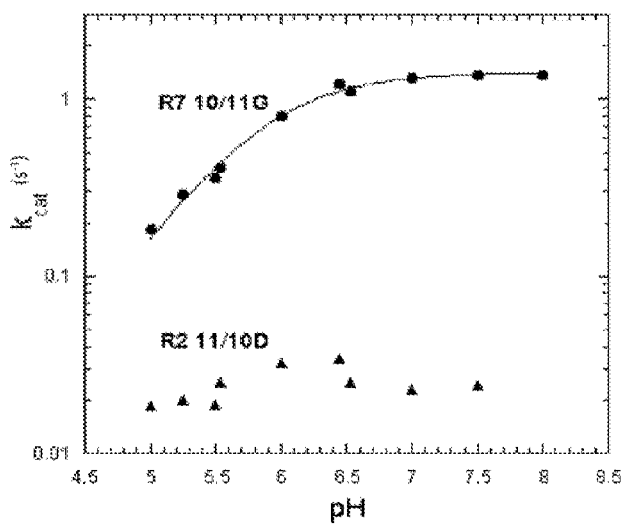
Figure 27A:
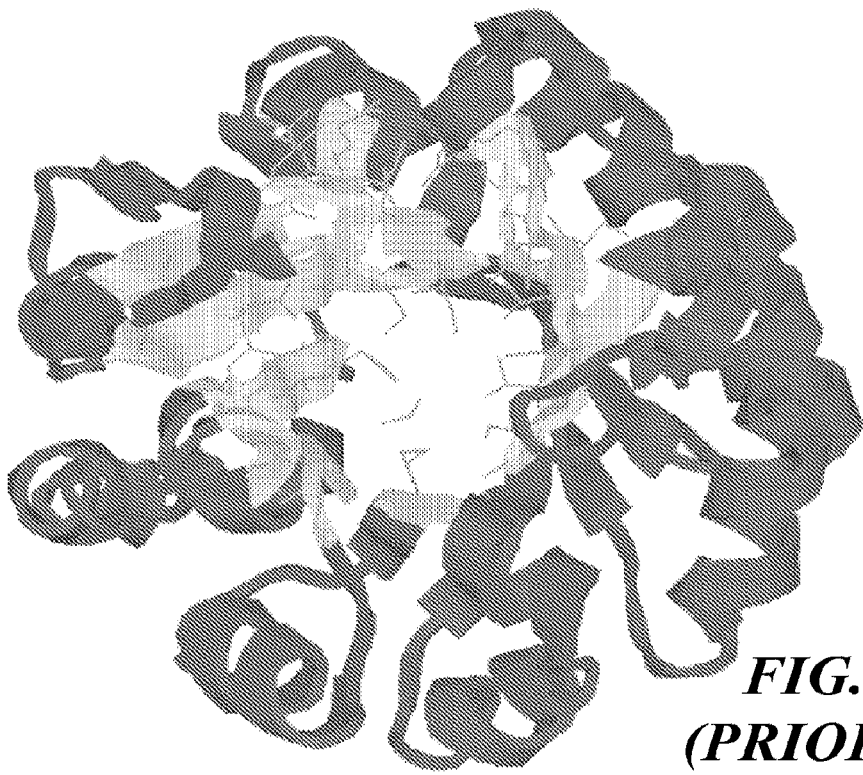
Figure 27D:
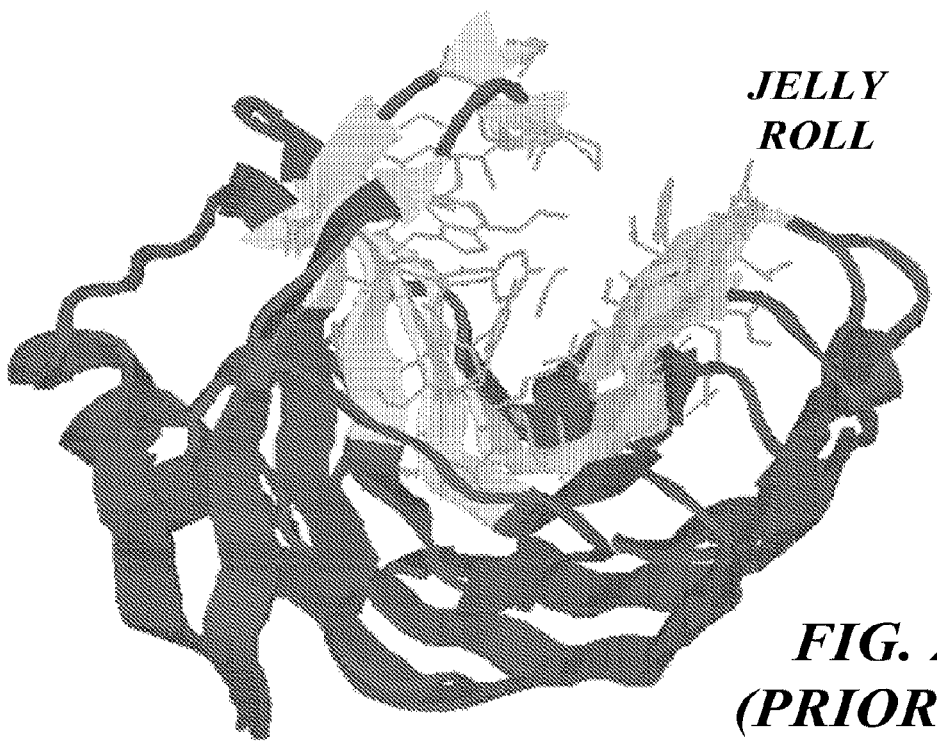
Figure 27B:
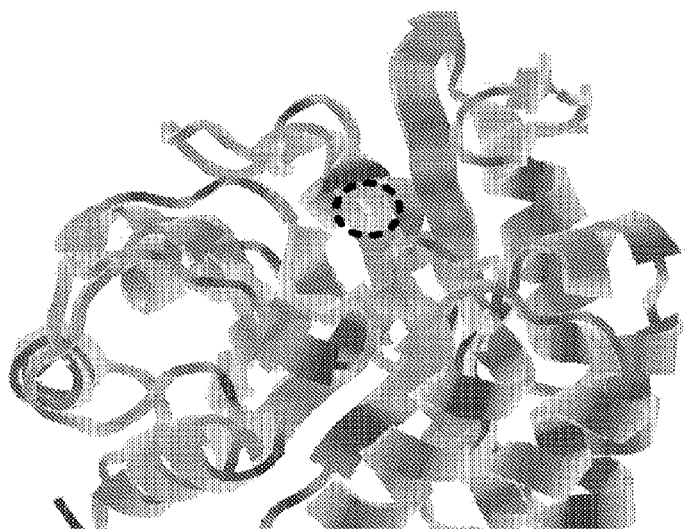
Figure 27C:
Figure 28:
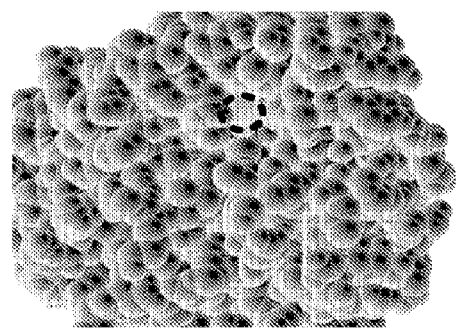
Figure 29A:
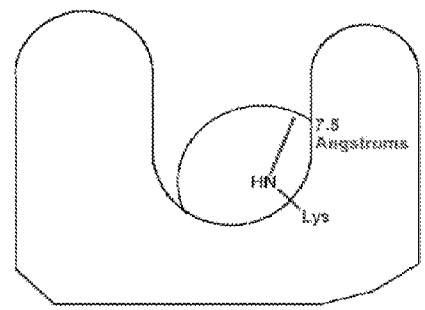
Figure 29B:
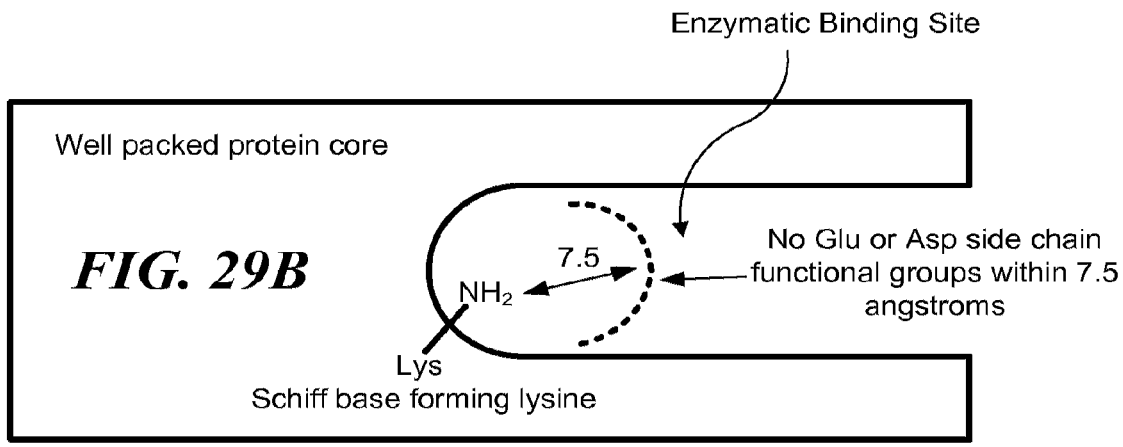
Figure 29E:
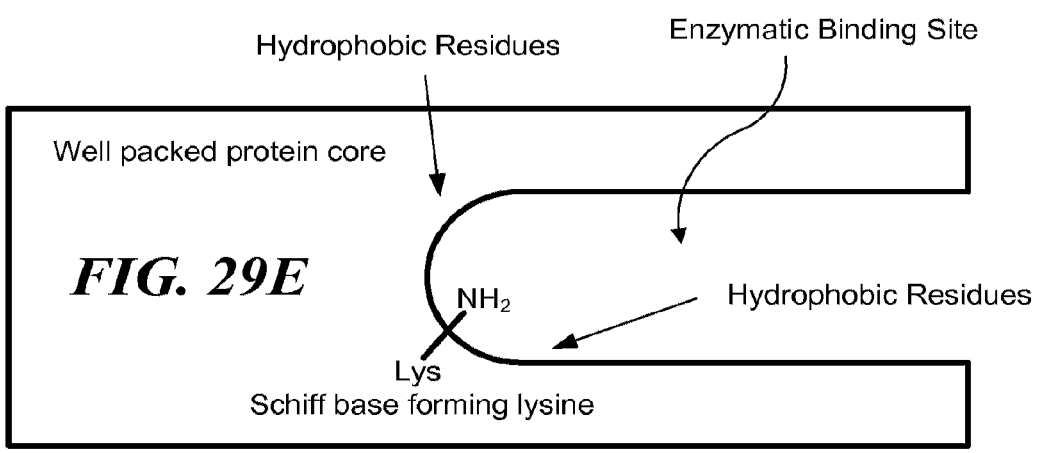
Figure 29F:
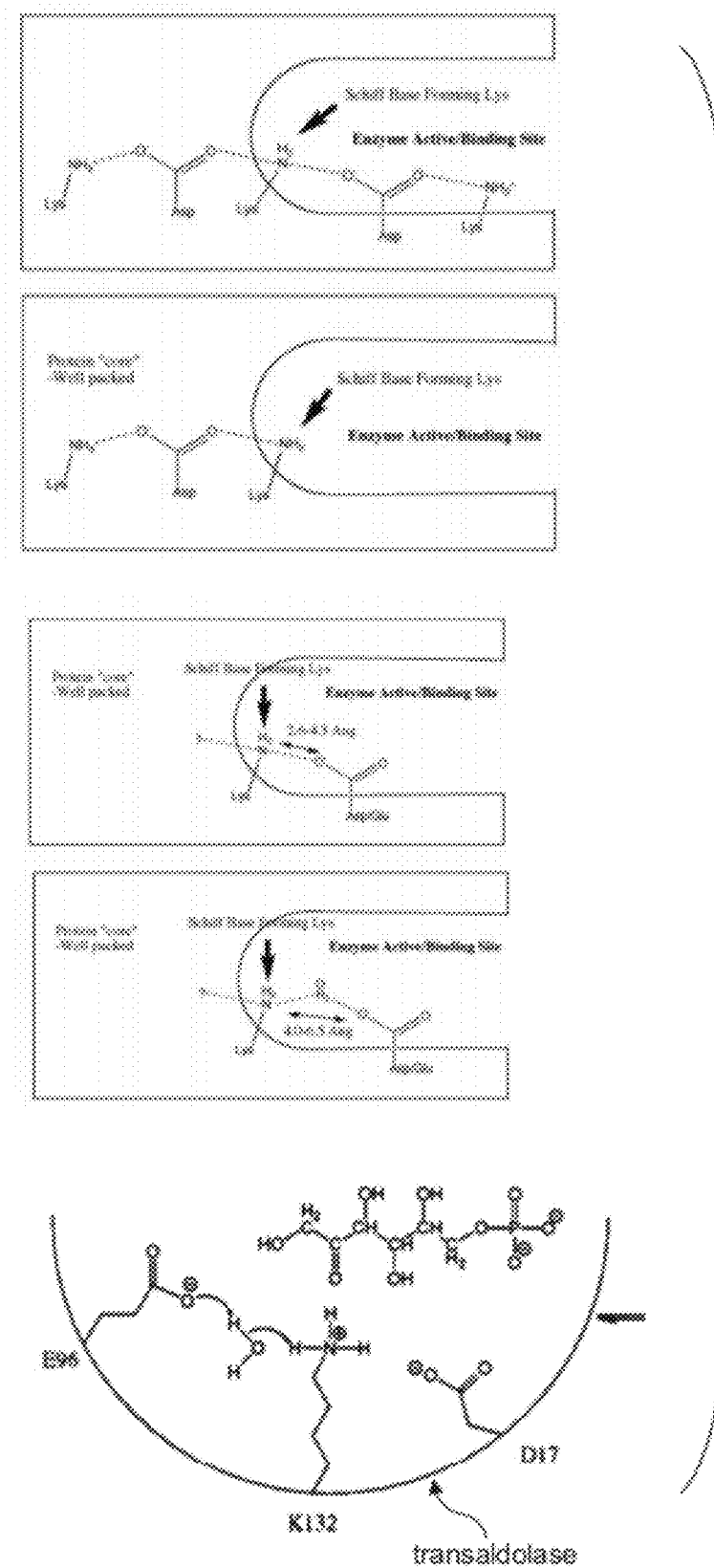

FIG. 13A schematically illustrates a retro-aldol reaction for which there is no naturally occurring aldolase;

FIG. 13B schematically illustrates a general description of the aldol reaction pathway for the retro-aldol reaction of FIG. 13A, using an active imine (Schiff-base) lysine and general acid/base chemistry;

FIG. 13C schematically illustrates active site motifs or the retro-aldol reaction of FIG. 13A, utilizing quantum mechanically optimized structures;

FIG. 14 is a table of retro-aldolase activity observed from 72 different protein sequences designed using the techniques disclosed here, 32 of which exhibited retro-aldolase activity;

FIG. 15A graphically illustrates progress curves of selected ones of the 32 synthetically designed protein sequences which exhibited retro-aldolase activity;

FIG. 15B graphically illustrates reaction velocities of selected ones of the 32 synthetically designed protein sequences, which exhibited retro-aldolase activity;

FIG. 16 is a table of rate of production formation for selected ones of the 32 synthetically designed protein sequences which exhibited retro-aldolase activity;

FIG. 17 is a table of rate enhancement information for each of the 32 synthetically designed protein sequences which exhibited retro-aldolase activity;

FIG. 18A schematically illustrates a synthetic aldolase referred to as RA60, which is based on the jelly roll scaffold and which exhibited relatively strong enzymatic activity;

FIG. 18B schematically illustrates a synthetic aldolase referred to as RA46, which is based on the TIM scaffold and which exhibited relatively strong enzymatic activity;

FIG. 18C schematically illustrates a synthetic aldolase referred to as RA45, which is based on the jelly roll scaffold and which exhibited relatively strong enzymatic activity;

FIG. 18D schematically illustrates how well the measured crystal of a synthetic aldolase referred to as RA22 matches its designed structure, RA22 being based on the TIM scaffold and exhibiting relatively strong enzymatic activity;

FIG. 18E schematically illustrates how well the measured crystal of a synthetic aldolase referred to as RA61 matches its designed structure, RA61 being based on the jelly roll scaffold and exhibiting relatively strong enzymatic activity;

FIG. 19 (Prior Art) graphically illustrates a reaction referred to as the Kemp elimination;

FIG. 20 schematically illustrates hypothetical active site motifs highlighting the two choices for the catalytic base required in the Kemp elimination—a carboxylate or a His-Asp dyad—employed for deprotonation, and a stacking aromatic residue for transition state stabilization;

FIG. 21 is a table of catalytic residues considered in the design of a synthetic Kemp elimination enzyme;

FIG. 22 is a table of catalytic residues involved in a specific computationally designed synthetic Kemp elimination enzyme and mutated variants;

FIG. 23A graphically illustrates progress curves of selected ones of the synthetically designed protein sequences, which exhibited Kemp elimination enzymatic activity;

FIG. 23B graphically illustrates reaction velocities of selected ones of the synthetically designed protein sequences, which exhibited Kemp elimination enzymatic activity;

FIG. 24A schematically illustrates a synthetic Kemp elimination enzyme referred to as KE59, which is based on the TIM scaffold and which exhibited relatively strong enzymatic activity;

FIG. 24B schematically illustrates a synthetic Kemp elimination enzyme referred to as KE70, which is based on the TIM scaffold and which exhibited relatively strong enzymatic activity;

FIG. 25 schematically illustrates how well the measured crystal of a synthetic Kemp elimination enzyme referred to as KE07 matches its designed structure, where portions of the Figure marked cyan (noting the original Figure was a full color Figure that has been converted to grayscale to accommodate patent filing requirements) correspond to the crystal structure, and portions of the Figure marked grey correspond to the designed structure;

FIG. 26 graphically illustrates the relationship between ph and catalytic rates for the synthetic Kemp elimination enzyme referred to as KE07 and mutated variants;

FIG. 27A (Prior Art) graphically illustrates the characteristic TIM folded shape exhibited by many protein sequences;

FIGS. 27B and 27C (Prior Art) graphically illustrate the characteristic location of the lysine active site for naturally occurring aldolases having the TIM folded shape, where the active lysine is disposed at the C-terminal end of the 6th beta strand (counting from the N-terminus, or first amino acid);

FIG. 27D (Prior Art) graphically illustrates the characteristic jelly roll folded shape exhibited by some protein sequences;

FIG. 28 (Prior Art) graphically illustrates the lysine active site for naturally occurring aldolases having the TIM folded shape, showing that the active lysine is disposed in a pocket surrounded by side chains of other amino acids;

FIGS. 29A-29D graphically illustrate the lysine active site for designed synthetic aldolases according to one aspect of the concepts disclosed herein, where the active lysine is disposed in a pocket, and in which care has been taken to reduce the side chains of other amino acids in close proximity of the active lysine;

FIG. 29E schematically illustrates an embodiment in which hydrophobic residues are incorporated into area proximate the active lysine, to ensure that the active lysine is in a nucleophilic state and ready to perform a catalytic function;

FIG. 29F schematically illustrates aspartic acid side chains disposed less than about 7.5 angstroms from the active lysine in naturally occurring aldolases;

Figures 30C, 30D, 30E:
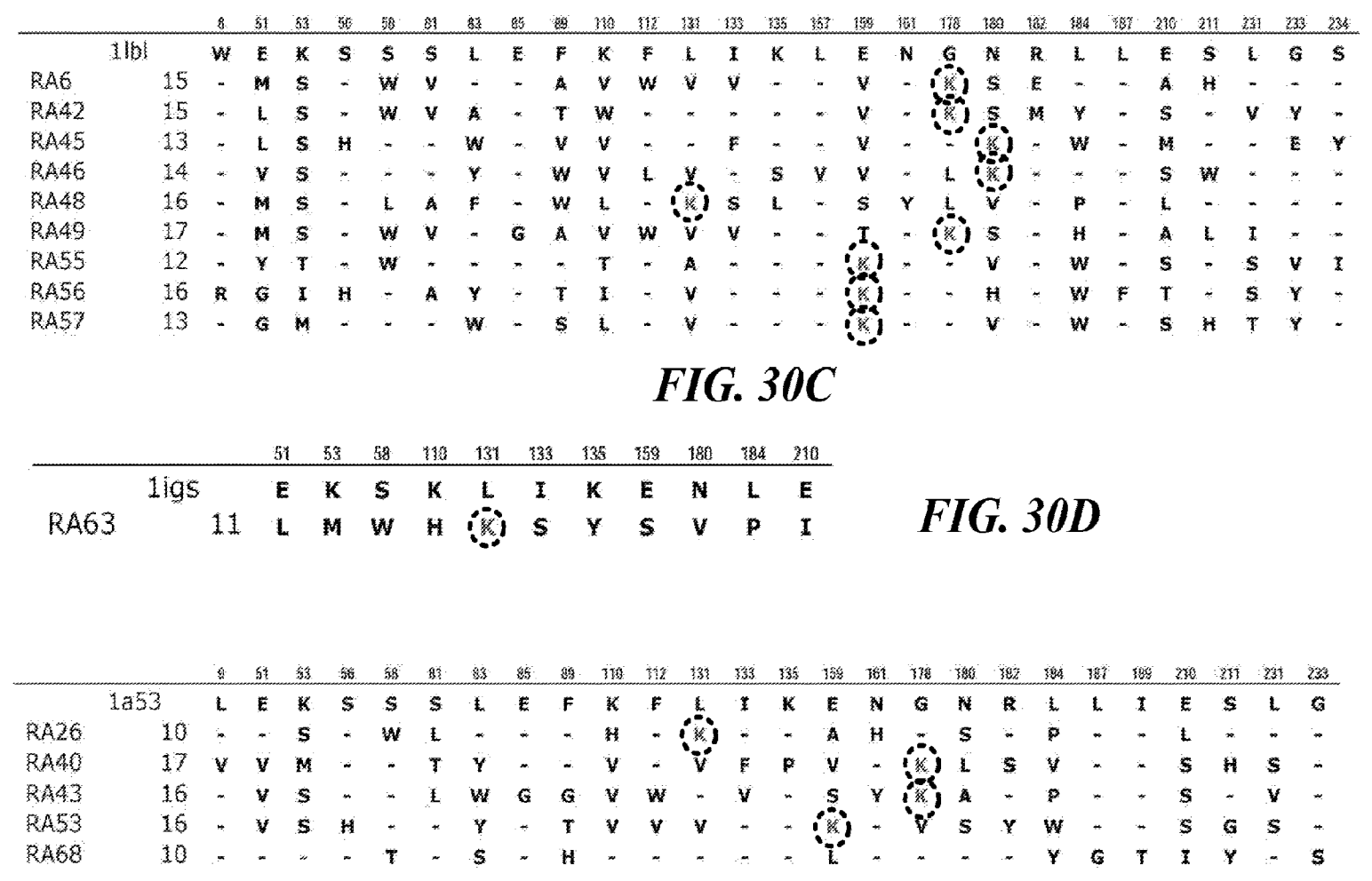

FIG. 30A graphically illustrates synthetic aldolases (SEQ ID NOs: 1-3) based on the 1i4n scaffold, indicating both the location of the active lysine and the amino acid changes to the 1i4n scaffold required to achieve the specific protein sequence representing the synthetic aldolase;

FIG. 30B graphically illustrates synthetic aldolases (SEQ ID NOs: 4-10) based on the 1ibf scaffold, indicating both the location of the active lysine and the amino acid changes to the 1lbf scaffold required to achieve the specific protein sequence representing the synthetic aldolase;

FIG. 30C graphically illustrates synthetic aldolases (SEQ ID NOs: 11-19) based on the 1lbl scaffold, indicating both the location of the active lysine and the amino acid changes to the 1lbl scaffold required to achieve the specific protein sequence representing the synthetic aldolase;

FIG. 30D graphically illustrates a synthetic aldolase (SEQ ID NO: 20) based on the 1 igs scaffold, indicating both the location of the active lysine and the amino acid changes to the 1 igs scaffold required to achieve the specific protein sequence representing the synthetic aldolase;

FIG. 30E graphically illustrates synthetic aldolases (SEQ ID NOs: 21-25) based on the 1a53 scaffold, indicating both the location of the active lysine and the amino acid changes to the 1a53 scaffold required to achieve the specific protein sequence representing the synthetic aldolase;

FIG. 30F graphically illustrates synthetic aldolases (SEQ ID NOs: 26 and 27) based on the 1thf scaffold, indicating both the location of the active lysine and the amino acid changes to the 1thf scaffold required to achieve the specific protein sequence representing the synthetic aldolase;

FIG. 30G graphically illustrates synthetic aldolases (SEQ ID NOs: 28-30) based on the 1m4w scaffold, indicating both the location of the active lysine and the amino acid changes to the 1m4w scaffold required to achieve the specific protein sequence representing the synthetic aldolase;

FIG. 30H graphically illustrates a synthetic aldolase (SEQ ID NO: 31) based on the 1f5j scaffold, indicating both the location of the active lysine and the amino acid changes to the 1f5j scaffold required to achieve the specific protein sequence representing the synthetic aldolase;

FIGS. 31A-31C graphically illustrate the synthetic aldolase corresponding to SEQ ID No. 4 (RA22), with the position of the active lysine being indicated by dashed lines;

FIG. 32 (Prior Art) schematically illustrates a Schiff-base at an active site, a common feature of the synthetic aldolases disclosed herein; and FIG. 33 schematically illustrates another design consideration involving a desired number of beta carbons that was employed in creating the synthetic aldolases disclosed herein.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

In the art of enzyme design, full color Figures are often employed to facilitate depiction of structural details. Some of the Figures contained herein were originally full color Figures which have been modified to comply with the modified grayscale requirement of patent Figures. Where the description refers to a particular part of a drawing by color, an appropriate text label has been added to the Figure.

With respect to the sequence listing provided herein in the Figures and as part of the actual Sequence Listing, as per convention in structural biology there is an assumed Methionine at position 1.

Disclosed herein are methods for computational enzyme design, as well as synthetic enzymes developed using the disclosed methods. In one embodiment, alternative configurations for naturally occurring enzymes are computationally designed. In another embodiment disclosed herein, novel retro-aldolases that catalyze the breaking of a carbon-carbon bond in a non-natural substrate are computationally designed. In still another embodiment, a synthetic Kemp elimination enzyme is computationally designed.

With respect to computationally designing alternative configurations for naturally occurring enzymes, the method is based on recapitulation of the locations and structures of native enzyme active sites in a set of naturally occurring enzymatic scaffolds. Given the backbone coordinates of 10 naturally occurring enzymes, and a list of the 10 reactions they catalyze, active sites are designed for each reaction in each scaffold. The designs for each reaction are collectively ranked based on their computed catalytic efficacy. To evaluate and guide the optimization of enzyme design methodology, it is assumed that the actual native enzyme is likely to be a better catalyst than any of the alternative designed enzymes. Based on this assumption, alternative designs can be evaluated based on the ranks of the actual native active site for each reaction among all the designs developed, and the associated computational cost required for the large number of calculations involved.

Overview of Synthetic Aldol Reaction Enzymes Disclosed Herein

One aspect of the concepts disclosed herein relates to synthetic enzymes for catalyzing aldol reactions (referred to herein, and in the claims that follow, as synthetic aldolases). Naturally occurring aldolases are well known, and include Aldolase A and Aldolase B, which are used by biological organisms to convert sugars to Dihydroxyacetone phosphate (DHAP). While aldol reactions are important metabolically, the utility of aldol reactions extends well beyond metabolism in biological organisms. Aldol reactions are a fundamental part of organic chemistry, and can be utilized in many different industrial processes.

Enzymes are generally chains of amino acids (i.e., proteins) and can range from about 62 amino acid residues to over 2,500 amino acid residues. In general, only a small portion of the enzyme (around 3-4 amino acids) is directly involved in catalysis. That portion, which binds the substrate, and carries out the reaction, is known as the active site.

While enzymes can be visualized as long, linear chains of amino acids, actually those chains fold to produce characteristic three-dimensional shapes. For a given protein sequence, the folded shape is not random, in that each identical protein sequence should achieve the same folded shape under the same conditions. When discussing the shape of protein folds, it is generally assumed that the ambient environment is similar to the environment in a biological cell. The folded state is referred to as the native state. Folding occurs as different amino acids in the chain (each of which has certain properties, such as hydrophobic, hydrophilic, electrically charged, etc.) interact with each other and their surroundings (i.e., solvents and/or salts or other molecules present in the ambient environment, and as a result of the ambient temperature and pressure) to produce a well-defined, three-dimensional shape. Shapes can be verified using analytical tools such as crystallography, or can be computationally predicted.

The resulting shape plays a large role in the activity of the enzyme. In the context of the concepts disclosed herein, the folded three-dimensional shape can be used to distinguish the synthetic aldolases from the naturally occurring aldolases, since the synthetic aldolases disclosed herein either exhibit significantly different folded shapes than do naturally occurring aldolases, or the active site of the synthetic aldolase is positioned differently than in naturally occurring aldolases.

Folded protein shapes often exhibit similarities that enable proteins and enzymes in their native or folded states to be classified based on their three-dimensional shape. Some common folds include the triose phosphate isomerase (TIM) barrel (or alpha-beta barrel), the Jelly Roll, the Rossmann fold, the Greek Key, and the Globin. The artisan of ordinary skill in the enzymatic art will readily recognize such terms.

A discussion of the computation design techniques is presented below, followed by a discussion of the synthetic enzymes developed using such techniques.

Overview of Computational Enzyme Design Techniques Disclosed Herein

As noted above, the techniques used to develop the synthetic enzymes disclosed herein are based on first identifying functional reactive sites required to promote the desired reaction. Next, hashing algorithms are used to identify potential protein backbone structures (i.e., scaffolds) capable of supporting the required functional sites. Another algorithm (RosettaDesign) is then employed to computationally develop a plurality of different protein sequences that accommodate the identified scaffolds. Computational ranking is performed to identify a relatively small number of potential enzyme designs, which can be empirically tested for the desired enzymatic efficiency. Potential candidates are then assayed experimentally. After experimental assay, interesting designs can be further improved using in vitro evolution to identify more efficient variants.

Thus, each of the computation enzyme design techniques disclosed herein employs unique hashing algorithms to enable active site searches in large numbers of scaffolds. Given a description of a catalytic site comprising a transition state structure surrounded by protein functional groups in geometrical positions optimal for catalysis and a set of protein scaffolds, these hashing methods search for sites in the scaffolds where the active site can be recapitulated.

In the first hashing method, an inverse rotamer tree approach is used with a modified version of a known geometric hashing algorithm (Bachar et al. 1993) to find positions in a set of scaffolds that can support the catalytic site. In the second hashing method, based on iterative side chain placement and hashing in six-dimensional space, candidate catalytic sites in scaffolds are detected in linear time. Both methods are followed by the design of the pocket using the standard Rosetta design methodology.

In the first hashing technique, (also referred to as the "inside-out" method), an inverse rotamer tree is built up from the active site description, and the backbone coordinates of all the rotamer combinations are compared to backbone coordinates of the set of scaffolds using a geometric-hashing based algorithm. In the second, "outside-in" hashing method, side chain rotamers and the transition state (TS) model are sequentially placed at all scaffold positions, and the position of the TS model is recorded in a hash table. The hash table is then scanned for TS positions that are found when placing each of the catalytic side chains independently. These positions represent sites in the scaffolds where the specified active site can be successfully constructed.

The two hashing methods have complementary strengths and weaknesses. The first method can search through large numbers of scaffolds, since the spatial relations between residues are all pre-computed, but it requires combinatorial enumeration of catalytic side chain rotamer positions. The second method is comparable in strength to searching through a set of scaffolds for a relatively simple site, but because the catalytic side chains are treated independently rather than combinatorially, it is the method of choice for searching complex active sites with finer side chain rotamer sampling. After putative active sites have been identified by one of these two methods, the remaining residues in the pocket around the docked TS model are redesigned to optimize transition state binding affinity. The resulting designs are ranked based on their catalytic efficacies as estimated based on the fit of the catalytic residues to the active site description and the computed TS binding energy.

Figure 1:
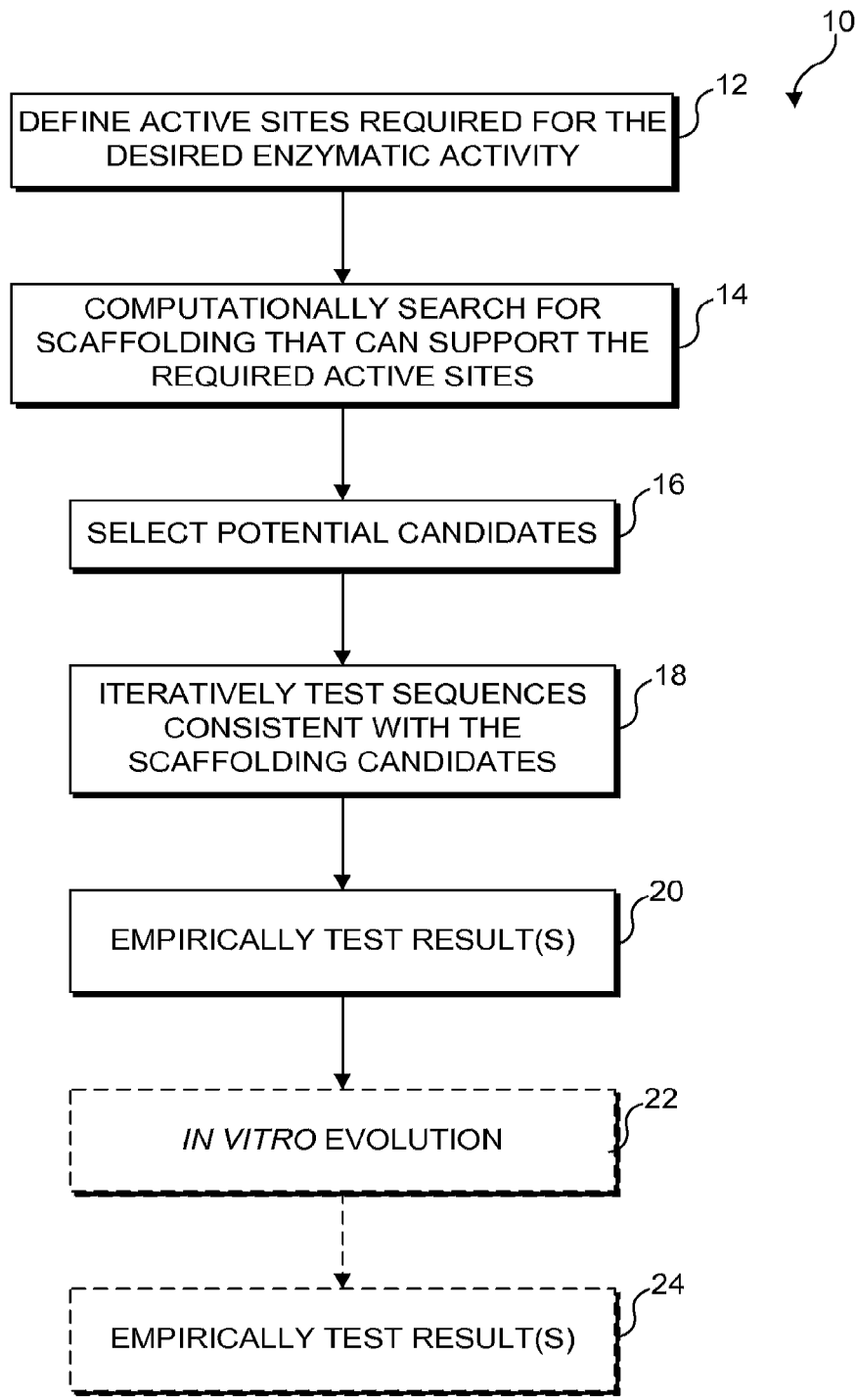
FIG. 1 is a block diagram showing exemplary steps for the computational design of synthetic enzymes.

FIG. 1 is a flowchart 10 of the overall method steps. In a block 12, the active sites required to achieve the desired enzymatic activity are defined. If the enzyme being designed is an alternative to a known naturally occurring enzyme, then the active sites in the naturally occurring (or native) enzyme can be selected. If an entirely new enzyme with no known naturally occurring counterpart is being designed, then knowledge of the chemical reaction to be enhanced with the enzyme is used to select appropriate functional groups for promoting that reaction. Such a process should be well within the skill of chemists familiar with chemical or biochemical reactions. This process is described in greater detail below, with respect to designing a synthetic Kemp elimination enzyme and novel retro-aldolases that catalyze the breaking of a carbon-carbon bond in a non-natural substrate.

In a block 14, a computational search is performed for scaffolding that can support the required active sites. The hashing methods discussed above can be used to perform such a search. In an exemplary, but not limiting implementation, on the order of 100,000 scaffolding configurations are initially identified. As discussed in greater detail below, a particularly effective software module has been developed to perform this task, the module being referred to as RosettaMatch.

In a block 16, potential candidates are selected based on the search performed in block 14. In an exemplary, but not limiting implementation, on the order of 20,000 scaffolding configurations are identified for further consideration.

In a block 18, various combinations of amino acids are computationally analyzed, to determine sequences that are consistent with the scaffolding configurations identified previously. In an exemplary, but not limiting implementation, on the order of 5,000 sequences are identified. If desired, additional analysis can be performed to further reduce the number of potential sequences, for example, to 150 or less. As discussed in greater detail below, a particularly effective software module has been developed to perform this task, the module being referred to as "RosettaDesign."

In a block 20, empirical testing is performed to build and test the actual enzymatic activity of selected sequences. If desired, those sequences showing promise are further manipulated using the technique of in vitro evolution (as indicated in an optional block 22), and the results are then empirically tested (as indicated in an optional block 24).

Recapitulation of Native Enzymatic Sites

In an empirical study, two native active site recapitulation tests were used to benchmark the two new hashing methods (the techniques involved in block 14 of FIG. 1). Ten crystal structures of enzyme-transition state analog complexes or enzyme-inhibitor complexes with a resolution of 2.5 A or better were taken from the Protein Data Bank (PDB). The resulting benchmark set includes members of the hydrolase, lyase, isomerase, and transferase enzyme families (Table 1/FIG. 3); the only major family missing from the benchmark set is the oxidoreductase family, which typically employs non-protein cofactors. The number of catalytic residues at the active sites varies from two to four, and the catalytic amino acids include Asp, Glu, Asn, His, Cys, Ser, Tyr, and Lys (also as shown in Table 1/FIG. 3).

Figure 2:
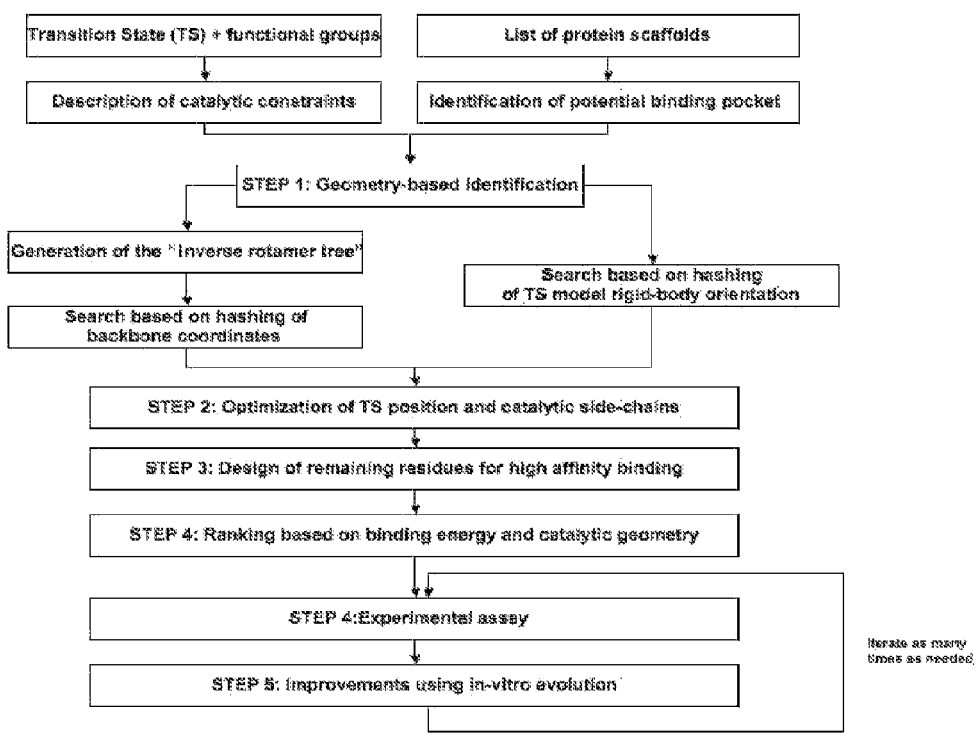
FIG. 2 is another block diagram illustrating exemplary steps for the computational design of synthetic enzymes.
Figure 4:
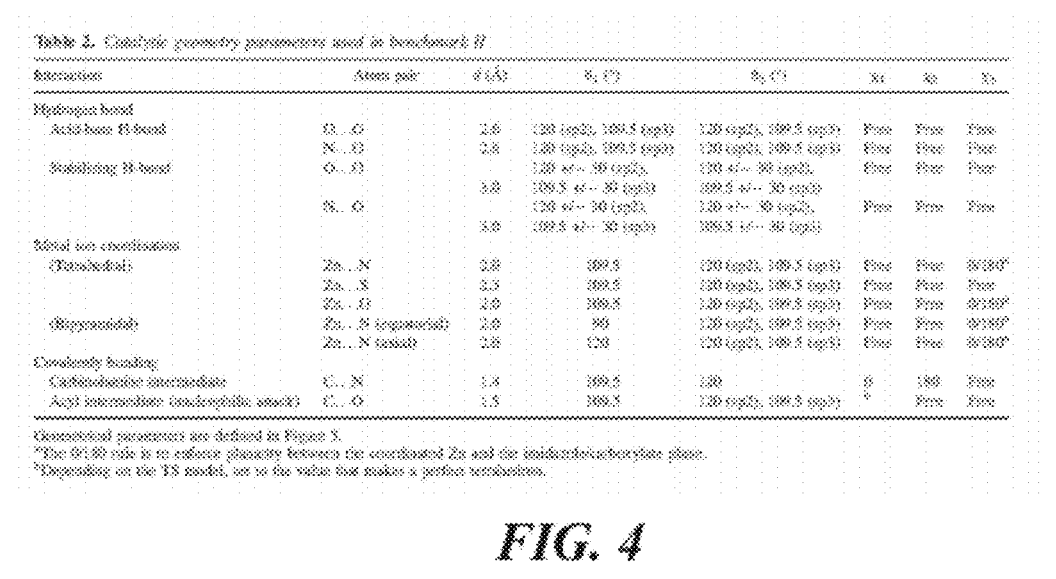

The catalytic residues documented as being involved in the catalytic mechanism for each enzyme of the benchmark were used to build the catalytic site descriptions for the corresponding reaction. For each chemical reaction, two benchmark tests were carried out using the complete protocol described in FIG. 2, first using the inverse rotamer tree method (the first hashing method) and then using RosettaMatch (the second hashing method). In the first benchmark test, the geometrical parameters relating the TS analog and the functional atoms are taken directly from the crystal structure of the complex. In the second benchmark test, the geometrical parameters are set to optimal values based on the simple rules described in Table 2 (FIG. 4). The challenge is to recapitulate the native active site by correctly identifying among all designs in all scaffolds, the native site in the native scaffold based on the predicted catalytic efficacy. In practice, the first benchmark case was implemented using both hashing methods, whereas the second benchmark was implemented only with RosettaMatch, because it was determined that the first hashing method was too computationally intensive.

Benchmark Results Starting from Native Catalytic Geometries

For the first test, the TS model and the functional group geometry, but not the conformations of the catalytic side chains, are taken directly from the crystal structure. The results using both match methods are reported at each stage in the design process in Table 3 (FIG. 5). It is expected that a good enzyme design method should identify the naturally occurring site in the correct scaffold and rank it relatively high compared to non-native sites. For all 10 native active sites, both native matches (native catalytic residues at native sequence positions) as well as cross matches (different positions in the native scaffold or a non-native scaffold) are found. Encouragingly, the rank of matches in the native scaffold in the native positions improves throughout the design process: after minimization (described below) and design, both hashing methods lead to a remarkably good native site recapitulation (FIG. 6A corresponding to results after minimization, and FIG. 6B corresponding to results after design).

In six out of the 10 benchmark sets, the design predicted to bind the TS model the tightest is in the native scaffold in the native positions. For the remaining benchmark cases, the rank is usually within the first percentile, except for the deoxyribosephosphate aldolase (DERA) and aspartic proteinase cases with the RosettaMatch method. Both hashing methods not only recapture the native enzymatic site in most cases, but also accurately reproduce the TS model position and active site side chain conformations.

Figure 7A:
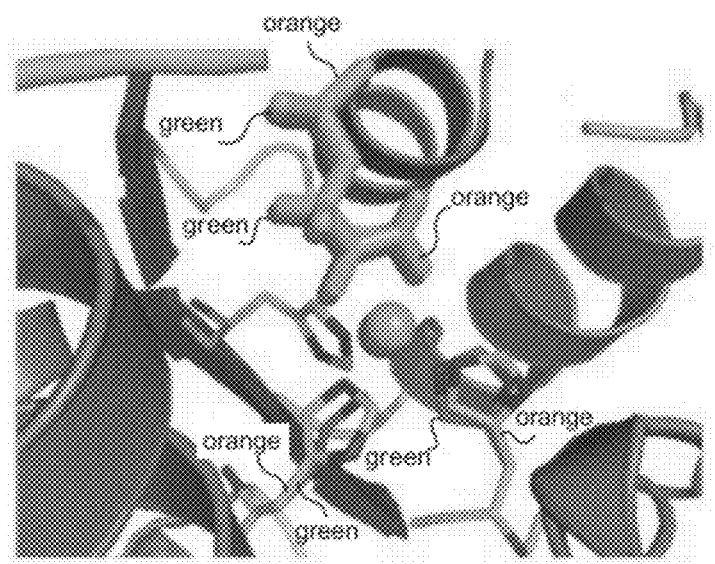
Figure 7B:
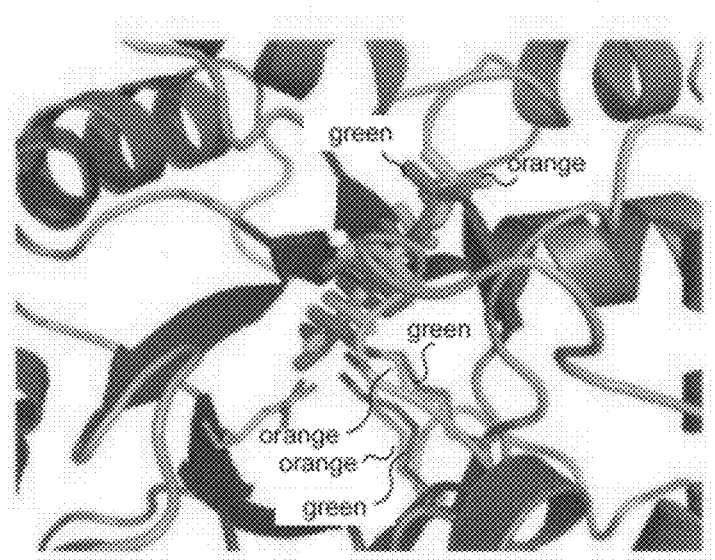

Two examples of active site recapitulation are shown in FIGS. 7A and 7B (i.e., results from RosettaMatch for two different reactions; the most visual example of the inverse roomer tree is FIG. 12). Orange portions of each Figure represent actual amino acid locations, while green portions represent predicted locations obtained using the hashing techniques. Note the close overlap between the orange and green portions indicate the effectiveness of the hashing methods. The results for the benchmark show that the inverse rotamer tree (first hashing method) and RosettaMatch (second hashing method) perform equally well on average for the test cases, leading to good discrimination by score between native and non-native matches after minimization and design as seen in FIGS. 5, 6, and 8. The non-identical ranking of the native matches found using the two methods is due in part to the use of different rotamer libraries (RosettaMatch uses the Dunbrack backbone-dependent rotamer library, while the inverse rotamer tree method uses the backbone-independent rotamer library), and hence, the reconstructed sites are not identical.

Benchmark Results Starting from Idealized Catalytic Geometries

In the second benchmark test, the geometrical parameters defining the functional group from the catalytic residues are chosen using the geometrical rules listed in Table 2 (FIG. 4). Since some of the degrees of freedom are free to adopt a range of discrete values, the number of possible matches is much larger than in the previous test. Because of the combinatorial increase of the number of possible active sites, the inverse rotamer tree cannot easily handle such a problem, since all combinations must be enumerated prior to searching. The RosettaMatch method avoids the combinatorial explosion by treating each catalytic side chain independently; the results of this benchmark test for this method are summarized in Table 4 (FIG. 8). Because the active site descriptions are considerably more general than in the first benchmark, the rank of the native active site is not always high, but in four of the nine test cases reported, the native active site has the highest rank after minimization and design. The complete design process requires one or two CPU days per scaffold on a computer using an Intel Corporation Xeon™ processor at 2.8 GHz with 2 GB of random access memory (RAM), with full diversification of the free degrees of freedom for a three-residue active site (type II aldolase). Algorithm improvements have since resulted in faster processing times.

Thus, the computational design strategy allows for rapid identification and evaluation of designed sites on many scaffolds that can be tested experimentally.

Sensitivity to Backbone Variation

To quantitatively determine the sensitivity of the RosettaMatch algorithm to the precise positions of the backbone atoms, the performance of the method in recognizing native matches in homologous scaffolds was investigated using PSI-BLAST (Altschul et al. 1997) to identify sequence homologs with known structures for four of the enzymes in the benchmark set, including: aspartic proteinase, g-chymotrypsin, cytosine deaminase, and bovine carboxypeptidase A, which respectively contain two, three, four, and four catalytic residues. The number of homolog structures and their backbone root mean square deviation (RMSD) to the query structure for each enzyme are summarized in Table 5 (FIG. 9). As indicated in Table 2 (FIG. 4), the techniques disclosed herein are capable of finding the active site for homolog structures of up to 4.0 A backbone RMSD, showing that the techniques are tolerant of variation in backbone coordinates up to this level (the native site can be found multiple times because of the fineness of the rotamer sampling).

Previously Employed Algorithms

The enzyme active site recapitulation test presented above provides a rapid and comprehensive benchmark to evaluate and guide the improvement of enzyme design methods. It should be noted that other attempts have been made to provide an algorithm for starting with a geometric description of an active site, searching through a protein scaffold for positions where it can be placed, and designing the surrounding residues, as reported in previous studies. Significantly, the two hashing algorithms described herein have several advantages over previously described methods.

The inverse rotamer tree-based search complexity does not depend on the number of scaffolds searched, whereas previous methods scale at least linearly with the number of positions (and, consequently, scaffolds searched). For example, at least one previous algorithm ("Dezymer;" developed by Hellinga a and Richards 1991) places all rotamers for the anchor residue at each position, thereby scaling at least proportionally with the number of positions considered. The approach taken by Bolon and Mayo (2001) also places an extended rotamer (which includes the TS model) on each search position, leading to the same dependence. The computational efficiency of the inverse rotamer tree-based algorithm can be a substantial advantage, particularly if large-scale enzyme site searches are required. The inverse rotamer tree-based algorithm, however, is limited by its exponential dependence on the number of rotamer combinations considered. In the case of active sites with four or more active site residues, the algorithm performs poorly. Since it is not possible to use large rotamer libraries, the use of this algorithm is limited to a more coarse-grained search.

The RosettaMatch hashing method avoids the combinatorial explosion by treating each catalytic side chain independently in building up the hash table. It thus scales linearly with the number of rotamer combinations considered. Once the hash maps have been built up, the complexity of the look-up step is constant in time on average. In the worst case scenario (i.e., when many TS models placed in different boxes map to the same hash key), the hash look-up scales as $O(N)$, where N is the number of entries for the box. Although it is not easy to directly compare the complexity of the algorithm with Hellinga's Dezymer algorithm, the RosettaMatch hashing method has the advantage that the algorithm complexity depends only linearly on the number of residues making up the active site and the total number of rotamers used. In addition, as described in greater detail below, the RosettaMatch hashing method has been employed to develop synthetic enzymes for two unique reactions for which no natural enzyme exists, which is unprecedented.

The design methods disclosed herein, in their current form, can be used to design new active sites in existing scaffolds, based either on the structures of naturally occurring active sites or on chemical intuition; the speed of the methods makes it possible to search large sets of scaffolds for optimal active site placements. In the benchmark test, a number of the non-native designs have nearly perfect catalytic geometries and transition state binding energies as low or lower than the native match, and potentially represent viable enzymes. As an example, FIG. 10 shows a design for an aldolase active site built on a decarboxylase scaffold, with a calculated binding energy after design comparable to the native enzyme. The experimental evaluation of the activity of such high-ranking designs in non-native scaffolds will test the understanding of the mechanisms of enzyme catalysis.

To extend to new reactions for which natural enzymes provide less guidance, it should be very advantageous to use quantum chemistry-based techniques to compute transition states and ideal active site geometries. In particular, the "theozyme" concept developed by Houk and coworkers is complimentary to the techniques disclosed herein, as the coordinates of the theozyme can be used directly as input for the matching process.

Summary of Enzyme Design Methodology

Starting from an active site description comprising a TS model surrounded by appropriately placed protein functional groups (geometrical parameters are specified in FIG. 11 and Table 2 of FIG. 4), a set of protein scaffold candidates is searched to construct a catalytic site that binds tightly to the TS and retains the desired functional group geometry. The design process includes four steps (see FIG. 2). In step 1, a list of scaffolds is searched for positions that can hold the TS model and catalytic residues in the correct orientation. As noted above, two different hashing methods can be used to implement this step; an inside-out hashing method, based on the inverse rotamer tree technique, and an outside-in hashing method called RosettaMatch.

In step 2, the TS model and the catalytic side chains placed in step 1 are refined to eliminate clashes and optimize the catalytic geometry. In step 3, the identity and conformations of amino acid residues located near the active site are optimized using a software module referred to as RosettaDesign. Finally, in step 4, the designs in step 3 are ranked based on the computed TS binding energy, considering only designs where the catalytic constraints are satisfied. This combination of transition state stabilization with catalytic residue geometry is referred to herein as the predicted catalytic efficacy throughout. However, it should be emphasized that determination of the catalytic efficacy of a design requires experimental characterization.

Step 1: Geometry-Based Site Identification

The idea of the inverse rotamer tree (the first hashing technique noted above) is to convert the description of the active site in terms of functional groups into a description in terms of protein backbone coordinates, which can then be used to search a set of protein scaffolds, or to guide de novo scaffold design. This technique is the inverse of the standard side chain packing problem, in which the positions of the backbone coordinates are known. The algorithm employs a standard rotameric description of the side chains to solve the problem (Dunbrack and Cohen 1997); but, rather than building outward from the backbone coordinates, the side chains are grown backward from the functional group positions that are placed around the TS model in positions optimal for catalytic functionality. This approach generates an inverse rotamer tree specifying the possible placements of the protein backbone around the TS model that are compatible with the specified active site, in the sense that the relevant amino acids can be placed to achieve the desired active site geometry. FIG. 12 shows an exemplary inverse rotamer tree generated for the DERA active site. Once the inverse rotamer tree has been built, each combination of backbone coordinates for the catalytic residues is searched against the set of scaffolds (a step subsequently referred to as matching) using a geometric hashing-based approach.

Given the set of scaffolds to be searched, the first hashing algorithm begins by building a multiple key hash table. The backbone coordinates (N, Ca, C) for each pair of residues for each scaffold are mapped onto a unique key that is computed from the Ca-Cb distance and the [Ca, Cb] vector orientations. For enhanced speed, all the scaffolds are mapped into a single hash in memory at the beginning of the program. Each combination of backbone atom coordinates from the inverse rotamer tree is matched against the backbone distances and orientations stored in the hash table using a sub-graph isomorphism algorithm similar to that described by Russell (1998). Matches are ranked based on their structural similarity (in RMSD) to the specified active site geometry and the absence of atomic clashes between the TS model, the placed catalytic side chains, and the protein backbone.

The RosettaMatch Approach

The idea of this approach is to build forward from the protein backbone to the TS model for each catalytic side chain independently, and then to identify TS placements compatible with placement of each catalytic residue. The method includes ligand orientation, as well as center of mass coordinates. The following first describes the storage of the position of the TS model for each catalytic side chain rotamer placed at each position using a hash table and next, the processing of the hash table to extract sets of positions compatible with the specified active site geometry. Finally, performance enhancements to the method using pre-computed grids to restrict TS placement to clefts and pockets in the scaffolds, and to speed up the evaluation of atomic clashes with the protein backbone are discussed.

For each protein scaffold, a set of potential active site positions is predefined, either all positions in the protein, or positions lining cavities or small molecule binding sites. For each amino acid residue in the catalytic site description, all rotamers from the Dunbrack backbone dependent library are placed at each position. If there is no clash with the protein backbone, the TS model for the reaction is positioned as specified in the catalytic site definition. For catalytic side chain-TS interactions such as hydrogen bonds, where there are many chemically equivalent interaction geometries, a large set of TS model placements are considered; the fineness of the sampling around the varying degrees of freedom (the side chain-TS dihedral in the hydrogen bonding case) is specified in Table 2 (FIG. 4). Each TS rigid body placement is represented by [v, q], where v is the vector of the coordinates of the center of mass (x, y, z) of the TS model, and q is the unit quaternion (q1, q2, q3, q4) associated with the rotation that moves the TS model from a reference frame to its current placement. TS model placements are recorded in a hash table if there are no clashes with the protein backbone or the catalytic side chain using the key K computed as follows:

$$k(x, y, z, q_1 + q_2, q_3 + q_4) = l(x, y, z, q_1 + q_2, q_3 + q_4) \bmod N_h \quad (1a)$$

$$l(c_1, c_2, \ldots, c_m) = \sum_{1 \le i \le m} \left\lfloor \frac{c_i - c_{i0}}{d_i} \right\rfloor \cdot \prod_{j<i} N_j \quad (1b)$$

where the bracket is the integer part, $N_h$ is the expected size of the hash, $c_i$ is the coordinate in direction i, $c_{i0}$ is the origin for the direction i, $d_i$ is grid spacing for each direction, and $N_j$ is the total number of grid points in direction j.

For each placement of the TS model, the following information is stored in the hash table at the position identified by the key K: the box coordinates ($c_1, \ldots, c_7$) in which the TS model falls, the position in the protein sequence, the residue type (e.g., His, Asp, etc.), the index of the rotamer in the backbone dependent library, and the rigid body orientation of the TS model [v, q]. The position in the hash does not suffice to specify the TS position because the hash operator cannot be inverted.

For each key K, one list per catalytic residue is kept that records all the information described above for each TS model that hashed with the key K. Each key of the hash table (corresponding to each discrete box of the six-dimensional space) thus contains N lists, where N is the number of residues making up the catalytic site. If at least one of the N lists is empty, a catalytic site with the specified geometry does not exist for the corresponding TS model location. If the N lists are all not empty, a complete active site can be generated, and every combination of catalytic residues, for which there are no significant atomic clashes between the catalytic side chains and no two residues originate in the same backbone position, are selected for subsequent minimization and design as described below.

Finding the active site matches requires on the order of 15 minutes of processing time per scaffold on a computer using an Intel Corporation Xeon™ processor running at 2.8 GHz with 2 GB of RAM, with no diversification for the three-residue active site for type II aldolase. The runs take about 2 hours on the same machine with full diversification of the free degrees of freedom for the same active site. In addition, the RosettaMatch method is easily amenable to parallelization by splitting the pocket into different spatial regions and distributing the building of the hash table among different processors.

To focus the design calculations on promising regions of the scaffold, the center of mass of the TS model may be restricted to clefts or pockets that are likely to be large enough to comprise a viable active site. A square grid box is first constructed that covers the regions targeted for active site design. This grid is then trimmed to remove all the grid points that are <2.25 A from any protein backbone atom. Any residue on the protein backbone that has a Ca-Cb vector pointing toward one of those grid points and a Ca<3.5 A from any grid point is then included in the set of active site positions. In practice, the use of the grid does not substantially reduce the number of matches found, but it considerably speeds up the search process by eliminating regions unlikely to contribute high ranking active site designs.

To speed up the evaluation of clashes between the TS model and the protein backbone, a "backbone" grid is constructed that contains points that are <2.25 A from any backbone atom. TS model placements for which atoms overlap the backbone grid are not included in the hash.

Step 2: Optimization of Catalytic Site Placement in the Scaffold

For each match found with the inverse rotamer tree or the RosettaMatch method, residues around the TS model, other than the catalytic residues, are truncated to glycines. Further studies involve the modification of truncation to alanine (Ala), which may result in enzymes that are easier to handle. The initial placements of the TS model and catalytic side chain conformations are optimized by rigid body minimization followed by side chain minimization using Rosetta (Gray et al. 2003; Wang et al. 2005). The potential used for minimization consists of the repulsive part of a standard Lennard Jones 6-12 potential (Kuhlman and Baker 2004), a side chain torsional statistical potential (Dunbrack and Cohen 1997) complemented by a "virtual energy" term that describes the extent to which the functional groups on the catalytic side chains satisfy the ideal geometry described in the active site. The virtual energy term is a quadratic penalty function of the geometrical parameters that relate the functional groups of the catalytic residues to the TS (FIG. 11). Minimization is carried out multiple times using Powell's method (Flannery et al. 2002), gradually increasing the weight on the repulsive interactions between iterations. A very low value is used initially to avoid repulsion of the TS model from the active site.

Step 3: Sequence Optimization Around the TS Model

The minimization step leads to pockets in which a non-clashing TS model is placed with catalytic side chains positioned with functional atoms close to the optimal geometry required for catalysis. It is then necessary to design the surrounding, non-catalytic protein residues to maximally stabilize the transition state. The conformations and identities of residues surrounding the TS model are optimized using Monte Carlo simulated annealing as described previously (Kuhlman and Baker 2000). The potential includes (1) a 12-6 Lennard-Jones potential with an attenuated repulsive component (Kuhlman and Baker 2004), (2) an implicit solvation model (Lazaridis and Karplus 1999), (3) an orientation-dependent hydrogen bonding term (Kortemme and Baker 2002; Kortemme et al. 2003, 2004; Jiang et al. 2005), (4) a Coulomb model with a distance dependent dielectric constant, (5) a pair potential derived from the Protein Data Bank (Simons et al. 1999) that captures features of side chain side chain electrostatics, and (6) a backbone dependent side chain torsional potential derived from known structures (Dunbrack and Cohen 1997). This potential has performed very well in protein-small molecule docking calculations (Meiler and Baker 2006).

Step 4: Design Ranking Based on Binding Energy and Catalytic Geometry

Step 4 simply uses existing techniques to rank the sequences providing the required backbone based on binding energy and catalytic geometry and applying filters based on known binding interactions.

Design of a Synthetic Enzyme for a Retro-Aldol Reaction

As noted above, the enzyme design techniques disclosed herein have been empirically tested to provide alternative configurations of naturally occurring enzymes, as well as to provide enzymes for reactions where there is no naturally occurring enzyme counterpart. Synthetic enzymes for both Kemp elimination and retro-aldol reactions have been studied. The following provides a description of how the concepts disclosed herein can be used to design novel catalysts for a retro-aldol reaction, in which a carbon-carbon bond is broken in a non-natural (i.e., not found in biological systems) substrate (i.e., in 4-hydroxy-4-(6'-methoxy-2'-napthalene)-2-butanone; FIGS. 13A-13C).

FIG. 13A schematically illustrates the retro-aldol reaction. FIG. 13B schematically illustrates a general description of the aldol reaction pathway using an active imine (Schiff-base) lysine and general acid/base chemistry. FIG. 13C schematically illustrates active site motifs utilizing quantum mechanically optimized structures. In Motif I, two lysines are positioned near one another to facilitate a shift in pKa of the intended nucleophilic lysine, while a Lys-Asp dyad acts as the base to deprotonate the hydroxyl group. In Motif II the catalytic lysine is buried in a hydrophobic environment to lower its pKa so as to function as a potent nucleophile, while a tyrosine functions as a general acid/base. In Motif III the catalytic lysine, analogous to Motif II, is placed in a hydrophobic pocket to alter its pKa, while a His-Asp dyad serves as a general base similar to the catalytic unit commonly observed in the serine proteases. In Motif IV, the catalytic lysine is again positioned in a hydrophobic environment. Additionally, an explicitly-modeled bound water molecule is placed such that it forms a hydrogen bond with the carbinolamine hydroxyl during its formation, aids in the water elimination step, and deprotonates the β-alcohol at the C—C bond breaking step. Hydrogen bond donor/acceptors, such as Ser, Thr, or Tyr, are placed to position the water molecule in a tetrahedral geometry over the β-alcohol and the carbinolamine hydroxyl. A basic residue makes hydrogen bonds to this water molecule to increase its proton abstraction ability. For each of the four motifs, where possible, additional hydrogen-bonding interactions were designed to stabilize the carbinolamine hydroxyl group and an aromatic side chain was placed to optimally pack along the planar aromatic moiety of the substrate.

As discussed above, the first step (see block 12 of FIG. 1) in the computational design of an enzyme is to define one or more potential catalytic mechanisms for the desired reaction, and then to design idealized active sites consisting of a transition state model surrounded by protein functional groups in positions optimal for catalysis. For the retroaldolase-catalyzed decomposition of the napthyl-butanone substrate, it was decided to focus on mechanisms involving enamine catalysis by lysine via a Schiff-base, or imine intermediate; as shown in simplified form in FIG. 13B. The reaction proceeds in a number of distinct steps, each of which requires both acid and base catalysis, which may be provided by amino acid side chains or water molecules. First, a nucleophilic attack of lysine on the ketone of the substrate forms a carbinolamine intermediate, which eliminates a water molecule to form the imine/iminium species, followed by carbon-carbon bond cleavage triggered by the de-protonation of the β-alcohol with the iminium acting as an electron sink, and finally hydrolysis of the enamine to release the covalently bound product and free the enzyme for another round of catalysis.

The second step of the design process (see block 14 of FIG. 1) is the identification of protein scaffolds that can accommodate the designed transition state ensemble described above. To take into account the multi-step reaction pathway, the enzyme design methodology disclosed herein was extended to allow design of sites simultaneously compatible with multiple transition states and reaction intermediates, referred to as a composite TS. Using this technique, design models were generated using the four catalytic motifs shown schematically in FIG. 13C, which employ different constellations of catalytic residues to facilitate carbinolamine formation and water elimination, carbon-carbon bond cleavage, and release of bound product.

In a representative active site search, a total of 181,555 matches for the catalytic residues were found in the 71 different scaffolds from the PDB searched. Following optimization of the composite TS rigid body orientation and the identities and conformations of the surrounding residues (see block 16 of FIG. 1), 343 of these had favorable TS binding energy and satisfied the catalytic constraints. A total of 72 designs with 10-20 amino acid identity changes in 10 different scaffolds were selected for experimental characterization based on the predicted TS binding energy, the extent of satisfaction of the catalytic geometry, the packing around the active lysine, and the consistency of side chain conformation after side chain repacking in the presence and absence of the TS model (see block 18 of FIG. 1). Genes encoding the designs were synthesized and the proteins were expressed and purified from *E. coli*; soluble purified protein was obtained for 70 of 72 of the expressed designs (see block 20 of FIG. 1).

Retro-aldolase activity was monitored using a fluorescence-based assay of product formation for each of the designs and the results are summarized in Table 5 (FIG. 14). The initial 12 designs utilized the first active site shown in FIG. 13C, which involves a charged side chain (LysAspLys) mediated proton transfer scheme resembling that in DERA aldolases. Of these, two designs showed slow enaminone formation with 2,4-pentandione, indicative of a nucleophilic lysine, but none displayed retro-aldolase activity. Ten designs were made for the second, much simpler active site shown in FIG. 13C, which involves a single imine forming lysine in a hydrophobic pocket as in aldolase catalytic antibodies; of these, one formed the enaminone conjugate, but none were catalytically active. The third active site incorporates a His-Asp dyad as a general base to abstract a proton from the β-alcohol; of the 14 tested, 10 demonstrated stable enaminone formation and eight had detectable retro-aldolase activity. In the final active site, variations with the explicit modeling of a water molecule were implemented, positioned via side chain hydrogen bonding groups, which shuttles between stabilizing the carbinolamine and abstracting the proton from the hydroxyl. Of the 36 designs tested, 20 formed the enaminone, and 23 (with 11 unique positions for the catalytic lysine) had significant retro-aldolase activity, with rate enhancements up to four orders of magnitude over the uncatalyzed reaction.

The active designs occur on five different protein scaffolds belonging to the TIM barrel and jelly roll folds. Progress curves (FIG. 15A) show a range of kinetic behaviors: in some cases (RA45), there is a pronounced lag phase, likely associated with slow Schiff-base formation, in others, (RA61), there is little or no lag, and for a third set (RA22) there is an initial burst followed by a slower steady state rate. It is notable that the simple linear kinetics are observed for the designs in the relatively open jelly roll scaffold, while the more complex kinetics are observed for the TIM barrel designs which have more enclosed active site pockets that may restrict substrate access and product release. Reaction velocities were extracted from the steady state portions of the progress curves and assume simple Michaelis-Menten kinetics to obtain $k_{cat}$ and $K_M$ estimates for several of the best enzymes (FIG. 15B). Given the simplifications, these are better viewed as phenomenological quantities rather than rate constants in a particular kinetic model. Importantly, the most active designs exhibited multiple turnover kinetics; the linear progress curves for designs RA60 and RA61, for example, continue unchanged for more than 20 turnovers.

Referring to FIG. 15A, progress curves for RA61, RA61K176M, RA45, RA45E232T, and RA45K179M are graphically illustrated. The enzymes were tested at 540 μM of the racemic substrate; the reaction was followed by measuring the appearance of the fluorescent product ($\lambda_{ex}$ of 330 nm, $\lambda_{em}$ of 452 nm).

Referring to FIG. 15B, the rate of product formation is plotted against the initial substrate concentration. The rates are reported in Table 6 in FIG. 16. Reaction conditions for all experiments were 25 mM HEPES, 2.7% $CH_3CN$ pH 7.5, and substrate at the reported concentration.

The apparent $k_{cat}$ and $K_M$'s for the active designs measured using racemic substrate are given in Table 6 (FIG. 16); $k_{uncat}$ was determined from measurements of the reaction progression in the absence of enzyme and is close to previously determined values. The ratio of $k_{cat}/k_{uncat}$ for the best designs using racemic substrate is $2\times10^4$. The catalytic proficiency of the designs is far from naturally occurring enzymes with a $k_{cat}/K_M$ on the order of 1 (Table 6 in FIG. 16); the very low $k_{cat}$ is probably associated with low reactivity of the imine-forming lysine. Rate enhancements for all the active designs are reported in Table 7 in FIG. 17. For each of the 11 catalytic lysine positions, a "knock-out" mutation to methionine dramatically decreased the activity or, more commonly, abolished catalysis completely, verifying that the observed activity was due to the designed active site. The pH dependence of the designed enzyme activities is consistent with a pKa perturbation of the catalytic lysine, normally around 10, to about 5-6.

Design models for several of the most active designs using catalytic Motif IV are shown in FIG. 18A-18E. Design RA60 is on a jelly roll scaffold, and RA45 and RA46 are on a TIM barrel scaffold. The Schiff-base-forming lysine, the hydrogen bonding residues coordinating the bridging water molecules, and the designed hydrophobic pocket that binds the aromatic portion of the substrate are clearly evident in all three designs. These Figures are examples of design models for active designs highlighting groups potentially important for catalysis. The imine lysine is in orange, the transition state model is in yellow, hydrogen bonding groups are in light green, and the putatively catalytic water is shown explicitly. The designed hydrophobic binding site for the aromatic portion of the transition state model is indicated by the gray mesh. Note that the original Figures were in full color, while the Figures presented herein are grayscale Figures with textual labels identify previously colored portions.

Referring to FIG. 18A: designed enzyme RA60 has a rate enhancement of $10^4$ and is built using catalytic Motif IV on the jelly roll scaffold; the catalytic Lys 48 and the aromatic moiety of the substrate is well packed by Trp46, Trp121 and other surrounding hydrophobic residues; Tyr78, Tyr119, Ser87, Ser89 and Ser135 form a hydrogen bonding network with the bridging water molecule and the composite TS.

Referring to FIG. 18B: design RA46 has a rate enhancement of $10^3$ and is built by embedding catalytic Motif IV on a TIM barrel scaffold; the imine-forming Lys 180 is high in the barrel allowing easy substrate access, but still being well-packed in a relatively hydrophobic environment; Tyr83 and Ser210 interact with the bridging water molecule, which facilitates the proton shuffling required in active site IV.

Referring to FIG. 18C: design RA45, which has a rate enhancement of almost $10^4$, is built on the same TIM barrel scaffold taking advantage of a different binding mode; the bridging water is hydrogen bonded by Ser211 and Glu233. Replacing the Glu with Thr decreases catalytic activity three-fold (see FIG. 15A), demonstrating the importance of the water and hydrogen bond network.

FIGS. 18D and 18E illustrate overlay of the design model (purple) on an X-ray crystal structure (green). Designed amino acid side chains are shown in stick representation, and the TS model in the design is shown in yellow.

Referring to FIG. 18D: design RA22 achieves rate enhancements of $10^3$-$10^4$ and was built by embedding catalytic Motif III on a TIM barrel scaffold. The X-ray structure of variant S210A (which is 20-fold less active (FIG. 2A) at 2 Å resolution) was solved.

Referring to FIG. 18E: design RA61 achieves rate enhancements of $10^4$ and was built by embedding catalytic Motif IV on a jelly roll scaffold. The crystal structure of variant M48K was successfully solved, which has activity similar to RA61. The designs are in excellent agreement with the crystal structures (Cα RMSD=0.62 Å and 0.46 Å, respectively; the designed side chain RMSD=0.60 Å and 0.40 Å). Small differences are seen in the high-resolution details of packing around the active site due to slight movements in some of the loops above the binding pocket, and two rotamer changes in RA61 that may reflect the absence of a transition state analogue in the crystal structure.

To evaluate the accuracy of the design models, the structures of two of the designs were solved by X-ray crystallography (FIGS. 18D and 18E). The 2.2 Å resolution structure of the Ser210Ala variant of RA22 (FIG. 18D) shows that the designed catalytic residues Lys159, His233, and Asp53 superimpose well on the original design model, and the remainder of the active site is nearly identical to the design. The 1.9 Å resolution structure of the M48K variant of RA61 likewise reveals an active site very close to the design model, with only His46 and Trp178 in alternative rotamer conformations, perhaps due to the absence of substrate in the crystal structure (FIG. 18E). Both crystal structures differ most significantly from the designs in the loops surrounding the active site. Explicitly incorporating backbone flexibility in these regions during the design process could yield improved enzymes.

These results demonstrate that novel enzyme catalysts for non-natural reactions can be created using computational enzyme design. The success with the retro-aldol reaction is notable because of the complexity and large number of steps in the reaction. The enzyme design methodology used here is immediately applicable to other multi-step reactions. While the designs are less active than aldolase catalytic antibodies, they should be excellent starting points for generating improved catalysts using directed evolution due to their relatively small size and the robustness of the scaffolds which should allow for increased expression, easier purification, and library synthesis, etc. The more constrained designed active sites are also likely to have different substrate selectivities. For example, the highly reactive enaminone-forming lysine in the catalytic antibody combines rapidly with both the retro-aldol substrate and the diketone probe, despite their very different structures, whereas many of the designs with considerable retro-aldolase activity interact very slowly or not at all with the diketone supporting material.

The success in computational design of enzyme catalysts for the retro-aldol reaction is due at least in part to the fortunate convergence of three relatively independent advances in recent years: (1) the development of improved computational protein and enzyme design methodology, (2) the rapid growth in the power of computers, and (3) advances in gene synthesis and protein production methodology. The multi-step enzyme design methodology disclosed herein has been made publicly available in two software modules, RosettaMatch and RosettaDesign. These modules are clearly critical, but the success of the method also depends on large scale sampling and refinement of many potential design starting points (an average of 30,000 CPU hours per active site motif) and the availability of low cost and rapid gene synthesis capability, which facilitates the experimental testing of many designs for each of four different enzyme active site types in a wide range of protein scaffolds.

With the capability of generating and experimentally screening large numbers of computational enzyme designs, each proposed catalytic mechanism can be treated as an experimentally testable hypothesis to be tested by multiple independent design experiments. The lack of success with the first active sites tested for the aldol-reaction enzyme contrasts strikingly with the relatively high success rate with the active site in which proton shuffling is carried out by a bound water molecule rather than amino acid side chains to serve as the acid/base catalyst. The charged polar networks in highly optimized naturally occurring enzymes require exquisite control over functional group positioning and protonation states, as well as the satisfaction of the hydrogen bonding potential of the buried polar residues, which leads to still more extended hydrogen bond networks. Computational design of such extended polar networks is exceptionally challenging due to the difficulty of accurately computing the free energies of buried polar interactions, particularly the influence of polarizability on electrostatic free energies and the delicate balance between the cost of desolvation and the gain in favorable intraprotein electrostatic and hydrogen bonding interactions. The sampling problem also becomes increasingly formidable for more complex sites. The side chain identity and conformation combinatorics dealt with by hashing in RosettaMatch becomes intractable for sites including five or more long polar side chains, which for accurate representation, may require as many as 1000 rotamer conformations each. At the other extreme, bound water molecules offer considerable versatility as they can readily reorient to switch between acting as hydrogen bond acceptors and donors and involve neither delicate free energy tradeoffs, nor intricate interaction networks.

It is tempting to speculate that the admittedly primitive computationally designed enzymes and primordial enzymes that arose early in evolution resemble one another more than they resemble highly refined and sophisticated modern day enzymes. The ability to design simultaneously only 3-4 catalytic residues parallels the infinitesimal probability that early in evolution, more than 3-4 residues would have happened to be positioned appropriately for catalysis. Some of the functions played by exquisitely positioned side chains in modern enzymes may have been played by water molecules earlier in evolution. Whether this analogy is correct in detail, it will likely be possible to develop increasingly powerful aldol catalysts by improving on the robust and stable designs described herein, both by incorporating additional backbone flexibility into the design process, particularly in loop regions, to increase the reactivity of the imine-forming lysine and to lower $K_m$ by making possible tighter substrate and transition state binding, and by using directed evolution for more subtle fine-tuning further from the active site.

While these aldol enzyme results demonstrate that novel enzyme activities can be designed from scratch and indicate the catalytic strategies most accessible to nascent enzymes, there is still a very significant gap between the activities of these designed catalysts and those of naturally occurring enzymes. Narrowing this gap presents an exciting prospect for future work: the close agreement between the two crystal structures and the design models gives credence to the strategy of testing hypotheses about catalytic mechanisms by generating and testing the corresponding designs; indeed, almost any idea about catalysis can be readily tested by incorporation into the computational design procedure. Determining what is missing from the current generation designs and how it can be incorporated into a next generation of more active designed catalysts will be an exciting challenge that should unite the fields of enzymology and computational protein design in the years to come.

Summary of Aldol Reaction Enzyme Design

Novel retro-aldolases that catalyze the breaking of a carbon-carbon bond in a non-natural substrate were designed using the techniques disclosed herein. Using such techniques, computationally designed enzymes employing four different catalytic site motifs were designed, and a total of 72 designs were experimentally tested using a streamlined protein production process. 32 of the designs spanning a wide range of protein folds had easily detectable retro-aldolase activity. The attached Sequence Listing details 31 of these sequences (RA44 proved to be a difficult protein to work with, and is not present in the Sequence Listing even though it showed some signs of enzymatic activity). Designs utilizing an active site involving an explicit water molecule mediating proton shuffling were significantly more successful, with rate accelerations of up to four orders of magnitude and multiple turnovers, than those involving polar side chain networks. The success with incorporating explicit water molecules into the designed sites may have a parallel in early enzyme evolution, with water mediated interactions gradually replaced by the more complex polar side chain networks in modern enzymes. The atomic accuracy of the design process was confirmed by the X-ray crystal structure of active designs embedded in two different protein scaffolds, both of which were nearly super imposable on the design model.

Design of a Synthetic Enzyme for Kemp Elimination

This section describes use of the computational enzyme design methodology disclosed above to create novel enzyme catalysts for an exemplary reaction for which no naturally occurring enzyme exists, i.e., the Kemp elimination. The reaction, shown in FIG. 19, has been extensively studied as a model system for understanding the catalysis of proton abstraction from carbon—a process that is normally restricted by high activation energy barriers.

FIG. 19 illustrates the reaction scheme of the Kemp elimination. The reaction proceeds via a single transition state, which is stabilized by a base deprotonating the carbon and the dispersion of the resulting negative charge through π-stacking interactions. A hydrogen bond donor is also used to stabilize the partial negative charge on the phenolic oxygen.

FIG. 20 shows examples of active site motifs highlighting the two choices for the catalytic base—a carboxylate or a His-Asp dyad—employed for deprotonation, and a stacking aromatic residue for transition state stabilization. For each base, all combinations of hydrogen bond donor groups (Lys, Arg, Ser, Tyr, His, water or none) and π-stacking interactions (Phr, Tyr, Trp) were used as active site motifs.

The first step in the protocol for designing novel enzymes disclosed herein is to choose a catalytic mechanism. Next, quantum mechanical transition state calculations are employed to create an idealized active site with protein functional groups positioned so as to maximize transition state stabilization (FIG. 20). The key step for the Kemp elimination is de-protonation of a carbon by a general base. In this study, two different catalytic bases were selected for this purpose: (1) the carboxyl group of an aspartate or glutamate side chain, and (2) the imidazole of a histidine positioned and polarized by the carboxyl group of an aspartate or glutamate (in the following discussion this combination is referred to as a His-Asp dyad). The two choices have complementary strengths and weaknesses. The pKa of the carboxylate groups on aspartate and glutamate must be raised in order to make the group a more effective general base. This goal can be achieved by burial of the carboxylate group in the apolar environment of the protein. However, burying the charged carboxylate group confers a desolvation penalty, both on the free energy of folding of the protein and on the free energy of substrate binding. While histidine is a better general base than a carboxylate, it is necessary to regulate both its pKa and its tautomeric state. Coupling the histidine with a base such as aspartate in a dyad serves to both position the histidine and increase its basicity. If the pKa of histidine is raised too high, however, it can become doubly protonated, rendering it ineffective as a base.

For both the carboxylate and histidine-based mechanisms, additional functional groups have been included in the idealized active sites to further facilitate catalysis using both quantum mechanical and classical methods. A hydrogen bond donor was employed to stabilize the developing negative charge on the phenolic oxygen in the otherwise hydrophobic active site. Catalytic motifs lacking the H-bond donor were also tested, since the partial negative charge of the phenolic oxygen is relatively weak in the transition state of the target substrate and can be easily solvated by water, and potential interactions of an H-bond donor could reduce the activity of the catalytic base. For each choice of catalytic site composition, density functional theory (DFT) quantum mechanical methods were used to optimize the placement and orientations of the catalytic groups around the transition state for maximal stabilization. Finally, since stabilization of the transition state by charge delocalization is a key factor in catalysis of the Kemp elimination, it was decided to stack aromatic amino acid side chains on the planar transition state (FIG. 20) using idealized π-stacking geometries.

Next, the RosettaMatch hashing algorithm was used to search for constellations of protein backbone positions capable of supporting these idealized active sites in a large set of stable protein scaffolds with ligand binding pockets and high-resolution crystal structures. The His-Asp dyad required generalizing RosettaMatch to handle side chains, such as the Asp, whose range of allowed positions are referenced to another catalytic side chain rather than to the transition state. This step was accomplished by identifying, for each His rotamer in a scaffold, the set of Asp rotamers that can provide the supporting hydrogen bond. The scaffold set spans a broad range of protein folds, including TIM barrels, β-propellers, jelly rolls, Rossman folds and lipocalins amongst others (Table 8 in FIG. 21). In a typical search, over 100,000 possible realizations of the input idealized active site were found in the scaffold set. For each of these "matches," gradient-based minimization was used to optimize the rigid body orientation of the transition state and the geometry of the catalytic side chains. Subsequently, residues surrounding the transition state were redesigned to both maximize the stability of the active site conformation and transition state binding as well as to maintain protein stability using the treatment of ligands in the Rosetta design methodology. Designs were then ranked based on the catalytic geometry and the computed transition state binding.

A steady enrichment of the fraction of designs in TIM barrel scaffolds was observed throughout the enzyme design process. 25% of the proteins in the input scaffold set, 43% of the initial matches, and 71% of the low energy designs were in TIM barrel scaffolds. Inspection of the designs suggests that the TIM barrel binding pockets were favored because of the large number of takeoff positions (all positions around the barrel pointing towards the cavity) for both the catalytic residues and the additional transition state binding and stabilizing residues optimized in the design process. The former favored TIM barrel matches, and the latter favored low energy designs in TIM scaffolds. The TIM barrel is the most widespread and catalytically diverse fold in naturally occurring enzymes; the present in silico design process appears to be drawn toward the same structural features as naturally occurring enzyme evolution.

Following the active site design, a total of 59 designs in 17 different scaffolds were selected for experimental characterization. Of the 59 designs, 39 utilize an Asp/Glu as the generalized base and 20 use a His-Asp/His-Glu dyad. Eight of the designs showed measurable activity in Kemp elimination assays in an initial activity screen (Table 8 in FIG. 21, see Supplementary Table 9 in FIG. 22 for sequence information and supplementary information for experimental details). For each of these eight designs, mutation of the catalytic base (to Ala or Gln/Asn) drastically decreased the activity or abolished catalysis completely, verifying that the observed activity was due to the designed active site (Table 8 in FIG. 21; for some examples see FIG. 23A). $k_{cat}/K_M$ values in the range of 6 to 160 $M^{-1}s^{-1}$ were observed (Table 8 in FIG. 21 and FIG. 23B). However, saturation kinetics could not be obtained for all designs (for example see KE10 and KE61 in FIG. 23B), due to low substrate solubility. Both catalytic motifs were used in active designs, and of the two most active catalysts, which show a rate acceleration of roughly $10^5$ and a $k_{cat}/K_M$ of about 100, one employs the Glu as the base and the other employs the His-Asp dyad.

FIGS. 23A and 23B provide kinetic characterization of selected ones of the designed catalysts. Product formation over time for KE59 (open circles) and KE70 (filled circles) is depicted in FIG. 23A. The product concentration is normalized by the catalyst concentration, which corresponds to the number of turnovers. By deleting the catalytic base in both designs, the catalysts become inactive (open and filled triangles). Mutating Asp44 of the catalytic dyad of KE70 to Asn reduces activity 2.5-fold. Michaelis-Menten plots for a representative selection of designed catalysts are shown in FIG. 23B). Some designs (KE10 filled triangle) show no saturation up to the maximal substrate solubility.

Models for these two most active designs are shown in FIGS. 24A and 24B. In the KE59 design (FIG. 24A), which is in a TIM barrel scaffold, Glu231 is the catalytic base, and Trp110 facilitates charge delocalization by π-stacking to the transition state. Additionally, Leu108, Ile133, Ile178, Val159, and Ala210 create a tightly packed hydrophobic pocket that envelops the non-polar substrate. Polar residues Ser180 and Ser211 provide hydrogen-bonding interactions with the nitro group of the transition state. Mutation of the catalytic base Glu231 to Gln abolished catalytic activity (Table 8 in FIG. 21 and FIG. 23A-open triangles). Attempts to add a hydrogen bond donor to stabilize the negative charge developing at the phenolic oxygen through a Gly131 to Ser mutation reduced $k_{cat}/K_M$ 9-fold (Table 8 in FIG. 21), perhaps due to unfavorable electrostatic interactions between the oxygen atoms on the serine and substrate. This large effect suggests that the transition state binding site is quite well defined.

The KE70 design (FIG. 24B) employs the His-Asp dyad mechanism. Asp44 positions and polarizes His16 so as to optimally deprotonate the proton from the substrate. Tyr47 π-stacks above the transition state, and together with Ile201, Ile139, Val167, Ala18, Ala102, and Trp71 create a tight hydrophobic pocket around the transition state. The active site is again in a TIM barrel scaffold, with the His-Asp dyad near the bottom of the site. Mutation of the catalytic base His16 to Ala abolished catalytic activity (Table 8 in FIG. 21 and FIG. 23A—filled triangles) while mutating Asp44 of the catalytic dyad to Asn produced roughly a 2.5-fold reduction (Table 8 in FIG. 21 and FIG. 23A—filled squares). In another design using a His-Asp dyad as general base, KE71, the analogous Asp to Asn mutation reduced activity 6-fold (Table 1 in FIG. 3), while the His to Ala mutation abolished catalysis (Table 1 in FIG. 3). All designs exhibited multiple turnovers (≥7)—a prerequisite for efficient catalysis.

FIGS. 24A and 24B illustrate computational design models of the two most active catalysts. FIG. 24A schematically illustrates KE59, which uses the indole-3-glycerolphosphate synthase from *Sulfolobus solfataricus*, a TIM barrel protein, as the scaffold. The transition state model is almost completely buried, with loops covering the active site. The mostly hydrophobic residues in the active site pocket pack the transition state model tightly, providing a high transition state shape complementarity (SC=0.84). Polar residues Ser and Asn at the top of the pocket can interact with the nitro group of the transition state for binding. The key catalytic residues (Glu231 as base and Trp110 for π-stacking) are depicted in cyan. FIG. 24B schematically illustrates the deoxyribose-phosphate aldolase from *Escherichia coli*, another TIM barrel protein, as the scaffold for KE70. The shorter loops in this scaffold leave the active site pocket freely accessible for the substrate. The transition state is surrounded by hydrophobic residues, which provide high shape complementarity (SC=0.77). His16 and Asp44 constitute the catalytic dyad, while Tyr47 stabilizes the transition state through π-stacking interaction.

High-resolution structural information on designed proteins is essential to validate the accuracy of the design methodology. Crystals were grown to obtain a high-resolution structure of one of the early Glu-based designs, KE07. As shown in FIG. 25, the crystal structure and design model are virtually super imposable, with an active site (6.0 Å around the transition state) RMSD of 0.95 Å, mostly due to modest side chain rearrangements. The similarity between the design model and the crystal structure is important because it suggests that the active sites in the new enzymes are likely to be close to those in the corresponding design models. The subtle deviations are also important, since they also indicate loop regions where explicitly modeling backbone flexibility may yield improved designs.

FIG. 25 schematically illustrates a comparison of the crystal structure and the designed model of KE07. The crystal structure (cyan) was solved in the unbound state and shows only modest rearrangement of active site side chains compared to the designed structure (gray) modeled in the presence of the transition state (yellow, transparent; backbone RMSD for the active site is 0.32 Å vs. 0.95 Å for the active site including the side chains). KE07 contains 13 mutations compared to the starting scaffold (PDB code 1thf).

The crystal structure also revealed that Lys222 makes a salt bridge to the catalytic Glu101 in the absence of substrate, whereas in the designed model the ammonium of the lysine stabilizes the developing phenoxide in the transition state. Forming the productive transition state complex thus requires breaking the salt bridge. Hence, elimination of the salt bridge in the unbound state would be expected to improve catalysis. This prediction was tested by substituting the lysine with an alanine, and this substitution resulted in a 2.5 fold increase in $k_{cat}/K_M$ (Table 8 in FIG. 21).

In vitro evolution has been shown to dramatically improve the stability, expression, and activity of enzymes, and is currently the most widely used and successful approach for refining biocatalysts. However, in vitro enzyme evolution generally requires a starting point with at least a low level of the desired activity, which is then optimized by repeated rounds of mutation and selection. It was reasoned that in vitro evolution would be an excellent complement to the computational design efforts disclosed herein. The design calculations ensure that key catalytic functional groups are correctly positioned around the transition state, and, as demonstrated above, can generate active catalysts without requiring any starting activity. Thus, computational design can potentially provide excellent starting points for in vitro evolution. On the other hand, the design process does not explicitly model configurational entropy changes, longer range second shell interactions, and dynamics effects that can be important for efficient turnover, and these shortcomings can potentially be remedied by directed evolution. Directed evolution can be valuable both in improving the designed catalysts, and by shedding light on what is missing from the designs, leading to improvements in the computational design methodology.

To investigate the extent to which in vitro evolution methods can improve computationally designed enzymes, evolution experiments were performed on KE07, the early design for which the crystal structure was determined. Seven rounds of random mutagenesis, and shuffling (also including synthetic oligonucleotides that expanded the diversity at selected residues), followed by screens in microtiter plates, yielded variants that had 4-8 mutations relative to KE07 and an improvement of >200-fold in $k_{cat}/K_M$ (Table 9 in FIG. 22). Notably, the key aspects of the computational design, including the identities of the catalytic side chains, were not altered by the evolutionary process (indeed, mutating the catalytic base Glu101 abolished the catalytic activity of both the designed template and its evolved variants). Instead, the mutations were often seen in residues adjacent to designed positions (e.g., Val12, Ile102, and Gly202), and thus provide subtle fine-tuning of the designed enzyme. Some mutations, such as Gly202Arg, are likely to increase the flexibility of regions neighboring the active site. The hydrophobic residues Ile7 and Ile199, at the bottom of the active site were frequently mutated to polar residues (the most common mutation being Ile7Asp), which may hold Lys222 in position to stabilize the developing negative charge in the transition state while preventing interaction of Lys222 with Glu101. Consistent with this idea, the pKa of the catalytic Glu101 shifts from <4.5 to 5.9 in the evolved variant with the Ile7Asp mutation (FIG. 26). While the Lys222Ala mutation increases the activity of the original KE07, it significantly decreases the activity of the evolved variants perhaps due to the uncompensated additional negative charge.

FIG. 26 illustrates representative pH-rate profiles of KE07 variants. A $7^{th}$ round variant (R7 10/11 G) that carries the Ile7Asp mutation shows a $pK_a(k_{cat})$ value of 5.9±0.04. In contrast, a second generation variant (11/10D) that carries no mutations at the bottom of the active site shows no specific decrease in $k_{cat}$ down to pH 5, indicating a $pK_a(kcat) \leq 4.5$.

The dramatic increase in catalytic activity, and turnover (>1000 catalytic cycles were observed for the evolved variants), achieved through screening a relatively small number of variants (800-1600 clones per round) by molecular evolution standards bodes very well for future combinations of computational design and molecular evolution. In particular, the in vitro evolution of the most active of the computational designs, for example KE59 or KE70, has the potential to yield highly active catalysts for the Kemp elimination reaction.

The challenge of generating novel biocatalysts has led to several successful experimental strategies. In particular, the Kemp elimination comprises a well-defined model for catalysis of proton transfer from carbon—a highly demanding reaction and a rate-determining step in numerous enzymes. It has therefore been the subject of several attempts to generate enzyme-mimics, and models, such as catalytic antibodies, promiscuous protein catalysts, and enzyme-like polymers. The catalytic parameters of the designed-evolved novel enzymes described here are comparable to the most active catalysts of the Kemp elimination of 5-nitro-benzisoxazole described thus far, and provide further insights into the makings of an enzyme. Comparison with the catalytic antibodies highlights the major shortcoming of many of the designs noted above, that is, their relatively weak binding of the substrate. While the computational design methodology has the advantage of being able to explicitly place key catalytic residues, this capability may come at a cost of overall substrate/transition state binding affinity. Consistently achieving high transition state binding energies, and high turnover numbers, is a challenge currently approached by introducing scaffold backbone flexibility into the design process. This technique should enable the creation of higher affinity binding sites produced by more perfectly positioned constellations of binding and catalytic residues.

The results described herein show that the combination of computational enzyme design to create the overall active site framework for catalyzing a synthetic chemical reaction with molecular evolution to fine-tune and incorporate subtleties not yet incorporated in the design algorithms provides a powerful approach to create novel enzyme catalysts for the very wide range of chemical reactions for which naturally occurring enzymes do not exist. Equally importantly, computational design provides a critical testing ground for evaluating and refining an understanding of how enzymes work. For example, the results obtained show that the deprotonation of a carbon in the Kemp elimination can be effectively carried out by both carboxylate and imidazole bases, and demonstrates how catalytic efficiency can be refined by fine-tuning the environment around a catalytic residue. There has been much controversy over the mechanisms by which naturally occurring enzymes achieve their incredible catalytic prowess, for example, the role of enzyme dynamics and strong hydrogen bonds. These questions can be difficult to answer due to the complexity of the sites brought about by many millions of years of natural selection operating throughout the enzymes. In contrast, the much simpler computationally engineered sites can be very easily dissected and the importance of different contributions to catalysis explicitly tested by incorporating additional specifications into the design process.

Methods Summary Computational Design of Kemp Elimination Catalyst

The transition state was computed at the B3LYP/6-31G(d) level with either a carboxylate or imidazole moiety as the general base. Aromatic side chains were placed above and below the transition state using idealized π-stacking geometries. A 6D hashing procedure was applied to find transition state poses in a large set of protein scaffolds (Table 9 in FIG. 22) that were consistent with the catalytic geometry. Residues surrounding the catalytic side chains and transition state were repacked and redesigned to optimize steric, coulombic, and hydrogen bonding interactions with the transition state and associated catalytic residues. Models with optimal protein-transition state interactions were selected for experimental verification.

Experimental Characterization

The designed proteins were expressed in the cytoplasm of *Escherichia coli* (*E. coli*) and purified over a Ni-NTA column (Qiagen). The proteins were assayed for activity in 25 mM HEPES pH 7.25/100 mM NaCl with a final protein concentration of 1 μM to 10 μM using substrate dilutions from 1 mM to 11 μM. Initial rates normalized by the protein concentration were plotted against substrate concentration to determine $k_{cat}$, $K_M$, and $k_{cat}/K_M$ in at least three independent measurements. Fitted $K_M$ values above 1 mM (and their corresponding $k_{cat}$ values) are necessarily approximate.

In Vitro Evolution

The designed KE07 variant was subjected to seven rounds of directed evolution in vitro. Gene libraries were created by random mutagenesis using error-prone PCR with "wobble" base analogues dPTP and 8-oxo-dGTP and the Genemorph PCR mutagenesis kit (Stratagene), and by DNA shuffling of the most active variants. In certain rounds, shuffling also included the spiking of synthetic oligonucleotides that expanded the diversity at selected residues. Following mutagenesis, libraries were recloned into pET29b plasmid, transformed to E. coli BL21(DE3) cells, and plated on agar containing kanamycin. In each round, 800-1600 colonies were individually transferred to 96-well plates, grown in liquid medium containing kanamycin to OD-0.6, induced with 1 mM IPTG, and further grown for another five hours. Cell pellets were frozen overnight and lysed with HEPES pH 7.25 50 mM, 0.2% triton, 0.1 mg/ml lysozyme (250 µl/well). The cleared lysates were assayed for hydrolysis of 5-nitrobenzisoxazole (0.125 mM) by following the release of the phenol product at 380 nm. The most active clones were sub-cloned, sequenced, and the encoded plasmids were used as templates for subsequent rounds of mutagenesis and screening.

Synthetic Aldolases Disclosed Herein

As noted above, the computational design technique disclosed herein was employed to develop a number of synthetic enzymes for catalyzing aldol reactions (i.e., synthetic aldolases). These synthetic enzymes can be differentiated from naturally occurring aldolases in several ways. For example, the native or folded shape of some of the synthetic enzymes are readily distinguishable from the native or folded shape of the naturally occurring aldolases. For synthetic aldolases having a fold or three-dimensional shape in common with the naturally occurring aldolases, the relative locations of the active sites in the folded shapes of the synthetic aldolases are also readily distinguishable from the relative locations of the active sites in the folded shapes of the naturally occurring aldolases.

Naturally occurring aldolases include two distinct types. Type I aldolases include a Schiff-base (also referred to as an imine; the term Schiff-base being generally employed by biologists, biochemists, and enzymologists, while chemists generally employ the term imine) at the active site, and exhibit the characteristic TIM barrel shape (also referred to as an alpha-beta barrel shape). Type II aldolases include a metal complex at the active site, and also exhibit the TIM barrel shape. Significantly, there are no known naturally occurring aldolases that do not exhibit TIM barrel folding, or shape. Thus, one aspect of the concepts disclosed herein encompasses a synthetic aldolase having a protein fold other than the TIM barrel shape.

Another aspect of the synthetic aldolases disclosed herein encompasses synthetic aldolases exhibiting the TIM barrel fold and a Schiff-base (such as a lysine) at the active site, but have their active site in a position that is distinguishable from the positions of lysine active sites in naturally occurring aldolases.

TIM was the first enzyme identified exhibiting the alpha-beta barrel (or TIM barrel) protein fold, and the whole series of proteins exhibiting that fold is now named after it. TIM barrels are characterized by an internal ring of beta-strands (also referred to as beta-sheets) and an outer layer of alpha helices. The TIM barrel is by far the most commonly observed protein fold. Significantly, all naturally occurring aldolases exhibiting the TIM barrel fold and a lysine at the active site (i.e., Type I aldolases) have their active sites located on the end of beta strand 6. There is a single exception to this rule. Transaldolase has its active site in the beta 4 strand. A strand is a protein secondary structure which effectively comprises consecutive amino acids "lying flat" (the strand often twists or bends but there is still a flatness to the strand). A protein can have anywhere from none to several dozen beta strands in its structure. Beta strands are most interesting when they link together to form more complex structures (like barrels or jelly rolls). All secondary structures are numbered from the N-terminus of the protein (amino acid sequences are also numbered in this direction). The concepts disclosed herein thus encompass synthetic aldolases exhibiting the exhibiting the TIM barrel fold and a lysine at an active site at a location other than at the end of beta strand 6 or in the beta 4 strand.

Disclosed herein are specific protein sequences for 31 different synthetic aldolases, each of which is distinguishable from naturally occurring aldolases based on a different protein fold, or a different position of the active site. The synthesis of the specific sequences has been discussed above, and a detailed Sequence Listing for the 31 specific sequences is attached. It should be recognized that the computational design techniques disclosed herein will likely lead to the development of additional specific protein sequences representing additional synthetic aldolases. Further, additional research on the 31 different specific protein sequences disclosed herein will likely include inducing mutations (i.e., changes) into each of those 31 different specific protein sequences in an attempt to increase the effectiveness of the enzyme. Such mutations will not generally change the scaffold of the specific sequence. Thus, the concepts disclosed herein encompass not only the 31 different specific protein sequences disclosed herein, but rather (1) synthetic aldolases exhibiting the TIM barrel fold and a lysine at the active site, but which have their active site in a position that is distinguishable from the positions of lysine active sites in naturally occurring aldolases; and (2) synthetic aldolases exhibiting a fold other than the TIM barrel fold.

FIGS. 27A-27D can be used to help visualize these distinguishing features of the synthetic aldolases disclosed herein. FIG. 27A (Prior Art) graphically illustrates the characteristic TIM folded shape exhibited by many protein sequences, including all Type I naturally occurring aldolases. FIGS. 27B and C (Prior Art) graphically illustrate the characteristic location of the lysine active site for naturally occurring aldolases having the TIM folded shape, where the active lysine is disposed at the C-terminal end of the 6th beta strand (counting from the N-terminus, or first amino acid; the location being indicated by a dashed circle). While many of the synthetic aldolases disclosed herein exhibit the TIM folded shape, as will be discussed in greater detail below, the Schiff-base at the active site of the synthetic aldolases disclosed herein are located at positions that are very different from the active site positions of naturally occurring aldolases having the same folded shape.

FIG. 27D (Prior Art) graphically illustrates the characteristic jelly roll folded shape exhibited by some protein sequences. Significantly, some of the synthetic aldolases disclosed herein exhibit the jelly roll folded shape, whereas there are no known naturally occurring aldolases employing a lysine at the active site (i.e., Type I aldolases) exhibiting that folded shape.

FIG. 28 (Prior Art) graphically illustrates the lysine active site (indicated with a dashed circle) for naturally occurring aldolases having the TIM folded shape, showing that the active lysine is disposed in a pocket surrounded by side chains of other amino acids.

FIG. 29A graphically illustrates the lysine active site designed for synthetic aldolases according to one aspect of the concepts disclosed herein, where the active lysine is disposed in a similar pocket, however, care has been taken to reduce the side chains of other amino acids in close proximity of the active lysine. In particular, during the design process disclosed above, care has been taken to ensure that the active lysine is in a hydrophobic pocket and no negatively charged polar-side chain terminal oxygen atoms, particularly oxygen atoms from the carboxylate of aspartic acid or glutamic acid), are within about 7.5 angstroms of the epsilon ($\in$) nitrogen of the lysine (in other words, such atoms should be more than about 7.5 angstroms away, a distance which should be sufficient to prevent interference with the epsilon ($\in$) nitrogen of the lysine). One concern is that terminal atoms of side chains can stabilize the protonated form of the lysine; which reduces the nucleophilic properties of lysine, meaning the lysine is less able to perform the required catalytic cycle. Significantly, all naturally occurring aldolases have at least one negatively charged polar-side chain terminal atom (such as a carboxylate oxygen) within about 7.5 angstroms. While that configuration has not prevented naturally occurring aldolases from exhibiting catalytic activity, a conscious choice was made in the design process of the synthetic aldolases disclosed herein to avoid that configuration in the hopes that such avoidance might lead to more effective synthetic aldolases. Thus, one aspect of the concepts disclosed herein encompasses synthetic aldolases including a lysine at the active site where no atoms from other amino acids which could deprotonate the epsilon ($\in$) nitrogen of the active lysine are disposed within about 7.5 angstroms of the epsilon nitrogen.

FIGS. 29B and 29C are related to FIG. 29A, but involve an embodiment in which the about 7.5 angstrom limit is only applied to aspartic acid and glutamic acid side chains. FIG. 29D is related to FIG. 29C, but more broadly defines the entity at the active site as a Schiff-base, as opposed to a lysine (lysine represents a particularly preferred Schiff-base, although other amino acids can be used as a Schiff-base). The Schiff base is the covalent bond between the lysine and the substrate.

FIG. 29E schematically illustrates an embodiment in which hydrophobic residues are incorporated into area proximate the active lysine, to ensure that the active lysine is in a nucleophilic state and ready to perform a catalytic function. The hydrophobic residues are introduced in the design process. All 31 of the synthetic aldolases defined in the attached sequence listing include such hydrophobic residues. The environment around the lysine in the pocket is instead composed of hydrophobic or non-polar residues such as phenylalanine, alanine, valine, serine, threonine, isoleucine, tyrosine, proline, glycine, methionine, and tryptophan. By using these residues, there is no method for stabilizing the protoned N-epsilon of the lysine. This lack of stabilization results in a very nucleophilic, or active, nitrogen which increases the activity of the designed enzymes.

FIG. 29F schematically illustrates aspartic acid and glutamic acid side chains disposed less than about 7.5 angstroms in naturally occurring aldolases.

Another aspect of the concepts disclosed herein are synthetic aldolases based on different protein families than naturally occurring aldolases. The specific sequences for the 31 synthetic aldolases defined in the attached Sequence Listing are based on 8 different protein scaffolds. Each scaffold corresponds to a protein sequence defined in the Protein Data Bank (PDB), operated by the Research Collaboratory for Structural Bioinformatics. Entries in the PDB are defined by four alpha numeric characters. Each different sequence of four characters uniquely defines a specific protein. Significantly, none of those 8 scaffolds corresponds to a naturally occurring aldolase.

FIGS. 30A-30H graphically illustrate how each of the 31 synthetic aldolases defined in the attached Sequence Listing are based on one of the 8 scaffolds noted above, indicating both the location of the active lysine and the amino acid changes to the scaffold required to achieve the specific protein sequence representing the synthetic aldolase. In each Figure, the first column provides an alphanumeric identifier for the specific sequence (i.e., RA31 of FIG. 30A, each such alphanumeric identifier corresponding to a single one of the attached Sequence Listings). The second column (i.e., 14, 13, 15, etc.) indicates the number of amino acid substitutions that sequence includes relative to a particular scaffold. For example, RA31 is a protein sequence that varies from scaffold 1i4n by 14 amino acid changes. The top header refers to a particular amino acid location in the scaffold. The first row defines the specific scaffold using its PDB descriptor, and includes the original amino acid present at each location noted in the header. The Figure then indicates what amino acid replaces the naturally occurring amino acid in the scaffold at that location. The location of the lysine in the active site is indicated by a dashed circle. Referring to RA31 (FIG. 30A), the active lysine (K) is disposed at position 179, and replaces asparagine (the conventional amino acid abbreviations have been employed).

FIG. 30A graphically illustrates synthetic aldolases based on the 1i4n scaffold, indicating both the location of the active lysine and the amino acid changes to the 1i4n scaffold required to achieve the specific protein sequence representing the synthetic aldolase. 1i4n is indole-3-glycerol-phosphate synthase, which is a lyase, not an aldolase (i.e., an enzyme that is a catalyst for a chemical reaction that is not an aldol type reaction). Three of the 31 different synthetic aldolases disclosed herein are based on the 1i4n scaffold. SEQ ID Nos. 1 (RA31), 2 (RA32), and 3 (RA33) each vary from the 1i4n scaffold, but those three synthetic aldolases are related to the 1i4n scaffold. This scaffold exhibits the TIM barrel fold. In two of the three different synthetic aldolases based on the 1i4n scaffold, the active lysine is located a site different than the site of an active lysine in a naturally occurring aldolase (i.e., at the end of the beta 6 strand, or in the beta 4 strand).

The following description provides details on the relative positions of the active lysine (i.e., the lysine involved in the catalytic function) for the three synthetic aldolases based on the 1i4n scaffold. In RA31 (i.e., the synthetic aldolase defined by SEQ ID No. 1) the active lysine is located on beta-strand 6, at the terminus of the strand, as is true in the case of naturally occurring aldolases. RA31 can be distinguished from naturally occurring aldolases because their structures are quite different. RA31 is based on the scaffold of a different type of enzyme (i.e., a lyase, not an aldolase). an entirely different scaffold (i.e., the 1lbl scaffold), which is related to a lyase, not an aldolase. With respect to RA31, the design requirement discussed above with respect to designing an active site such that there are no aspartic acid and glutamic acid side chains disposed less than about 7.5 angstroms from the active lysine can also be used as a basis for distinguishing RA31 from naturally occurring aldolases or variants thereof.

In RA32 (the synthetic aldolase defined by SEQ ID No. 2) and RA33 (the synthetic aldolase defined by SEQ ID No. 3), the active lysine is located on the beta-strand 6, but not at the terminus of beta-strand 6, as is the case for all naturally occurring aldolases having an active lysine on beta-strand 6. In RA32 and RA33, the active lysine is located two amino acid positions earlier in the protein sequence. This shifts the active site deeper into the pocket discussed above in connection with FIGS. 28 and 29A-F. The active lysine is shifted by two positions instead of one, because when moving an odd number of positions away, the epsilon nitrogen of the lysine would be pointed outward and away from the pocket, not inward as desired. Shifting more than about six positions away presents a difficult design challenge. In these two sequences, the terminus of beta-strand 6 is at position 179, such that the active lysine is disposed at position 177. Thus, these two synthetic aldolases (RA32 and RA33) can be distinguished from naturally occurring aldolases based on including an active lysine disposed two positions inward from the terminus of beta-strand 6, as opposed to having an active lysine disposed at the terminus of beta-strand 6 as in naturally occurring aldolases having an active lysine on beta-strand 6.

FIG. 30B graphically illustrates synthetic aldolases based on the 1lbf scaffold, indicating both the location of the active lysine and the amino acid changes to the 1lbf scaffold required to achieve the specific protein sequence representing the synthetic aldolase. 1lbf is related to indole-3-glycerol-phosphate synthase, which is a lyase, not an aldolase. Seven of the 31 different synthetic aldolases disclosed herein are based on the 1lbf scaffold. SEQ ID Nos. 4 (RA22), 5 (RA34), 6 (RA35), 7 (RA36), 8 (RA39), 9 (RA41), and 10 (RA47) each vary from the protein scaffold designated 1lbf, but those seven synthetic aldolases are related to the protein scaffold designated 1lbf. This scaffold exhibits the TIM barrel fold, however, in each of the three different synthetic aldolases based on the 1lbf scaffold, the active lysine is located a site different than the site of an active lysine in a naturally occurring aldolase (i.e., at the end of the beta 6 strand, or in the beta 4 strand).

The following description similarly provides details on the relative positions of the active lysine (i.e., the lysine involved in the catalytic function) for the three synthetic aldolases based on the 1lbf scaffold. In RA22 (the synthetic aldolase defined by SEQ ID No. 4), RA34 (the synthetic aldolase defined by SEQ ID No. 5), RA35 (the synthetic aldolase defined by SEQ ID No. 6), RA36 (the synthetic aldolase defined by SEQ ID No. 7), and RA47 (the synthetic aldolase defined by SEQ ID No. 10), the active lysine is located on beta-strand 5, and not at the terminus of the strand. The active lysine is located two amino acid positions earlier in the protein sequence (i.e., the terminus of beta-strand 5 in this sequence is position 161, while the position of the active lysine in these 5 synthetic aldolases is at position 159, two positions earlier in the sequence). Thus, these 5 synthetic aldolases (RA22, RA34, RA35, RA36 and RA47) can be distinguished from naturally occurring aldolases based on including an active lysine on beta-strand 5, instead of on beta-strands 4 or 6.

In RA39 (the synthetic aldolase defined by SEQ ID No. 8) and RA41 (the synthetic aldolase defined by SEQ ID No. 9), the active lysine is located on beta-strand 6, but two amino acid positions earlier in the protein sequence than the terminus of beta-strand 6. In these two sequences, the terminus of beta-strand 6 is at position 180, such that the active lysine is disposed at position 178. Thus, these two synthetic aldolases (RA39 and RA41) can be distinguished from naturally occurring aldolases based on including an active lysine disposed two positions inward from the terminus of beta-strand 6, as opposed to having an active lysine disposed at the terminus of beta-strand 6, as in naturally occurring aldolases having an active lysine in beta-strand 6.

FIG. 30C graphically illustrates synthetic aldolases based on the 1lbl scaffold, indicating both the location of the active lysine and the amino acid changes to the 1lbl scaffold required to achieve the specific protein sequence representing the synthetic aldolase. 1lbl is also related to indole-3-glycerol-phosphate synthase, which as noted above is not an aldolase. Nine of the 31 different synthetic aldolases disclosed herein are based on the 1lbl scaffold. SEQ ID Nos. 11 (RA6), 12 (RA42), 13 (RA45), 14 (RA46), 15 (RA48), 16 (RA49), 17 (RA55), 18 (RA56), and 19 (RA57) each vary from the protein scaffold designated 1lbl, but those nine synthetic aldolases are related to the protein scaffold designated 1lbl. This scaffold also exhibits the TIM barrel fold, however, in eight of the nine different synthetic aldolases based on the 1lbl scaffold, the active lysine is located a site different than the site of an active lysine in a naturally occurring aldolase (i.e., at the end of the beta 6 strand, or in the beta 4 strand).

The following description similarly provides details on the relative positions of the active lysine (i.e., the lysine involved in the catalytic function) for the three synthetic aldolases based on the 1lbl scaffold. In RA6 (the synthetic aldolase defined by SEQ ID No. 11), RA42 (the synthetic aldolase defined by SEQ ID No. 12), and RA49 (the synthetic aldolase defined by SEQ ID No. 16), the active lysine is located on beta-strand 6, but not at the terminus of the strand, as is true in the case of naturally occurring aldolases having an active lysine on beta-strand 6. Instead, the active lysine is located four amino acid positions earlier in the protein sequence. The terminus of beta-strand 6 in RA6, RA42 and RA49 is position 182, which would be the location of the active lysine in a naturally occurring aldolase having an active lysine in beta-strand 6, while the position of the active lysine in these three synthetic aldolases is at position 178, four positions earlier in the sequence. This shifts the active site deeper into the pocket, as discussed above in connection with FIGS. 28 and 29A-F. Thus, these three synthetic aldolases (RA6, RA42, and RA49) can be distinguished from naturally occurring aldolases based on including an active lysine disposed four positions inward from the terminus of beta-strand 6, as opposed to having an active lysine disposed at the terminus of beta-strand 6 as in naturally occurring aldolases having an active lysine in beta-strand 6.

In RA45 (the synthetic aldolase defined by SEQ ID No. 13) and RA46 (the synthetic aldolase defined by SEQ ID No. 14), the active lysine is located on beta-strand 6, but two amino acid positions earlier in the protein sequence than the terminus of beta-strand 6. In these two sequences, the terminus of beta-strand 6 is at position 182, such that the active lysine is disposed at position 180. Thus, these two synthetic aldolases (RA45 and RA46) can be distinguished from naturally occurring aldolases based on including an active lysine disposed two positions inward from the terminus of beta-strand 6, as opposed to having an active lysine disposed at the terminus of beta-strand 6, as in naturally occurring aldolases having an active lysine in beta-strand 6.

In RA55 (the synthetic aldolase defined by SEQ ID No. 17), RA56 (the synthetic aldolase defined by SEQ ID No. 18), and RA57 (the synthetic aldolase defined by SEQ ID No. 19), the active lysine is located on beta-strand 5. Thus, these three synthetic aldolases (RA55, R56, and RA57) can be distinguished from naturally occurring aldolases based on including an active lysine on beta-strand 5, instead of beta-strands 4 or 6.

In RA48 (the synthetic aldolase defined by SEQ ID No. 15), the active lysine is located on beta-strand 4. While transaldolase, the only naturally occurring aldolase having a TIM fold and an active lysine at a location other than at the terminus of beta-strand 6 does include an active lysine on beta-strand 4, RA48 can be distinguished from transaldolase because their structures are quite different. Transaldolase includes 337 amino acids, and RA48 only 247. RA48 is also based on an entirely different scaffold (i.e., the 1lbl scaffold), which is related to a lyase, not an aldolase. With respect to RA48, and each other specific sequence disclosed herein which includes an active lysine on beta-strand 4, the design requirement discussed above with respect to designing an active site such that there are no aspartic acid and glutamic acid side chains disposed less than about 7.5 angstroms from the active lysine, can also be used as a basis for distinguishing such synthetic aldolases from naturally occurring aldolases or variants thereof. Referring once again to FIG. 29F, note that transaldolase (the bottom portion of the Figure) includes both aspartic acid (D17) and glutamic acid (E96) side chains disposed less than about 7.5 angstroms from the active lysine (K132).

FIG. 30D graphically illustrates a synthetic aldolase based on the 1igs scaffold, indicating both the location of the active lysine and the amino acid changes to the 1igs scaffold required to achieve the specific protein sequence representing the synthetic aldolase. 1igs is also related to indole-3-glycerol-phosphate synthase, which as noted above is not an aldolase. One of the 31 different synthetic aldolases disclosed herein is based on the 1igs scaffold. SEQ ID No. 20 (RA63) varies from the protein scaffold designated 1igs, but that synthetic aldolase is related to the protein scaffold designated 1igs.

In RA63 (the synthetic aldolase defined by SEQ ID No. 20), the active lysine is located on beta-strand 4. While transaldolase does include an active lysine on beta-strand 4, RA63 can be distinguished from transaldolase because their structures are quite different. Transaldolase includes 337 amino acids, and RA63 only 247. RA63 is also based on an entirely different scaffold (i.e., the 1igs scaffold), which is related to a lyase, not an aldolase.

FIG. 30E graphically illustrates synthetic aldolases based on the 1a53 scaffold, indicating both the location of the active lysine and the amino acid changes to the 1a53 scaffold required to achieve the specific protein sequence representing the synthetic aldolase. 1a53 is similarly related to indole-3-glycerol-phosphate synthase, which as noted above is not an aldolase. Five of the 31 different synthetic aldolases disclosed herein are based on the 1a53 scaffold. SEQ ID Nos. 21 (RA26), 22 (RA40), 23 (RA43), 24 (RA53), and 25 (RA68) each vary from the protein scaffold designated 1a53, but these five synthetic aldolases are related to the protein scaffold designated 1a53. Once again this scaffold exhibits the TIM barrel fold, however, in four of the five synthetic aldolases based on the 1a53 scaffold, the active lysine is located a site different than the site of an active lysine in a naturally occurring aldolase (i.e., at the end of the beta 6 strand, or in the beta 4 strand).

In RA40 (the synthetic aldolase defined by SEQ ID No. 22) and RA43 (the synthetic aldolase defined by SEQ ID No. 23), the active lysine is located on beta-strand 6, but two amino acid positions earlier in the protein sequence than the terminus of beta-strand 6. In these two sequences, the terminus of beta-strand 6 is at position 180, such that the active lysine is disposed at position 178. Thus, these two synthetic aldolases (RA40 and RA43) can be distinguished from naturally occurring aldolases based on including an active lysine disposed two positions inward from the terminus of beta-strand 6, as opposed to having an active lysine disposed at the terminus of beta-strand 6, as in naturally occurring aldolases having an active lysine in beta-strand 6.

In RA53 (the synthetic aldolase defined by SEQ ID No. 24) the active lysine is located on beta-strand 5. Thus, RA53 can be distinguished from naturally occurring aldolases based on including an active lysine on beta-strand 5, instead of beta-strands 4 or 6.

In RA68 (the synthetic aldolase defined by SEQ ID No. 25) the active lysine is located on beta-strand 1. Thus, RA68 can be distinguished from naturally occurring aldolases based on including an active lysine on beta-strand 1, instead of beta-strands 4 or 6.

In RA26 (the synthetic aldolase defined by SEQ ID No. 21), the active lysine is located on beta-strand 4. While transaldolase does include an active lysine on beta-strand 4, RA26 can be distinguished from transaldolase because their structures are quite different. Transaldolase includes 337 amino acids, and RA26 only 247. RA26 is also based on an entirely different scaffold (i.e., the 1a53s scaffold), which is related to a lyase, not an aldolase.

FIG. 30F graphically illustrates synthetic aldolases based on the 1thf scaffold, indicating both the location of the active lysine and the amino acid changes to the 1thf scaffold required to achieve the specific protein sequence representing the synthetic aldolase. 1thf is related to imidazole glycerol phosphate synthase, which once again is not an aldolase. Two of the 31 different synthetic aldolases disclosed herein are based on the 1thf scaffold. SEQ ID Nos. 26 (RA17) and 27 (RA58) each vary from the 1thf scaffold, but those two synthetic aldolases are related to the protein scaffold designated 1thf. Once again, this scaffold exhibits the TIM barrel fold, however, in the two synthetic aldolases based on the 1thf scaffold, the active lysine is located a site different than the site of an active lysine in a naturally occurring aldolase (i.e., at the end of the beta 6 strand, or in the beta 4 strand).

In RA17 (the synthetic aldolase defined by SEQ ID No. 26) the active lysine is located on beta-strand 5. Thus, RA17 can be distinguished from naturally occurring aldolases, based on including an active lysine on beta-strand 5, instead of beta-strands 4 or 6.

In RA58 (the synthetic aldolase defined by SEQ ID No. 27) the active lysine is located on beta-strand 6, but not at the terminus of the strand, as is true in the case of naturally occurring aldolases having an active lysine on beta-strand 6. Instead the active lysine is located four amino acid positions earlier in the protein sequence. The terminus of beta-strand 6 in RA58 is at position 173, which would be the location of the active lysine in a naturally occurring aldolase having an active lysine in beta-strand 6, while the position of the active lysine in RA58 is at position 169, four positions earlier in the sequence). Thus, RA58 can be distinguished from naturally occurring aldolases, based on including an active lysine disposed four positions inward from the terminus of beta-strand 6, as opposed to having an active lysine disposed at the terminus of beta-strand 6 as in naturally occurring aldolases having an active lysine in beta-strand 6.

FIG. 30G graphically illustrates synthetic aldolases based on the 1m4w scaffold, indicating both the location of the active lysine and the amino acid changes to the 1m4w scaffold required to achieve the specific protein sequence representing the synthetic aldolase. 1m4w is thermophilic b-1,4-xylanase; again not a naturally occurring aldolase. Three of the 31 different synthetic aldolases disclosed herein are based on the 1m4w scaffold. SEQ ID Nos. 28 (RA59), 29 (RA60), and 30 (RA61) each vary from the protein scaffold designated 1m4w, but those three synthetic aldolases are related to the protein scaffold designated 1m4w. The 1m4w scaffold is a jelly roll, and as noted above, there are no naturally occurring aldolases including an active lysine exhibiting a jelly roll fold. No specific discussion of the location of the active lysine is required to distinguish RA59, RA, 60 and RA61 from naturally occurring aldolases, because there simply are no naturally occurring aldolases exhibiting a jelly roll fold.

FIG. 30H graphically illustrates a synthetic aldolase based on the 1f5j scaffold, indicating both the location of the active lysine and the amino acid changes to the 1f5j scaffold required to achieve the specific protein sequence representing the synthetic aldolase. 1f5j is also a 1,4-xylanase; again not a naturally occurring aldolase. One of the 31 different synthetic aldolases disclosed herein is based on the 1f5j scaffold. SEQ ID No. 31 (RA28) varies from the protein scaffold designated 1f5j, but that synthetic aldolase is related to the protein scaffold designated 1f5j. The 1f5j scaffold is a jelly roll, and as noted above, there are no naturally occurring aldolases including an active lysine exhibiting a jelly roll fold. No specific discussion of the location of the active lysine is required to distinguish RA28 from naturally occurring aldolases, because there simply are no naturally occurring aldolases exhibiting a jelly roll fold.

FIGS. 31A-31C graphically illustrate the synthetic aldolase corresponding to SEQ ID No. 4 (RA22), with the position of the active lysine being indicated by dashed lines. FIG. 31B in particular makes it clear that the active lysine is located in the middle of the beta 5 strand, a position that is unique when compared to all naturally occurring aldolases. Thus, another aspect of the concepts disclosed herein is a synthetic aldolase exhibiting a TIM fold and having an active lysine in the beta 5 strand.

The synthetic aldolases disclosed herein can be characterized by the inclusion of a Schiff-base, or imine (or an enimine), disposed at the active site. FIG. 32 (Prior Art) schematically illustrates the formation of a Schiff-base at an active site during catalysis. That active site is also referred to herein as an active lysine (active indicating that a particular lysine is involved in the catalytic reactions, as some sequences will include lysines in other locations that are not involved in the catalytic reaction). In particular, such synthetic aldolases generally involve an interaction between a carbonyl in the substrate and the epsilon ($\in$) nitrogen of the active site lysine. As discussed above, synthetic aldolases can be differentiated from naturally aldolases involving an active lysine in a number of ways.

All of the synthetic aldolases disclosed herein are based on a scaffold that is not an aldolase.

Some of the synthetic aldolases disclosed herein have active lysines on beta-strand 6, but at a position inward of the terminus of beta-strand 6. All naturally occurring aldolases having an active lysine on beta-strand 6 have the lysine disposed at the terminus of the beta-strand. Such synthetic aldolases include those whose active lysine is either two, four or six positions inward of the end of beta-strand 6.

Some of the synthetic aldolases disclosed herein have active lysines on either beta-strands 1 or 5, and all naturally occurring aldolases having an active lysine have the active lysine either on beta-strand 4 or at the end of beta-strand 6.

Some of the synthetic aldolases disclosed herein have active lysines on beta-strand 4 (as does transaldolase), but those that do are based on significantly smaller scaffolds than transaldolase (247 amino acids verses 337 amino acids).

Some of the synthetic aldolases disclosed herein have active lysines and exhibit a fold other than a TIM fold. All naturally occurring aldolases including an active lysine include a TIM fold.

A majority of the synthetic aldolases disclosed herein have active lysines disposed in a pocket, whose sequences have been designed such that no other amino acid side chains are disposed close enough to deprotonate the epsilon ($\in$) nitrogen of the active lysine.

All of the synthetic aldolases disclosed herein are based on designs with a transition state-protein van der Waals attractive energy<−5.0 kcal/mol. This is a method for determining how buried the designed active sites are, particularly how buried the TS/substrate is. The van der Waals attractive energy is a measurement of how much packing there is around the substrate. If there is too little packing (i.e., the van der Waals attractive energy>−5 kcal/mole), the substrate is likely not buried enough to actually become bound to the active site. This type of metric is employed when designing the synthetic aldolase to make sure that the synthetic aldolase can bind the substrate.

Additionally, there is a method for measuring the destabilization of the protein due to the introduced mutations. Effectively, the internal energy of just the protein in the presence of the substrate/ligand/TS is calculated, and then in its absence. This change in energy, Delta G (technically Delta Delta G—since the energy of each individual state is a Delta G that compares the folded protein energy to the unfolded protein), indicates how stable the protein is in the absence of the substrate. If the redesigned active site shape and structure is too dependent on interactions with the substrate, the protein will "collapse" and incorrectly fold when it is expressed.

All of the synthetic aldolases disclosed herein are based on designs with more than 35 Cβ (carbon-β) atoms within 10 angstroms of the TS, and less than 85 Cβ (carbon-β) atoms within 10 angstroms of the TS, to achieve an active site that was neither too buried nor too exposed. FIG. 33 schematically illustrates this additional design consideration.

All of the synthetic aldolases disclosed herein are based on designs in which the active site is well packed, stable, and ready for the substrate to come along and be bound in the active site.

All of the synthetic aldolases disclosed herein are based on designs in which the solvent accessible surface (SASA) of the TS was more than 10 angstroms squared, as an SASA value of less than 10 angstroms squared indicates that there is insufficient access to binding pocket.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for making an enzyme that is a hydrolase, a lyase, an isomerase, or a transferase, comprising:
   constructing a transition state model for a desired chemical reaction catalyzed by a hydrolase, lyase, isomerase, or a transferase,
   identifying reactive amino acid functional groups and functional group geometry to catalyze the chemical reaction;
   constructing a set of amino acid rotamers from a structural library, where the rotamers incorporate the functional groups and functional group geometry;
   computationally identifying a transition state model placement in a set of candidate protein backbone scaffolds by a hashing algorithm, where the position of the transition state model for the rotamers independently placed at scaffold positions is recorded in a hash table if there are no clashes with the protein backbone or catalytic side chains, and the hash table processed to extract sets of positions compatible with the functional group geometry;
   computationally selecting an amino acid sequence to accommodate the identified scaffold and the transition state model placement, thereby identifying a putative enzyme; and
   expressing the putative hydrolase, lyase, isomerase, or transferase enzyme and confirming enzymatic activity of the putative hydrolase, lyase, isomerase, or transferase enzyme.

2. The method of claim 1, wherein the active site has two to four active site residues.

3. The method of claim 2, wherein the catalytic residues are selected from the group consisting of: Asp, Glu, Asn, His, Cys, Ser, Tyr, Lys, and Arg.

4. The method of claim 1, wherein the amino acid rotamer(s) is an inverse rotamer based on the geometry of the reactive functional groups.

5. The method of claim 4, wherein identifying an active site placement comprises comparing the scaffold backbone coordinates to inverse rotamer coordinate computations.

6. The method of claim 5, wherein the hashing algorithm comprises six-dimensional hashing.

7. The method of claim 1, wherein the rotamers from a structural library are constructed from backbone scaffold positions, a transition state model placed, and the geometry of the resulting transition state model scored.

8. The method of claim 1, wherein reactive functional groups are identified using a transition state model surrounded by the protein functional groups stabilizing the transition state.

9. The method of claim 1, further comprising, identifying amino acid alterations that improve enzymatic activity by directed evolution.

10. The method of claim 1, wherein the set of candidate scaffolds comprises a fold selected from the Structural Classification of Proteins (SCOP) Classes: (i) Beta Proteins or (ii) Alpha and Beta Proteins.

11. The method of claim 1, wherein the set of candidate scaffolds comprises a fold selected from an alpha-beta barrel, jelly roll fold, Rossmann fold, greek key, and globin.

12. The method of claim 1, wherein the amino acid sequence of the identified scaffold is altered to optimize transition state binding energy.

13. The method of claim 1, further comprising estimating catalytic efficacy based on fit of catalytic residues to active site and computed transition state binding energy.

14. The method of claim 1, wherein at least 100,000 active site placements are positioned in the set of candidate protein backbones.

15. A method for making an enzyme that is a hydrolase, a lyase, an isomerase, or a transferase having two to four active site residues, comprising:
constructing a transition state model for a desired chemical reaction catalyzed by a hydrolase, lyase, isomerase, or a transferase,
identifying two to four reactive amino acid functional groups and functional group geometry to catalyze the chemical reaction;
constructing a set of amino acid rotamers from a structural library, where the rotamers incorporate the functional groups and functional group geometry;
computationally identifying a transition state model placement in a set of candidate protein backbone scaffolds by a hashing algorithm, where the position of the transition state model for the rotamers independently placed at scaffold positions is recorded in a hash table if there are no clashes with the protein backbone or catalytic side chains, and the hash table processed to extract sets of positions compatible with the functional group geometry;
computationally selecting an amino acid sequence to accommodate the identified scaffold and the transition state model placement, thereby identifying a putative enzyme; and
expressing the putative hydrolase, a lyase, an isomerase, or transferase enzyme and confirming enzymatic activity of the putative hydrolase, a lyase, an isomerase, or transferase enzyme.

16. The method of claim 15, wherein the catalytic residues are selected from the group consisting of: Asp, Glu, Asn, His, Cys, Ser, Tyr, Lys, and Arg.

17. A method for making an enzyme that catalyzes a hydrolase reaction, comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative hydrolase enzyme; producing the putative hydrolase enzyme and confirming hydrolase enzymatic activity.

18. A method for making an enzyme that catalyzes an isomerase reaction, comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative isomerase enzyme; producing the putative isomerase enzyme and confirming isomerase enzymatic activity.

19. A method for making an enzyme that catalyzes a lyase reaction, comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative lyase enzyme; producing the putative lyase enzyme and confirming lyase enzymatic activity.

20. A method for making an enzyme that catalyzes a transferase reaction, comprising: identifying reactive amino acid functional groups and functional group geometry to catalyze said reaction, thereby constructing an active site; constructing a set of amino acid rotamers from a structural library, where the rotamers incorporate said functional groups and said functional group geometry; computationally identifying an active site placement in a set of candidate protein backbone scaffolds by a hashing algorithm, where the set of amino acid rotamers comprising said active site placement is positioned on a candidate protein backbone so that the active site satisfies protein stereochemistry and maintains catalytic geometry; computationally selecting an amino acid sequence to accommodate the identified scaffold and the placed active site, thereby identifying a putative transferase enzyme; producing the putative transferase enzyme and confirming transferase enzymatic activity.

21. The method of any one of claims 17-20, wherein the active site has two to four active site residues.

22. The method of claim 21, wherein the catalytic residues are selected from the group consisting of: Asp, Glu, Asn, His, Cys, Ser, Tyr, Lys, and Arg.

23. The method of claim any one of claims 15-20, wherein the amino acid rotamer(s) is an inverse rotamer based on the geometry of the reactive functional groups.

24. The method of claim 23, wherein identifying an active site placement comprises comparing the scaffold backbone coordinates to inverse rotamer coordinate computations.

25. The method of claim 24, wherein the hashing algorithm comprises six-dimensional hashing.

26. The method of any one of claims 15-20, wherein the rotamers from a structural library are constructed from backbone scaffold positions, a transition state model placed, and the geometry of the resulting transition state model scored.

27. The method of any one of claims 15-20, wherein reactive functional groups are identified using a transition state model surrounded by the protein functional groups stabilizing the transition state.

28. The method of any one of claims 15-20, further comprising, identifying amino acid alterations that improve enzymatic activity by directed evolution.

29. The method of any one of claims 15-20, wherein the set of candidate scaffolds comprises a fold selected from the Structural Classification of Proteins (SCOP) Classes: (i) Beta Proteins or (ii) Alpha and Beta Proteins.

30. The method of any one of claims 15-20, wherein the set of candidate scaffolds comprises a fold selected from an alpha-beta barrel, jelly roll fold, Rossmann fold, greek key, and globin.

31. The method of any one of claims 15-20, wherein the amino acid sequence of the identified scaffold is altered to optimize transition state binding energy.

32. The method of any one of claims 15-20, further comprising estimating catalytic efficacy based on fit of catalytic residues to active site and computed transition state binding energy.

33. The method of any one of claims 15-20, wherein at least 100,000 active site placements are positioned in the set of candidate protein backbones.

* * * * *